United States Patent
Kim et al.

(10) Patent No.: US 9,205,260 B2
(45) Date of Patent: Dec. 8, 2015

(54) METHODS FOR STIMULATING A DORSAL ROOT GANGLION

(75) Inventors: Daniel H. Kim, Houston, TX (US); Mir A. Imran, Los Altos, CA (US)

(73) Assignees: The Board of Trustees of the Leland Stanford Junior University, Palo Alto, CA (US); Spinal Modulation, Inc., Menlo Park, CA (US)

( * ) Notice: Subject to any disclaimer, the term of this patent is extended or adjusted under 35 U.S.C. 154(b) by 0 days.

(21) Appl. No.: 13/550,439

(22) Filed: Jul. 16, 2012

(65) Prior Publication Data
US 2012/0283697 A1  Nov. 8, 2012

Related U.S. Application Data

(60) Continuation of application No. 12/369,706, filed on Feb. 11, 2009, now Pat. No. 8,229,565, which is a division of application No. 11/222,516, filed on Sep. 7, 2005, now Pat. No. 7,502,651.

(60) Provisional application No. 60/608,357, filed on Sep. 8, 2004.

(51) Int. Cl.
*A61K 9/22* (2006.01)
*A61N 1/36* (2006.01)
*A61N 1/05* (2006.01)

(52) U.S. Cl.
CPC .......... *A61N 1/36067* (2013.01); *A61N 1/0558* (2013.01); *A61N 1/36071* (2013.01);
(Continued)

(58) Field of Classification Search
CPC ............ A61N 1/36067; A61N 1/0558; A61N 1/36139; A61N 1/36171; A61N 1/36071
USPC .......... 604/890.1, 891.1, 93.01, 131
See application file for complete search history.

(56) References Cited

U.S. PATENT DOCUMENTS

| 525,891 A | 9/1894 | Fricke |
| 3,724,467 A | 4/1973 | Avery et al. |

(Continued)

FOREIGN PATENT DOCUMENTS

| CN | 2401143 Y | 10/2000 |
| EP | 0779080 A | 6/1997 |

(Continued)

OTHER PUBLICATIONS

J. R. Wedley and C. A. Gauci, Handbook of Clinical Techniques in the Management of Chronic Pain, Nov. 27, 1996, Taylor & Francis, pp. 17-19.*

(Continued)

*Primary Examiner* — Edelmira Bosques
(74) *Attorney, Agent, or Firm* — Shay Glenn LLP

(57) ABSTRACT

Some embodiments of the present invention provide stimulation systems and components for selective stimulation and/or neuromodulation of one or more dorsal root ganglia through implantation of an electrode on, in or around a dorsal root ganglia. Some other embodiments of the present invention provide methods for selective neurostimulation of one or more dorsal root ganglia as well as techniques for applying neurostimulation to the spinal cord. Still other embodiments of the present invention provide stimulation systems and components for selective stimulation and/or neuromodulation of one or more dorsal root ganglia through implantation of an electrode on, in or around a dorsal root ganglia in combination with a pharmacological agent.

16 Claims, 47 Drawing Sheets

(52) U.S. Cl.
CPC ........ *A61N1/36139* (2013.01); *A61N 1/36171* (2013.01); *A61N 1/0551* (2013.01); *A61N 1/0568* (2013.01); *A61N 1/36017* (2013.01); *A61N 1/36021* (2013.01)

(56) References Cited

U.S. PATENT DOCUMENTS

| | | | |
|---|---|---|---|
| 3,845,770 A | 11/1974 | Theeuwes et al. |
| 3,916,899 A | 11/1975 | Theeuwes et al. |
| 4,141,367 A | 2/1979 | Ferreira |
| 4,232,679 A | 11/1980 | Schulman |
| 4,298,003 A | 11/1981 | Theeuwes et al. |
| 4,313,448 A | 2/1982 | Stokes |
| 4,374,527 A | 2/1983 | Iversen |
| 4,479,491 A | 10/1984 | Martin |
| 4,549,556 A | 10/1985 | Tarjan et al. |
| 4,573,481 A | 3/1986 | Bullara |
| 4,577,642 A | 3/1986 | Stokes |
| 4,590,946 A | 5/1986 | Loeb |
| 4,607,639 A | 8/1986 | Tanagho et al. |
| 4,739,764 A | 4/1988 | Lue et al. |
| 4,786,155 A | 11/1988 | Fantone et al. |
| 4,803,988 A | 2/1989 | Thomson |
| 4,920,979 A | 5/1990 | Bullara |
| 4,940,065 A | 7/1990 | Tanagho et al. |
| 4,950,270 A | 8/1990 | Bowman et al. |
| 4,976,711 A | 12/1990 | Parins et al. |
| 5,135,525 A | 8/1992 | Biscoping et al. |
| 5,270,099 A | 12/1993 | Kamiyama et al. |
| 5,299,569 A | 4/1994 | Wernicke et al. |
| 5,344,438 A | 9/1994 | Testerman et al. |
| 5,358,514 A | 10/1994 | Schulman et al. |
| 5,370,644 A | 12/1994 | Langberg |
| 5,411,537 A | 5/1995 | Munshi et al. |
| 5,411,540 A | 5/1995 | Edell et al. |
| 5,417,719 A | 5/1995 | Hull et al. |
| 5,419,763 A | 5/1995 | Hildebrand |
| 5,458,626 A | 10/1995 | Krause |
| 5,489,294 A | 2/1996 | McVenes et al. |
| 5,505,201 A | 4/1996 | Grill et al. |
| 5,514,175 A | 5/1996 | Kim et al. |
| 5,584,835 A | 12/1996 | Greenfield |
| 5,634,462 A | 6/1997 | Tyler et al. |
| 5,643,330 A | 7/1997 | Holsheimer et al. |
| 5,702,429 A | 12/1997 | King |
| 5,711,316 A | 1/1998 | Elsberry et al. |
| 5,713,922 A | 2/1998 | King |
| 5,733,322 A | 3/1998 | Starkebaum |
| 5,741,319 A | 4/1998 | Woloszko et al. |
| 5,755,750 A | 5/1998 | Petruska et al. |
| 5,776,170 A | 7/1998 | MacDonald et al. |
| 5,807,339 A | 9/1998 | Bostrom et al. |
| 5,824,021 A | 10/1998 | Rise |
| 5,865,843 A | 2/1999 | Baudino |
| 5,871,531 A | 2/1999 | Struble |
| 5,885,290 A | 3/1999 | Guerrero et al. |
| 5,938,690 A | 8/1999 | Law et al. |
| 5,948,007 A | 9/1999 | Starkebaum et al. |
| 5,957,965 A | 9/1999 | Moumane et al. |
| 5,983,141 A | 11/1999 | Sluijter et al. |
| 5,984,896 A | 11/1999 | Boyd |
| 6,002,964 A | 12/1999 | Feler et al. |
| 6,044,297 A | 3/2000 | Sheldon et al. |
| 6,045,532 A | 4/2000 | Eggers et al. |
| 6,051,017 A | 4/2000 | Loeb et al. |
| 6,104,957 A | 8/2000 | Alo et al. |
| 6,120,467 A | 9/2000 | Schallhorn |
| 6,161,048 A | 12/2000 | Sluijter et al. |
| 6,175,764 B1 | 1/2001 | Loeb et al. |
| 6,181,965 B1 | 1/2001 | Loeb et al. |
| 6,185,455 B1 | 2/2001 | Loeb et al. |
| 6,205,359 B1 | 3/2001 | Boveja |
| 6,208,902 B1 | 3/2001 | Boveja |
| 6,214,016 B1 | 4/2001 | Williams et al. |
| 6,259,952 B1 | 7/2001 | Sluijter et al. |
| 6,298,256 B1 | 10/2001 | Meyer |
| 6,314,325 B1 | 11/2001 | Fitz |
| 6,319,241 B1 | 11/2001 | King et al. |
| 6,349,233 B1 | 2/2002 | Adams |
| 6,353,762 B1 | 3/2002 | Baudino et al. |
| 6,356,786 B1 | 3/2002 | Rezai et al. |
| 6,360,750 B1 | 3/2002 | Gerber et al. |
| 6,366,814 B1 | 4/2002 | Boveja et al. |
| 6,393,325 B1 | 5/2002 | Mann et al. |
| 6,413,255 B1 | 7/2002 | Stern |
| 6,425,887 B1 | 7/2002 | McGuckin et al. |
| 6,438,423 B1 | 8/2002 | Rezai et al. |
| 6,440,090 B1 | 8/2002 | Schallhorn |
| 6,466,821 B1 | 10/2002 | Pianca et al. |
| 6,493,588 B1 | 12/2002 | Malaney et al. |
| 6,510,347 B2 | 1/2003 | Borkan |
| 6,512,958 B1 | 1/2003 | Swoyer et al. |
| 6,516,227 B1 | 2/2003 | Meadows et al. |
| 6,517,542 B1 | 2/2003 | Papay et al. |
| 6,522,926 B1 | 2/2003 | Kieval et al. |
| 6,535,767 B1 | 3/2003 | Kronberg |
| 6,582,441 B1 | 6/2003 | He et al. |
| 6,587,725 B1 | 7/2003 | Durand et al. |
| 6,605,094 B1 | 8/2003 | Mann et al. |
| 6,606,521 B2 | 8/2003 | Paspa et al. |
| 6,611,715 B1 | 8/2003 | Boveja |
| 6,625,496 B1 | 9/2003 | Ollivier |
| 6,638,276 B2 | 10/2003 | Sharkey et al. |
| 6,658,302 B1 | 12/2003 | Kuzma et al. |
| 6,714,822 B2 | 3/2004 | King et al. |
| 6,748,276 B1 | 6/2004 | Diagnault, Jr. et al. |
| 6,754,539 B1 | 6/2004 | Erickson et al. |
| 6,788,975 B1 | 9/2004 | Whitehurst et al. |
| 6,792,318 B2 | 9/2004 | Chitre et al. |
| 6,832,115 B2 | 12/2004 | Borkan |
| 6,835,194 B2 | 12/2004 | Johnson et al. |
| 6,839,588 B1 | 1/2005 | Rudy |
| 6,849,075 B2 | 2/2005 | Bertolero et al. |
| 6,862,479 B1 | 3/2005 | Whitehurst et al. |
| 6,871,099 B1 | 3/2005 | Whitehurst et al. |
| 6,873,342 B2 | 3/2005 | Perry et al. |
| 6,889,094 B1 | 5/2005 | Kuzma et al. |
| 6,901,287 B2 | 5/2005 | Davis et al. |
| 6,902,547 B2 | 6/2005 | Aves et al. |
| 6,909,917 B2 | 6/2005 | Woods et al. |
| 6,928,320 B2 | 8/2005 | King |
| 6,971,391 B1 | 12/2005 | Wang et al. |
| 6,978,180 B2 | 12/2005 | Tadlock |
| 7,047,082 B1 | 5/2006 | Schrom et al. |
| 7,096,070 B1 | 8/2006 | Jenkins et al. |
| 7,127,287 B2 | 10/2006 | Duncan et al. |
| 7,181,289 B2 | 2/2007 | Pflueger et al. |
| 7,333,857 B2 | 2/2008 | Campbell |
| 7,337,005 B2 | 2/2008 | Kim et al. |
| 7,337,006 B2 | 2/2008 | Kim et al. |
| 7,447,546 B2 | 11/2008 | Kim et al. |
| 7,450,993 B2 | 11/2008 | Kim et al. |
| 7,502,651 B2 | 3/2009 | Kim et al. |
| 7,580,753 B2 | 8/2009 | Kim et al. |
| 8,082,039 B2 | 12/2011 | Kim et al. |
| 8,229,565 B2 | 7/2012 | Kim et al. |
| 2001/0003799 A1 | 6/2001 | Boveja |
| 2001/0006967 A1 | 7/2001 | Crain et al. |
| 2002/0064841 A1 | 5/2002 | Klemic et al. |
| 2002/0077684 A1 | 6/2002 | Clemens et al. |
| 2002/0087113 A1* | 7/2002 | Hartlaub .................... 604/65 |
| 2002/0099430 A1 | 7/2002 | Verness |
| 2002/0116030 A1 | 8/2002 | Rezai |
| 2002/0128694 A1 | 9/2002 | Holsheimer |
| 2002/0147486 A1 | 10/2002 | Soukup et al. |
| 2002/0198527 A1 | 12/2002 | Muckter |
| 2003/0018367 A1 | 1/2003 | Dilorenzo |
| 2003/0023241 A1 | 1/2003 | Drewry et al. |
| 2003/0045919 A1 | 3/2003 | Swoyer et al. |
| 2003/0069569 A1 | 4/2003 | Burdette et al. |
| 2003/0078633 A1 | 4/2003 | Firlik et al. |
| 2003/0088301 A1 | 5/2003 | King |
| 2003/0100933 A1 | 5/2003 | Ayal et al. |
| 2003/0114905 A1 | 6/2003 | Kuzma |

(56) References Cited

U.S. PATENT DOCUMENTS

| | | |
|---|---|---|
| 2003/0130577 A1 | 7/2003 | Purdy et al. |
| 2003/0144657 A1 | 7/2003 | Bowe et al. |
| 2003/0144709 A1 | 7/2003 | Zabara et al. |
| 2003/0181958 A1 | 9/2003 | Dobak, III |
| 2003/0187490 A1 | 10/2003 | Gliner |
| 2003/0195602 A1 | 10/2003 | Boling |
| 2003/0220677 A1 | 11/2003 | Doan et al. |
| 2004/0015202 A1 | 1/2004 | Chandler et al. |
| 2004/0019359 A1 | 1/2004 | Worley et al. |
| 2004/0019369 A1 | 1/2004 | Duncan et al. |
| 2004/0059404 A1 | 3/2004 | Bjorklund et al. |
| 2004/0116977 A1 | 6/2004 | Finch et al. |
| 2004/0122360 A1 | 6/2004 | Waldhauser et al. |
| 2004/0122477 A1 | 6/2004 | Whitehurst et al. |
| 2004/0122497 A1 | 6/2004 | Zhang et al. |
| 2004/0122498 A1 | 6/2004 | Zhang et al. |
| 2004/0147992 A1 | 7/2004 | Bluger et al. |
| 2004/0210290 A1 | 10/2004 | Omar-Pasha |
| 2004/0215286 A1 | 10/2004 | Stypulkowski |
| 2004/0230273 A1 | 11/2004 | Cates et al. |
| 2004/0230280 A1 | 11/2004 | Cates et al. |
| 2004/0243210 A1 | 12/2004 | Morgan et al. |
| 2005/0027338 A1 | 2/2005 | Hill |
| 2005/0033295 A1 | 2/2005 | Wisnewski |
| 2005/0033393 A1 | 2/2005 | Daglow |
| 2005/0038489 A1 | 2/2005 | Grill |
| 2005/0070982 A1 | 3/2005 | Heruth et al. |
| 2005/0080325 A1 | 4/2005 | Erickson |
| 2005/0096718 A1 | 5/2005 | Gerber et al. |
| 2005/0149154 A1 | 7/2005 | Cohen et al. |
| 2005/0154437 A1 | 7/2005 | Williams |
| 2005/0159799 A1 | 7/2005 | Daglow et al. |
| 2005/0203599 A1 | 9/2005 | Garabedian et al. |
| 2005/0222647 A1 | 10/2005 | Wahlstrand et al. |
| 2005/0251237 A1 | 11/2005 | Kuzma et al. |
| 2006/0004364 A1 | 1/2006 | Green et al. |
| 2006/0009820 A1 | 1/2006 | Royle |
| 2006/0041295 A1 | 2/2006 | Osypka |
| 2006/0052836 A1 | 3/2006 | Kim et al. |
| 2006/0052856 A1 | 3/2006 | Kim et al. |
| 2006/0064150 A1 | 3/2006 | Heist et al. |
| 2006/0089609 A1 | 4/2006 | Bleich et al. |
| 2006/0089696 A1 | 4/2006 | Olsen et al. |
| 2006/0094976 A1 | 5/2006 | Bleich |
| 2006/0095088 A1 | 5/2006 | DeRidder |
| 2006/0155344 A1 | 7/2006 | Rezai et al. |
| 2006/0161235 A1 | 7/2006 | King |
| 2006/0167525 A1 | 7/2006 | King |
| 2006/0195169 A1 | 8/2006 | Gross et al. |
| 2006/0200121 A1 | 9/2006 | Mowery |
| 2006/0206118 A1 | 9/2006 | Kim et al. |
| 2006/0241716 A1 | 10/2006 | Finch et al. |
| 2006/0247750 A1 | 11/2006 | Seifert et al. |
| 2007/0043400 A1 | 2/2007 | Donders et al. |
| 2007/0060954 A1 | 3/2007 | Cameron et al. |
| 2007/0123954 A1 | 5/2007 | Gielen et al. |
| 2007/0213671 A1 | 9/2007 | Hiatt |
| 2007/0270928 A1 | 11/2007 | Erlebacher |
| 2008/0009927 A1 | 1/2008 | Vilims |
| 2008/0140152 A1 | 6/2008 | Imran et al. |
| 2008/0140153 A1 | 6/2008 | Burdulis |
| 2008/0140169 A1 | 6/2008 | Imran |
| 2008/0147156 A1 | 6/2008 | Imran |
| 2008/0154349 A1 | 6/2008 | Rossing et al. |
| 2008/0167698 A1 | 7/2008 | Kim et al. |
| 2008/0183221 A1 | 7/2008 | Burdulis |
| 2008/0183257 A1 | 7/2008 | Imran et al. |
| 2008/0188916 A1 | 8/2008 | Jones et al. |
| 2010/0137938 A1 | 6/2010 | Imran et al. |
| 2010/0179562 A1 | 7/2010 | Linker et al. |
| 2010/0249875 A1 | 9/2010 | Kishawi et al. |
| 2010/0292769 A1 | 11/2010 | Brounstein et al. |
| 2011/0257693 A1 | 10/2011 | Burdulis |
| 2011/0276056 A1 | 11/2011 | Grigsby et al. |
| 2012/0158094 A1 | 6/2012 | Kramer et al. |
| 2012/0197370 A1 | 8/2012 | Kim et al. |
| 2012/0310140 A1 | 12/2012 | Kramer et al. |
| 2014/0200625 A1 | 7/2014 | Kim et al. |
| 2014/0343624 A1 | 11/2014 | Kramer |

FOREIGN PATENT DOCUMENTS

| | | |
|---|---|---|
| EP | 1304135 A2 | 4/2003 |
| JP | 03041191 B2 | 6/1991 |
| JP | H06-218064 A | 8/1994 |
| JP | 8500996 A | 2/1996 |
| JP | 8080353 A | 3/1996 |
| JP | 10243954 A | 9/1998 |
| JP | 2004512105 | 4/2004 |
| JP | 2006523215 | 10/2004 |
| JP | 2005516697 | 6/2005 |
| JP | 2006508768 | 3/2006 |
| JP | 2008526299 | 7/2008 |
| WO | WO 02/096512 A1 | 12/2002 |
| WO | WO 03/018113 A1 | 3/2003 |
| WO | WO 03/041559 A2 | 5/2003 |
| WO | WO 03/043690 A1 | 5/2003 |
| WO | WO 03/063692 A2 | 8/2003 |
| WO | WO 03/066154 A2 | 8/2003 |
| WO | WO 03/084433 A2 | 10/2003 |
| WO | WO 03/090599 A2 | 11/2003 |
| WO | WO 2005/092432 A1 | 10/2005 |
| WO | WO 2006/033039 A1 | 3/2006 |
| WO | WO 2006/084635 A2 | 8/2006 |

OTHER PUBLICATIONS

Merriam-Webster's Dictionary. Houghton Mifflin Company, 1995.*

Abdulla et al.; Axotomy—and autotomy-induced changes in the excitability of rat dorsal root ganglion neurons; J Neurophysiol; 85(2); pp. 630-643; Feb. 2001.

Advanced Neuromodulation Systems, Inc. (ANSI) Research Briefing dated Aug. 20, 2004 by Stephens Inc. Investment Bankers pp. 1-4.

Advanced Neuromodulation Systems, Inc. (ANSI) Research Bulletin dated Jul. 2, 2004 by Stephens Inc. Investment Bankers pp. 1-7.

Advanced Neuromodulation Systems, Inc. (ANSI) Research Bulletin dated Jul. 27, 2004 by Stephens Inc. Investment Bankers pp. 1-9.

Advanced Neuromodulation Systems, Inc. Equity Research dated Jan. 16, 2003 by Pacific Growth Equities pp. 1-8.

Alo, Kenneth M. New Trends in Neuromodulation for the Management of Neuropathic Pain. Neurosurgery. 50 (4): 690-703. Apr. 2002.

Aoki, Yasuchika et al. Distribution and Immunocytochemical Characterization of Dorsal Root Ganglion Neurons Innervating the Lumbar Intervertebral Disc in Rats: A Review. Life Sciences. 74 (21): 2627-2642. Apr. 2004.

Askar, Zahid, et al. Scott Wiring for Direct Repair of Lumbar Spondylolysis. . Spine. 28 (4): 354-357. Feb. 2003.

Baba, Hiroshi et al. Peripheral Inflammation Facilitates A? Fiber-Mediated Synaptic Input to the Substantia Gelatinosa of the Adult Rat Spinal Cord. The Journal of Neuroscience. 19 (2): 859-867. Jan. 1999.

Bajwa, Zahid H. et al. Herpetic Neuralgia: Use of Combination Therapy for Pain Relief in Acute and Chronic Herpes Zoster. Geriatrics. 56 (12): 18-24. Dec. 2001.

Barendse, G.A. et al. Randomized Controlled Trial of Percutaneous Intradiscal Radiofrequency Thermocoagulation for Chronic Discogenic Back Pain: Lack of Effect From a 90-Second 70 C Lesion. Spine. 26 (3): 287-92. (Abstract Only). Feb. 1, 2001.

Barlocher, C.B. et al. Kryorhizotomy: An Alternative Technique for Lumbar Medial Branch Rhizotomy in Lumbar Facet Syndrome. J Neurosurg. 98 (1): 14-20. (Abstract Only). Jan. 2003.

Blau, A. et al. Characterization and Optimization of Microelectrode Arrays for In Vivo Nerve Signal Recording and Stimulation. Biosens Bioelectron. 12 (9-10): 883-92. (Abstract Only). Nov. 1997.

Boston Scientific a Neuromodulation Primer dated Jun. 9, 2004 in Medical Supplies and Devices, published by Susquehanna Financial Group, LLLP pp. 1-17.

Brammah, T.B. et al. . Syringomyelia as a Complication of Spinal Arachnoiditis. Spine. 19 (22): 2603-5. (Abstract Only). Nov. 15, 1994.

(56) References Cited

OTHER PUBLICATIONS

Braverman D.L. et al. Using Gabapentin to Treat Failed Back Surgery Syndrome Caused by Epidural Fibrosis: A Report of 2 Cases. Arch Phys Med Rehabil. 82 (5): 691-3. (Abstract Only). May 2001.
Burton et al.; The organization of the seventh lumbar spinal ganglion of the cat; J Comp Neurol.; 149(2); pp. 215-232; May 15, 1973.
Carlton, Susan M. et al. Tonic Control of Peripheral Cutaneous Nociceptors by Somatostatin Receptors. Journal of Neuroscience. 21 (11): 4042-4049. Jun. 1, 2001.
Chaplan, S.R. et al. Quantitative Assessment of Tactile Allodynia in the Rat Paw. Journal of Neuroscience Methods. 53 (1): 55-63. Jul. 1994.
Cho, J. Percutaneo Radiofrequency Lumbar Facet Rhizotomy in Mechanical Low Back Pain Syndrome. Stereotact Funct Neurosurg. 68 (1-4): 212-7. (Abstract Only). (month unavailable) 1997.
Clark, Robert K. "Anatomy and physiology: understanding the human body"; Jones & Bartlett Publishers; Sudbury, MA; ISBN 0-7637-4816-6; Chapter 12; pp. 213-215; Feb. 28, 2005.
Crampon, M.-A. et al. Nerve Cuff Electrode With Shape Memory Alloy Armature: Design and Fabrication. Bio-Medical Materials and Engineering. 12 (4): 397-410. (month unavailable) 2002.
Cuoco, Jr., Frank A. et al. Measurement of External Pressures Generated by Nerve Cuff Electrodes. IEEE Transactions on Rehabilitation Engineering. 8 (1): 35-41. Mar. 2000.
Cyberonics, Inc. Equity Research dated Jan. 16, 2003 by Pacific Growth Equities pp. 1-14.
Denny, N.M. et al. Evaluation of an Insulated Tuohy Needle System for the Placement of Interscalene Brachial Plex Catheters. Anaesthesia. 58 (6): 554-7. (Abstract Only). Jun. 2003.
Dreyfuss, Paul et al. Efficacy and Validity of Radiofrequency Neurotomy for Chronic Lumbar Zygapophysial Joint Pain. Spine. 25 (10): 1270-1277. May 15, 2000.
Dubuisson, D. Treatment of Occipital Neuralgia by Partial Posterior Rhizotomy at C1-3. J Neurosurg. 82 (4): 581-6. (Abstract Only). Apr. 1995.
Eschenfelder, Sebastian et al. Dorsal Root Section Elicits Signs of Neuropathic Pain Rather than Reversing Them in Rats With L5 Spinal Nerve Injury. Pain. 87 (2): 213-219. Aug. 2000.
Firth, Ava et al. Development of a Scale to Evaluate Postoperative Pain in Dogs. J Am Vet Med Assoc. 214 (5): 651-659. Mar. 1, 1999.
Garcia Cosamalon, P. J. et al. Dorsal Percutaneo Radiofrequency Rhizotomy Guided With CT Scan in Intercostal Neuralgias. Technical note. Acta Neurochir (Wien). 109 (3-4): 140-1. (month unavailable) 1991.
Giorgi, C. et al. Surgical Treatment of Glossopharyngeal Neuralgia and Pain From Cancer of the Nasopharynx. A 20-Year Experience. J Neurosurg. 61 (5): 952-5. (Abs. Only). Nov. 1984.
Gocer, A.I. et al. Percutaneous Radiofrequency Rhizotomy of Lumbar Spinal Facets the Results of 46 cases. Neurosurg Rev. 20 (2): 114-6. (Abstract Only). (month unavailable) 1997.
Haller, H. et al. Treatment of Chronic Neuropathic Pain After Traumatic Central Cervical Cord Lesion with Gabapentin. Journal of Neural Transmission. 110 (9): 977-981. Sep. 2003.
Herron, L.D. Selective Nerve Root Block in Patient Selection for Lumbar Surgery: Surgical Results. J Spinal Disord. 2 (2): 75-9. (Abstract Only). Jun. 1989.
Higuchi, Yoshinori, et al. Exposure of the Dorsal Root Ganglion in Rats to Pulsed Radiofrequency Currents Activates Dorsal Horn Lamina I and II Neurons. Neurosurgery. 50 (4): 850-856. Apr. 2002.
Holsheimer, J. et al. Effects of Electrode Geometry and Combination on Nerve Fibre Selectivity in Spinal Cord Stimulation. Medical & Biological Engineering & Computing. 33 (5): 676-682. Sep. 1995.
Igarashi, T. et al. Lysis of Adhesions and Epidural Injection of Steroid/Local Anaesthetic During Epiduroscopy Potentially Alleviate Low Back and Leg Pain in Elderly Patients With Lumbar Spinal Stenosis. British Journal of Anaesthesia. 93 (2): 181-7.Aug. 2004.
Julius, David et al. Molecular Mechanisms of Nociception. Nature. 413 (6852): 203-210. Sep. 13, 2001.
Kanpolat, Yucel et al. Percutaneo Controlled Radiofrequency Trigeminal Rhizotomy for the Treatment of Idiopathic Trigeminal Neuralgia: 25-Year Experience with 1600 Patients. Neurosurgery. 48 (3): 524-534. Mar. 2001.
Kapadia, N.P. et al. Gabapentin for Chronic Pain in Spinal Cord Injury: A Case Report. Arch Phys Med Rehabil. 81 (10): 1439-41. (Abstract Only). Oct. 2000.
Kapoor, Vibhu et al. Refractory Occipital Neuralgia: Preoperative Assessment With CT-Guided Nerve Block Prior to Dorsal Cervical Rhizotomy. American Journal of Neuroradiology. 24 (10): 2105-10. Nov.-Dec. 2003.
Karai, Laszlo et al. Deletion of Vanilloid Receptor 1-Expressing Primary Afferent Neurons for Pain Control. Journal of Clinical Investigation. 113 (9): 1344-1352. May 2004.
Kline, David G. et al. Management and Results of Sciatic Nerve Injuries: a 24-Year Experience. Journal of Neurosurgery. 89 (1): 13-23. Jul. 1998.
Kobayashi, Shigeru et al. Pathology of Lumbar Nerve Root Compression Part 1: Intraradicular Inflammatory Changes Induced by Mechanical Compression. Journal of Orthopaedic Research. 22 (1): 170-179. Jan. 2004.
Kobayashi, Shigeru et al. Pathology of Lumbar Nerve Root Compression Part 2: Morphological and Immunohistochemical Changes of Dorsal Root Ganglion. Journal of Orthopaedic Research. 22 (1): 180-188. Jan. 2004.
Kocsis et al.; NR2B receptors are involved in the mediation of spinal segmental reflex potentials but not in the cumulative motoneuronal depolarization in vitro; Brain Research Bulletin, Elsevier Science Ltd.; vol. 64; No. 2; pp. 133-138; Aug. 30, 2004.
Koszewski, W. et al. [The DREZ Lesion as an Effective Treatment for Chronic Hypothetically Post-Herpetic Neuropathic Pain. Case Report and Review of Literature]. Neurol Neurochir Pol. 37 (4): 943-53. (Abstract Only). (month unavailable) 2003.
Lawrence, Stephen M. et al. Long-Term Biocompatibility of Implanted Polymer-Based Intrafascicular Electrodes. Journal of Biomedical Materials Research. Article first publ. online: 63 (5): 501-506. Jul. 31, 2002.
Lee, In-Seop et al. Characterization of Iridium Film as a Stimulating Neural Electrode. Biomaterials. 23 (11): 2375-2380. Jun. 2002.
Lew, Henry L. et al. Preganglionic Approach to Transforaminal Epidural Steroid Injections. Am. J. Phys. Med. Rehabil. 83 (5): 378. May 2004.
Lopez et al.; Excitatory and inhibitory effects of serotonin on spinal nociceptive reflexes are mediated by 5-HT2 and 5-HT1B receptors; (Database Biosis Biosciences information service, Philadelphia, PA, US, XP002567533, accession No. PREV200100573757); Abstract; (month unavailable) 2001.
Ma et al.; Enhanced excitability of dissociated primary sensory neurons after chronic compression of the dorsal root ganglion in the rat; Pain; 113(1-2); pp. 106-112; Jan. 2005.
Maher, C.O. et al. Lateral Exit-Zone Stenosis and Lumbar Radiculopathy. J Neurosurg. 90 (1 Suppl): 52-8. Jan. 1999. (Abstract Only).
Mailley, Sophie et al. Thin Film Platinum Cuff Electrodes for Neurostimulation: In Vitro Approach of Safe Neurostimulation Parameters. Bioelectrochemistry. 63(1-20: 359-364. Jun. 2004.
Masini, Michelle et al. Activated Pyrolytic Carbon Tip Pacing Leads: An Alternative to Steroid-Eluting Pacing Leads? PACE. 19(11 Pt 2): 1832-1835. Nov. 1996.
Medtronic, Inc. Equity Research dated Dec. 18, 2002 by Pacific Growth Equities pp. 1-20.
Medtronic. Analysis of Sales/Earnings-F1Q05: Many Gives and Takes in the Quarter dated Aug. 20, 2004 by Morgan Stanley pp. 1-25.
Methods of Placement of Neurostimulation Lead, Infusion, Catheter, and/or Sensor Via Peripheral Vasculature. From IP.com PriorArtDatabase—Apr. 10, 2003—#000012136 http://www.priorartdatabase.com/IPCOM/000012136.
Mond, Harry G. et al. Implantable Transveno Pacing Leads: The Shape of Things to Come. PACE. 27: 887-893. Jun. 2004.
Monti, Enrico. Peripheral Nerve Stimulation: A Percutaneous Minimally Invasive Approach. Neuromodulation. 7 (3): 193. Jul. 2004. (Abstract Only).

(56) References Cited

OTHER PUBLICATIONS

Myles et al.; Effects of different methods of peripheral nerve repair on the number and distribution of muscle afferent neurons in rat dorsal root ganglion; J Neurosurg; 77(3); pp. 457-462; Sep. 1992.

Nannini et al.; Muscle recruitment with intrafascicular electrodes; IEEE Trans on Biomedical Engineering; vol. 38; No. 8; pp. 769-776; Aug. 1991.

Naples, Gregory G. A Spiral Nerve Cuff Electrode for Peripheral Nerve Stimulation. IEEE Transactions on Biomedical Engineering. 35 (11): 905-916. Nov. 1988.

Narozny, Martin et al. Therapeutic Efficacy of Selective Nerve Root Blocks in the Treatment of Lumbar Radicular Leg Pain. Swiss Med Wkly. 131(5-6): 75-80. Feb. 2001.

Nashold, Blaine S. et al. Peripheral Nerve Stimulation for Pain Relief Using a Multicontact Electrode System. Technical note. Journal of Neurosurgery. 51 (6): 872-873. Dec. 1979.

Nashold, Blaine S. et al. Long-Term Pain Control by Direct Peripheral-Nerve Stimulation. The Journal of Bone and Joint Surgery. 64 (1): 1-10. Jan. 1982.

Neumann, Simona et al. Regeneration of Sensory Axons Within the Injured Spinal Cord Induced by Intraganglionic cAMP Elevation. Neuron. 34 (6): 885-93. Jun. 13, 2002.

Nielson, K.D. et al. Peripheral Nerve Injury From Implantation of Chronic Stimulating Electrodes for Pain Control. Surg Neurol. 5 (1): 51-3. (Abstract Only).Jan. 1976.

North, Richard B. et al. Dorsal Root Ganglionectomy for Failed Back Surgery Syndrome: A 5-Year Follow-Up Study. J Neurosurg. 74(2): 236-242. Feb. 1991.

North, Richard B. et al. Chapter 123: Current Concepts in the Neurosurgical Management of Persistent Pain (pp. 1634-1637). Operative Neurosurgical Techniques 4th Edition (Henry H. Schmidek et al. eds.). Philadelphia: W.B. Saunders Company. Publ. date: Aug. 18, 2000.

Nygaard, Oystein P. et al. The Function of Sensory Nerve Fibers in Lumbar Radiculopathy: Use of Quantitative Sensory Testing in the Exploration of Different Populations of Nerve Fibers and Dermatomes. Spine. 23 (3): 348-352. Feb. 1, 1998.

Obata, K. et al. Activation of Extracellular Signal-Regulated Protein Kinase in the Dorsal Root Ganglion Following Inflammation Near the Nerve Cell Body. Neuroscience. 126 (4): 1011-1021. Accepted Apr. 22, 2004.

Obata, Koichi, et al. Expression of Neurotrophic Factors in the Dorsal Root Ganglion in a Rat Model of Lumbar Disc Herniation. Pain. 99 (1-2): 121-132. Sep. 2002.

Olby, Natasha J. et al. Development of a Functional Scoring System in Dogs With Acute Spinal Cord Injuries. Am J Vet Res. 62(10): 1624-1628. Oct. 2001.

Parlier-Cuau, Caroline et al. Symptomatic Lumbar Facet Joint Synovial Cysts: Clinical Assessment of Facet Joint Steroid Injection After 1 and 6 Months and Long-Term Follow-Up in 30 Patients. Radiology. 210 (2): 509-513. Feb. 1999.

Pedrolli, C. et al. [Dorsolumbar Arachnoid Cysts. A Case Report]. Recenti Prog Med. 81 (11): 699-701. Nov. 1990. (Abstract Only).

Prats-Galino et al.; Representations of hindlimb digits in rat dorsal root ganglia; J Comp Neurol; 408(1); pp. 137-145; May 24, 1999.

Rodriguez, Francisco J. et al. Polyimide Cuff Electrodes for Peripheral Nerve Stimulation. Journal of Neuroscience Methods. 98 (2): 105-118. Jun. 1, 2000.

Rokugo, Tomoyuki et al. A Histochemical Study of Substance P in the Rat Spinal Cord: Effect of Transcutaneo Electrical Nerve Stimulation. J Nippon Med Sch. 69 (5): 428-433. Oct. 2002.

Romero, E. et al. Neural Morphological Effects of Long-Term Implantation of the Self-Sizing Spiral Cuff Nerve Electrode. Medical & Biological Engineering & Computing. 39 (1): 90-100. Jan. 2001.

Rongstad, K. et al. Popliteal Sciatic Nerve Block for Postoperative Analgesia. Foot Ankle Int. 17 (7): 378-82. Jul. 1996. (Abstract Only).

Ruetten, S. et al. Endoscopic Surgery of the Lumbar Epidural Space (Epiduroscopy): Results of Therapeutic Intervention in 93 Patients. Minim Invasive Neurosurg. 46 (1): 1-4. Feb. 2003. (Abstract Only).

Sairyo, K. et al. A New Endoscopic Technique to Decompress Lumbar Nerve Roots Affected by Spondylolysis. Technical Note. J Neurosurg. 98(3): 290-3. Apr. 2003. (Abstract Only).

Salame, K. et al. Surgical Treatment of Spasticity by Selective Posterior Rhizotomy 30 Years Experience. Isr Med Assoc J. 5 (8): 543-6. Aug. 2003. (Abstract Only).

Saris, S.C. et al. Sacrococcygeal Rhizotomy for Perineal Pain. Neurosurgery. 19 (5): 789-93. Nov. 1986. (Abstract Only).

Sauvage, P.J. et al. Intraspinal Synovial Cysts of the Lumbar Spine: Imaging Findings and Treatment by Percutaneo Steroid Injection. Review of 13 Cases. [Kystes Synoviaux Intraspinaux Lombaires: Imagerie et Traitement Par Infiltration. A Propos De. (month unavail.) 2000.

Schwartzman, Robert J. et al. Neuropathic Central Pain: Epidemiology, Etiology, and Treatment Options. Arch Neurol. 58 (10): 1547-1550. Oct. 2001.

Sedan, R. et al. Therapeutic Electrical Neurostimulation. French Language Society of Neurosurgery—28th Annual Congress—Athens, May 29-30, 1978. Neurochirurgie. 24: 3-8, Suppl. 1 (in French with English Summary pp. 121-125.).

Sheth, Rishi N. et al. Mechanical Hyperalgesia After an L5 Ventral Rhizotomy or an L5 Ganglionectomy in the Rat. Pain. 96: 63-72. Mar. 2002.

Siddall, Philip J. et al. Persistent Pain as a Disease Entity: Implications for Clinical Management. Anesth Analg. 99: 510-20. Aug. 2004.

Silvers, H.R. Lumbar Percutaneo Facet Rhizotomy. Spine. 15 (1): 36-40. Jan. 1990. (Abstract Only).

Slappendel, R. et al. The efficacy of Radiofrequency Lesioning of the Cervical Spinal Dorsal Root Ganglion in a Double Blinded Randomized Study: No difference Between 40 Degrees C and 67 Degrees C Treatments. Pain. 73 (2): 159-63. Nov. 1997. (Abstract Only).

Sluijter, Menno E. et al. The Effects of Pulsed Radiofrequency Fields Applied to the Dorsal Root Ganglion—A Preliminary Report. The Pain Clinic. 11 (2): 109-117. (month unavailable) 1998.

Smith, H.P. et al. Radiofrequency Neurolysis in a Clinical Model: Neuropathological Correlation. J Neurosurg. 55 (2): 246-53. Aug. 1981. (Abstract Only).

Spaic, M. et al. Drez Surgery on Con Medullaris (After Failed Implantation of Vascular Omental Graft) for Treating Chronic Pain Due to Spine (Gunshot) Injuries. Acta Neurochir(Wein). 141(12): 1309-1312. (month unavailable) 1999.

Spaic, M. et al. Microsurgical DREZotomy for Pain of Spinal Cord and Cauda Equina Injury Origin: Clinical Characteristics of Pain and Implications for Surgery in a Series of 26 Patients. Acta Neurochir (Wien). 144 (5): 453-462. May 2002.

Stanton-Hicks, M. et al. Stimulation of the Central and Peripheral Nervo System for the Control of Pain. Journal of Clinical Neurophysiology. 14 (1): 46-62. Jan. 1997.

Steinbok, P. et al. Complications After Selective Posterior Rhizotomy for Spasticity in Children With Cerebral Palsy. Pediatr Neurosurg. 28 (6): 300-13. Jun. 1998. (Abstract Only).

Stolker, Robert J. et al. The Treatment of Chronic Thoracic Segmental Pain by Radiofrequency Percutaneo Partial Rhizotomy. J Neurosurg. 80(6): 986-992. Jun. 1994.

Strait, T.A. et al. Intraspinal Extradural Sensory Rhizotomy in Patients With Failure of Lumbar Disc Surgery. J Neurosurg. 54(2): 193-6. Feb. 1981. (Abstract Only).

Taha, J.M. et al. Long-Term Results of Radiofrequency Rhizotomy in the Treatment of Cluster Headache. Headache. 35 (4): 193-6. Apr. 1995. (Abstract Only).

Taub, Arthur et al. Dorsal Root Ganglionectomy for Intractable Monoradicular Sciatica: A Series of 61 Patients. Stereotact Funct Neurosurg. 65 (1-4): 106-110. (month unavailable) 1995.

Uematsu, Sumio. Chapter 106: Percutaneo Electrothermocoagulation of Spinal Nerve Trunk, Ganglion, and Rootlets (pp. 1207-1221). Operative Neurosurgical Techniques, Indications, Methods and Results 2nd edition. (Henry H. Schmidek et al. eds.). (month unavail.) 1988.

Van Zundert, Jan et al. Pulsed Radiofrequency in Chronic Pain Management: Looking for the Best Use of Electrical Current. World Institute of Pain. 5 (2): 74-76. Jun. 2005.

(56) References Cited

OTHER PUBLICATIONS

Van De Kraats, Everine B. et al. Noninvasive Magnetic Resonance to Three-Dimensional Rotational X-Ray Registration of Vertebral Bodies for Image-Guided Spine Surgery. Spine. 29 (3): 293-297. Feb. 2004.

Van Kleef, M. et al. Effects and Side Effects of a Percutaneo Thermal Lesion of the Dorsal Root Ganglion in Patients with Cervical Pain Syndrome. Pain. 52 (1): 49-53. Jan. 1993.

Van Kleef, M. et al. Radiofrequency Lesion Adjacent to the Dorsal Root Ganglion for Cervicobrachial Pain: A Prospective Double Blind Randomized Study. Neurosurgery. 38 (6): 1127-31. Jun. 1996.

Van Kleef, Maarten et al. Chapter 160: Radiofrequency Lesions in the Treatment of Pain of Spinal Origin (pp. 1585-1599). Textbook of Stereotactic and Functional Neurosurgery 1st Edition. (Philip L. Gildenberg et al. eds.). New York: McGraw-Hill. (month unavailable) 1998.

Van Zundert, J. et al. Pulsed and Continuous Radiofrequency Current Adjacent to the Cervical Dorsal Root Ganglion of the Rat Induces Late Cellular Activity in the Dorsal Horn. Anesthesiology. 102 (1): 125-31. Jan. 2005.

Vaughan, R. Percutaneous Radiofrequency Gangliotomy in the Treatment of Trigeminal Neuralgia and Other Facial Pain. Aust N Z J Surg. 45 (2): 203-7. May 1975. (Abstract Only).

Viton, J.-M. et al. Short-Term Assessment of Periradicular Corticosteroid Injections in Lumbar Radiculopathy Associated With Disc Pathology. Neuroradiology. 40 (1): 59-62. Jan. 1998.

Viton, J.M. et al. Short-Term Evaluation of Periradicular Corticosteroid Injections in the Treatment of Lumbar Radiculopathy Associated With Disc Disease. Rev Rhum Engl Ed. 65 (3): 195-200. Mar. 1998. (Abstract Only).

Wagner, A.L. et al. Selective Nerve Root Blocks. Tech Vasc Interv Radiol. 5 (4): 194-200. Dec. 2002. (Abstract Only).

Waxman et al.; Sodium channels, excitability of primary sensory neurons, and the molecular basis of pain; Muscle Nerve; 22(9); pp. 1177-1187; Sep. 1999.

Weiner, Richard L. The Future of Peripheral Nerve Neurostimulation. Neurological Research. 22 (3): 299-304. Apr. 2000.

Weiner, Richard L. Peripheral Nerve Neurostimulation. Neurosurgery Clinics of North America. 14 (3): 401-408. Jul. 2003.

Weinstein, James et al. The Pain of Discography. Spine. 13(12):1344-8. Dec. 1988.

Wessels et al.; A rostrocaudal somatotopic organization in the brachial dorsal root ganglia of neonatal rats; Clin Neurol Neurosurg; 95 Suppl; pp. S3-11; (month unavailable) 1993.

Wessels et al.; Evidence for a rostrocaudal organization in dorsal root ganglia during development as demonstrated by intra-uterine WGA-HRP injections into the hindlimb of rat fetuses; Brain Res Dev Brain Res; 54(2); pp. 273-281; Jul. 1, 1990.

Wessels et al.; Somatotopic organization in the sensory innervation of the rat hindlimb during development, using half dorsal root ganglia as subsegmental units; Eur J Morphol; 28(2-4); pp. 394-403; (month unavailable) 1990.

Wessels et al.; The rostrocaudal organization in the dorsal root ganglia of the rat: a consequence of plexus formation?; Anat Embryol (Berl); 190(1); pp. 1-11; Jul. 1994.

Wetzel, F. Todd et al. Extradural Sensory Rhizotomy in the Management of Chronic Lumbar Radiculopathy: A Minimum 2-Year Follow-up Study. Spine. 22 (19): 2283-2291. Oct. 1, 1997.

Wetzel, F.T. Chronic Benign Cervical Pain Syndromes: Surgical Considerations. Spine. 17 (10 Suppl): S367-74. Oct. 1992. (Abstract Only).

Wetzel, F.T. et al. The Treatment of Chronic Extremity Pain in Failed Lumbar Surgery. The Role of Lumbar Sympathectomy. Spine. 17 (12): 2367-8. Dec. 1992. (Abstract Only).

White, P.F. et al. The Use of a Continuous Popliteal Sciatic Nerve Block After Surgery Involving the Foot and Ankle: Does It Improve the Quality of Recovery? Anesth Analg. 97 (5): 1303-9. Nov. 2003. (Abstract Only).

Whitworth, Louis Anthony et al. Application of Spinal Ablative Techniques for the Treatment of Benign Chronic Painful Conditions. Spine. 27 (22): 2607-2612. Nov. 15, 2002.

Wilkinson, H.A. et al. Sensory Ganglionectomy: Theory, Technical Aspects, and Clinical Experience. J Neurosurg. 95(1): 61-6. Jul. 2001. (Abstract Only).

Wong, C.B. et al. Clinical Outcomes of Revision Lumbar Spinal Surgery: 124 Patient With a Minimum of Two Years of Follow-Up. Chang Gung Med J. 25 (3): 175-82. Mar. 2002. (Abstract Only).

Wright, Robert E. et al. Neurostimulation of the L2 Dorsal Root Ganglion for Intractable Disc Pain: Description of a Novel Technique. Presented at the IFESS. (month unavailable) 1998.

Wu, Gang et al. Early Onset of Spontaneous Activity in Uninjured C-Fiber Nociceptors After Injury to Neighboring Nerve Fibers. Journal of Neuroscience. 21 (8): RC140. Apr. 15, 2001.

Yamashita, Toshihiko et al. A Quantitative Analysis of Sensory Function in Lumbar Radiculopathy Using Current Perception Threshold Testing. Spine. 27 (14): 1567-1570. Jul. 15, 2002.

Yoshida, Hirotoshi et al. Lumbar Nerve Root Compression Caused by Lumbar Intraspinal Gas: Report of Three Cases. Spine. Feb. 1, 1997, vol. 22 (3): 348-351.

Young, R.F. Chapter 161: Dorsal Rhizotomy and Dorsal Root Ganglionectomy (pp. 3442-3451). Neurological Surgery 4th Edition. Jan. 15, 1996. (Julian R. Youmans ed.). Philadelphia: W.B. Saunders Company.

Kramer et al.; U.S. Appl. No. 13/458,697 entitled "Selective stimulation to modulate the sympathetic nervous system," filed Apr. 27, 2012.

Kim et al.; U.S. Appl. No. 13/706,100 entitled "Neurostimulation Methods and Systems," filed Dec. 5, 2012.

Kishawi et al.; U.S. Appl. No. 13/753,326 entitled "Pain management with stimulation subthreshold to parasthesia," filed Jan. 29, 2013.

Dorsal Root Ganglion; www.biology-online.org/dDorsal_root_ganglion; downloaded Nov. 5, 2013; 4 pgs.

The Peripheral Nervous System; http://cnx.org/content/m44751/latest; downloaded Nov. 5, 2013; 7 pgs.

Burdulis; U.S. Appl. No. 13/975,083 entitled "Hard Tissue Anchors and Delivery Devices," filed Aug. 23, 2013.

Horsch, S. et al. Epidural spinal cord stimulation in the treatment of severe peripheral arterial occlusive disease; Annals of Vascular Surgery; 8(5): 468-74. Sep. 1994.

Mayfield Clinic for Brain & Spine; printed from http://www.mayfieldclinic.com/PE-AnatSpine.htm (last updated Jan. 2013); 7 pages.

Medicinenet.com; Definition of Lateral; printed from http://www.medterms.com/script/main/art.asp?articlekey=6226 (on Jun. 4, 2014); 3 pages.

Kishawi et al.; U.S. Appl. No. 14/615,281 entitled "Pain management with stimulation subthreshold to paresthesia," filed Feb. 5, 2015.

Imran; U.S. Appl. No. 14/633,046 entitled "Delivery devices, systems and methods for stimulating nerve tissue on multiple spinal levels," filed Feb. 26, 2015.

Burdulis; U.S. Appl. No. 14/633,060 entitled "Hard tissue anchors and delivery devices," filed Feb. 26, 2015.

* cited by examiner

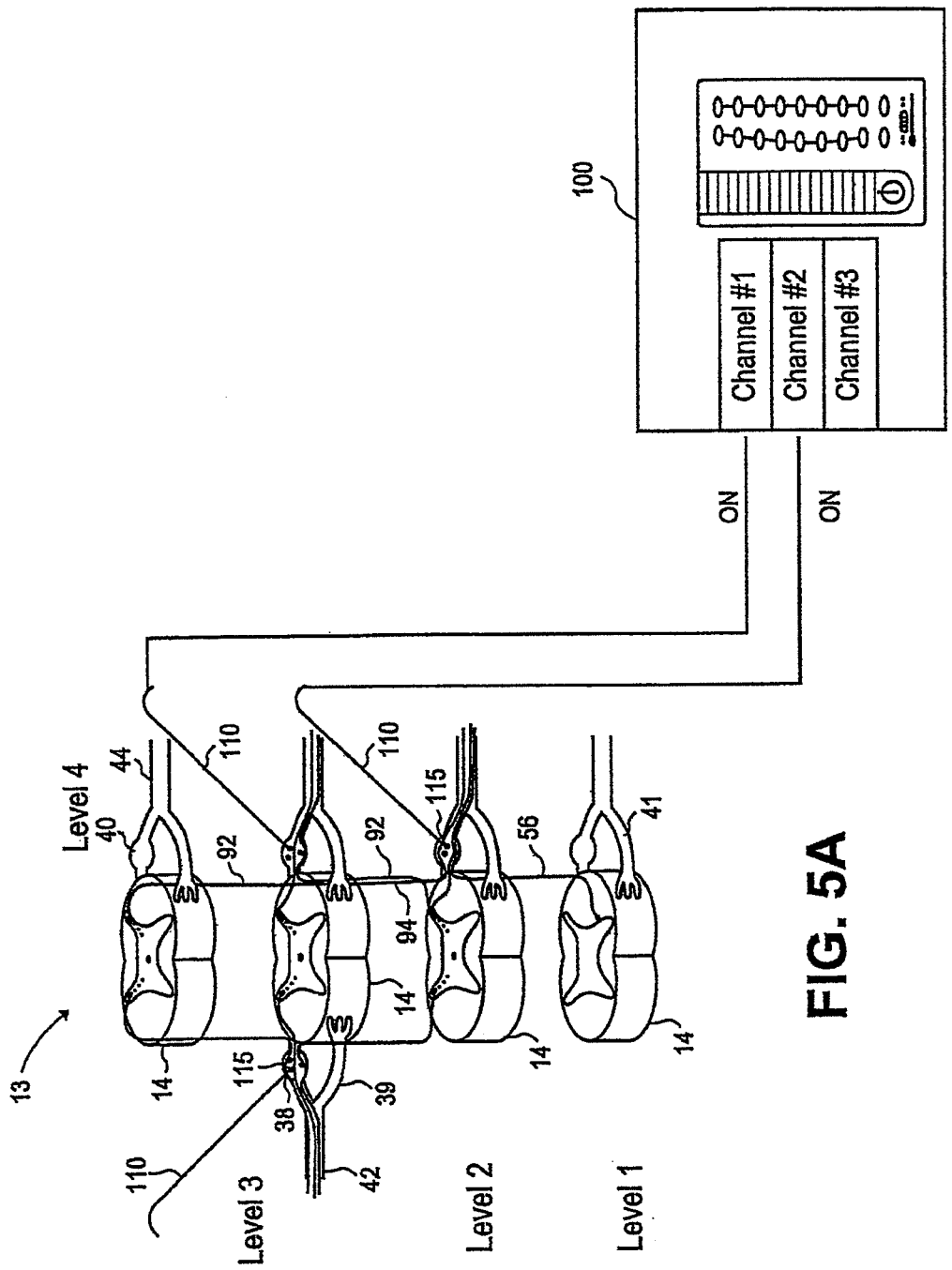

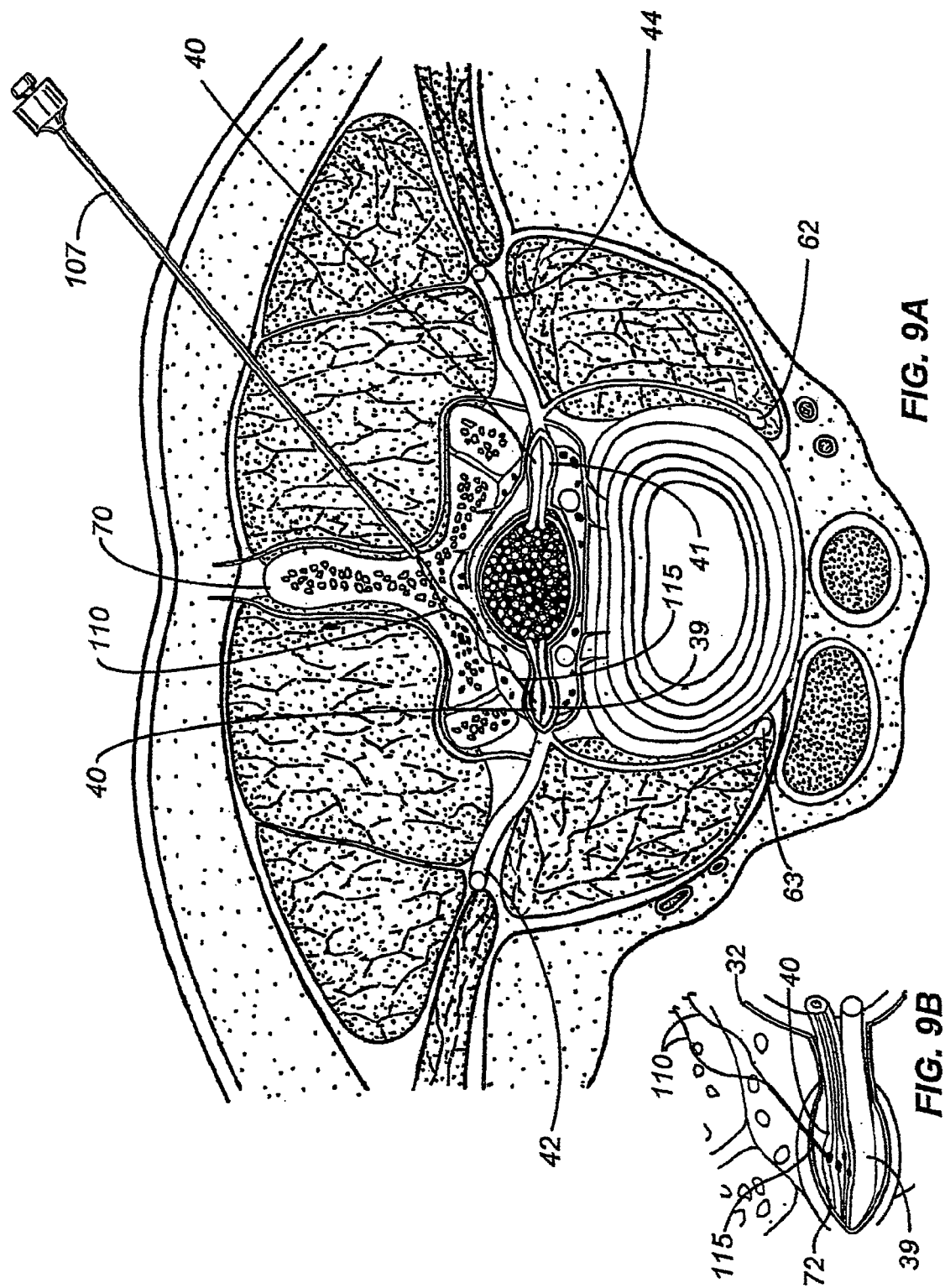

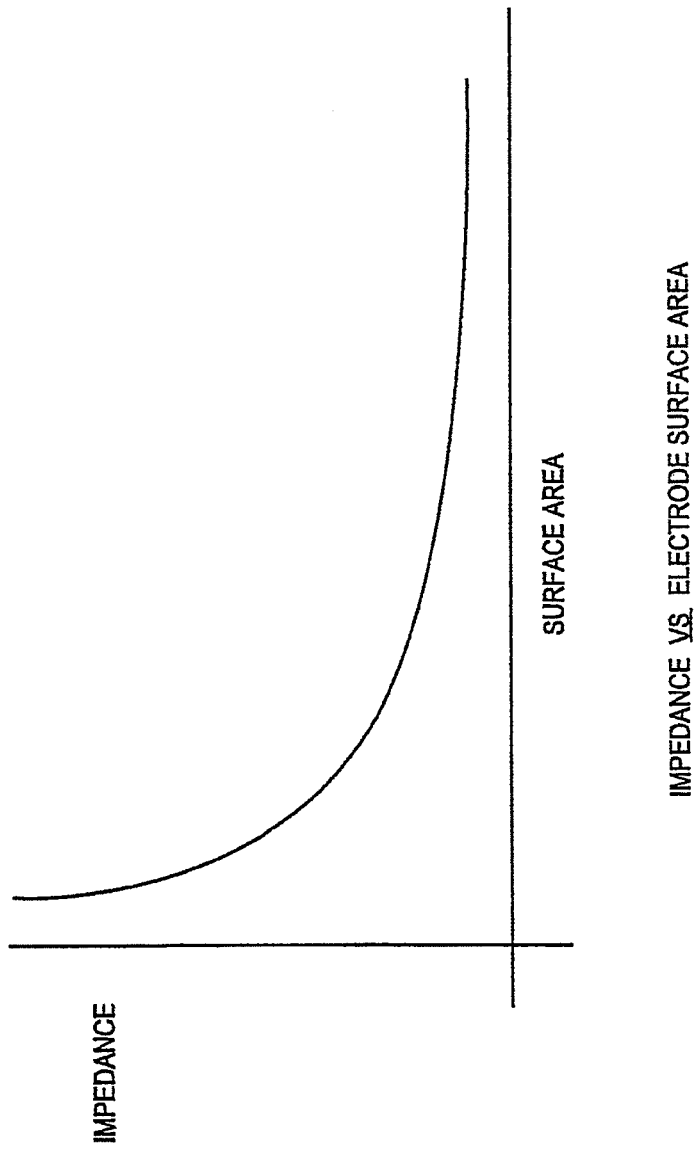

| Wire diameter (mm) | Electrode width = 0.25 mm | Electrode width = 0.5 mm |
|---|---|---|
| | Electrode Area (mm²) | Electrode Area (mm²) |
| 0.25 | 0.20 | 0.39 |
| 0.381 | 0.30 | 0.60 |
| 0.5 | 0.39 | 0.79 |
| 0.75 | 0.59 | 1.18 |
| 1 | 0.79 | 1.57 |

FIG. 15B

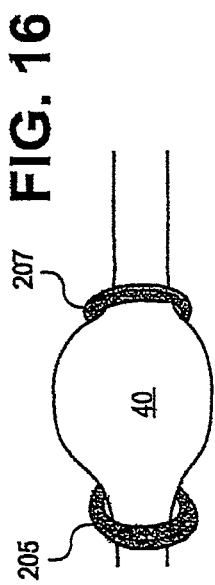
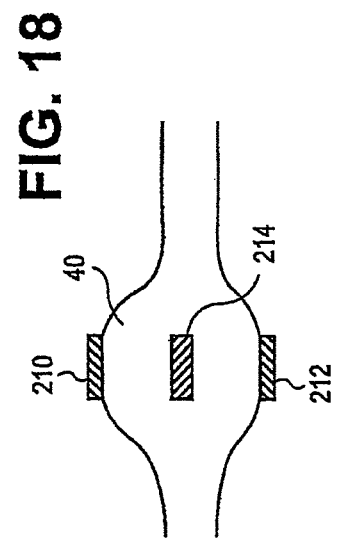
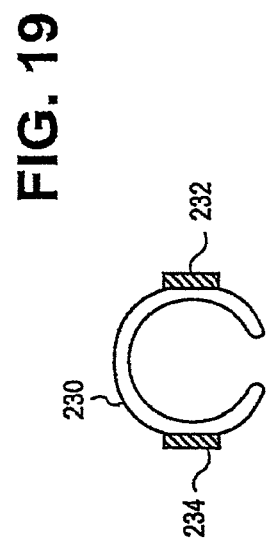
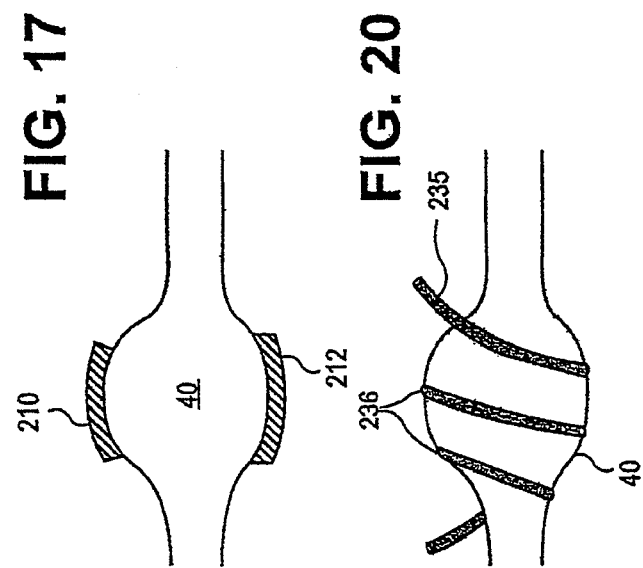

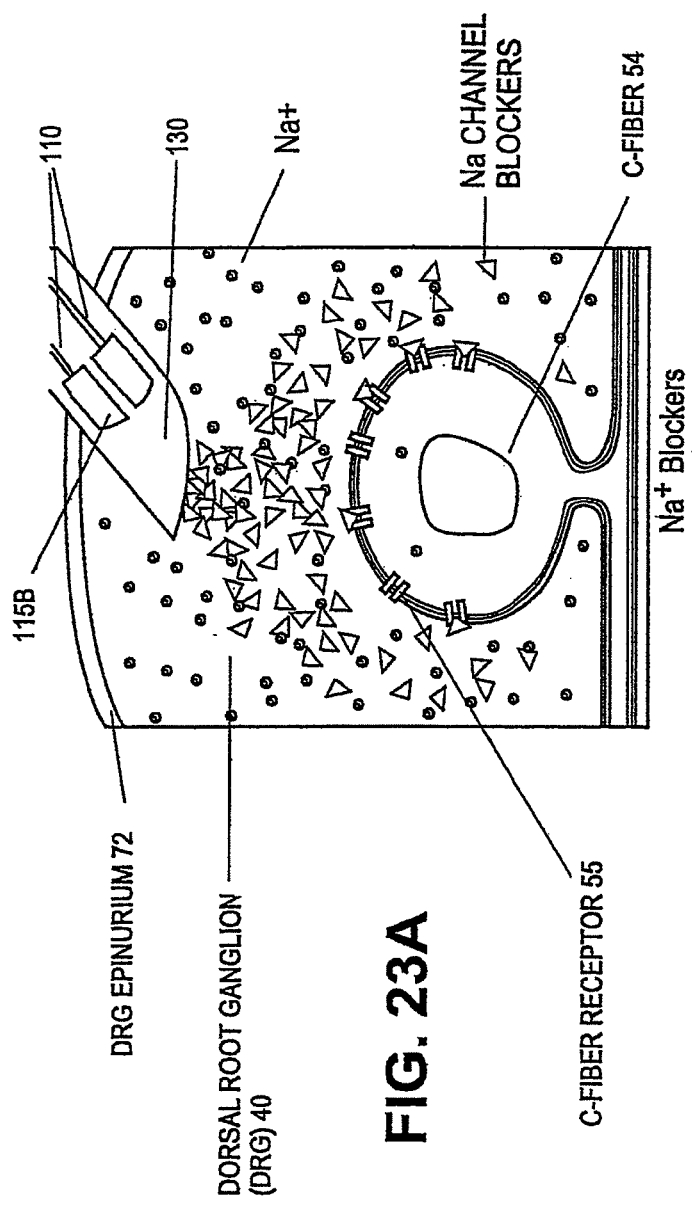
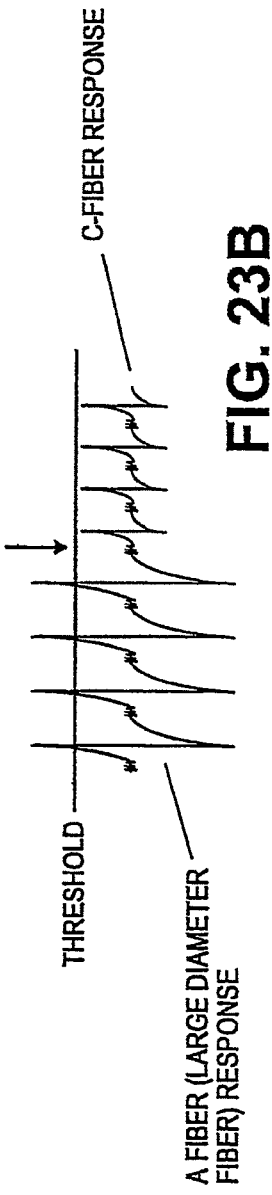
FIG. 23A
FIG. 23B

| Pharmacological Agent | Pain | | | Neuromuscular disorders | | | | | |
|---|---|---|---|---|---|---|---|---|---|
| | Neuro-pathic pain | Trigeminal neuralgia | Migraine prophylaxis | Non-epileptic myoclonus | Essential tremor | Myotonia | Myokymia (Isaacs' syndrome) | RLS | Dystonia |
| Phenytoin | ○ | ● | | | | ● | ● | | |
| Carbamazepine | ● | ● | | | | ● | ○ | | |
| Oxcarbazepine | ● | ○ | | | | | | | |
| Lamotrigine | ● | ● | ○ | | | | | | |
| Zonisamide | ○ | ○ | ○ | | | | | | |
| Valproate | ○ | ○ | ● | ● | ● | | | | |
| Topiramate | ○ | ○ | ● | | ○ | | | | |
| Gabapentin | ● | | ● | ● | ● | | | ○ | |
| Levetiracetam | ● | | ○ | ● | ● | | | | |
| Phenobarbital | | | | | ● | | | | |
| Primidone | | | | | ● | | | | |
| Benzodiazepines | ● | ● | | ● | | | | ● | ● |
| Vigabatrin | | | | | | | | | |
| Tiagabine | ● | | ● | | | | | | |

FIG. 24

METHODS FOR STIMULATING A DORSAL ROOT GANGLION

CROSS REFERENCE TO RELATED APPLICATIONS

This application is a continuation of U.S. patent application Ser. No. 12/369,706, filed Feb. 11, 2009, titled "METHODS FOR STIMULATING A DORSAL ROOT GANGLION," now Publication No. US-2009-0210041-A1, which is a divisional of U.S. patent application Ser. No. 11/222,516, filed Sep. 7, 2005, titled "METHODS FOR STIMULATING A DORSAL ROOT GANGLION," now U.S. Pat. No. 7,502,651, which claims the benefit under 35 U.S.C. 119 of U.S. Patent Application No. 60/608,357 filed Sep. 8, 2004, titled "NEUROSTIMULATION SYSTEMS AND METHODS".

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to neurostimulation methods and systems that enable more precise stimulation of the nervous system. In particular, embodiments of the present invention provide for the controlled stimulation of spinal and paraspinal nerve root ganglion. In one embodiment, the ganglion is a dorsal root ganglion (DRG) and in another embodiment the ganglion is part of the sympathetic nervous system.

BACKGROUND

Application of specific electrical energy to the spinal cord for the purpose of managing pain has been actively practiced since the 1960s. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nervous tissue. More specifically, applying particularized electrical pulses to the spinal cord associated with regions of the body afflicted with chronic pain can induce paresthesia, or a subjective sensation of numbness or tingling, in the afflicted bodily regions. This paresthesia can effectively inhibit the transmission of non-acute pain sensations to the brain.

Electrical energy, similar to that used to inhibit pain perception, may also be used to manage the symptoms of various motor disorders, for example, tremor, dystonia, spasticity, and the like. Motor spinal nervous tissue, or nervous tissue from ventral nerve roots, transmits muscle/motor control signals. Sensory spinal nervous tissue, or nervous tissue from dorsal nerve roots, transmit pain signals. Corresponding dorsal and ventral nerve roots depart the spinal cord "separately"; however, immediately thereafter, the nervous tissue of the dorsal and ventral nerve roots are mixed, or intertwined. Accordingly, electrical stimulation intended to manage/control one condition (for example, pain) often results in the inadvertent interference with nerve transmission pathways in adjacent nervous tissue (for example, motor nerves).

As illustrated in FIG. 1, prior art spinal column or spinal cord stimulators (SCS) commonly deliver electrical energy to the spinal cord through an elongate paddle 5 or epidural electrode array containing electrodes 6 positioned external to the spinal cord dura layer 32. The spinal cord dura layer 32 surrounds the spinal cord 13 and is filled with cerebral spinal fluid (CSF). The spinal cord 13 is a continuous body and three spinal levels 14 of the spinal cord 13 are illustrated. For purposes of illustration, spinal levels 14 are sub-sections of the spinal cord 13 depicting that portion where the dorsal and ventral roots join the spinal cord 13. The peripheral nerve 44 divides into the dorsal root 42 and dorsal root ganglion 40 and the ventral nerve root 41 each of which feed into the spinal cord 13. An ascending pathway 92 is illustrated between level 2 and level 1 and a descending pathway 94 is illustrated from level 2 to level 3. Spinal levels 14 can correspond to the vertebral levels of the spine commonly used to describe the vertebral bodies of the spine. For simplicity, each level illustrates the nerves of only one side and a normal anatomical configuration would have similar nerves illustrated in the side of the spinal cord 13 directly adjacent the paddle 5.

Typically, SCS are placed in the spinal epidural space. Conventional SCS systems are described in numerous patents. Additional details of the placement and use of SCS can be found, for example, in U.S. Pat. No. 6,319,241 which is incorporated herein by reference in its entirety. In general, the paddle 5 is about 8 mm wide and from 24 to 60 mm long depending upon how many spinal levels are stimulated. The illustrated electrode paddle 5 is adapted to conventionally stimulate all three spinal levels 14. These exemplary levels 1, 2 and 3 could be anywhere along the spinal cord 13. Positioning a stimulation paddle 5 in this manner results in the electrodes 6 spanning a plurality of nerves, here the dorsal root ganglion 40, the ventral root 41 and peripheral nerve 41 on multiple spinal levels.

Because the paddle 5 spans several levels the generated stimulation energy 8 stimulates or is applied to more than one type of nerve tissue on more than one level. Moreover, these and other conventional, non-specific stimulation systems also apply stimulation energy to the spinal cord and to other neural tissue beyond the intended stimulation targets. As used herein, non-specific stimulation refers to the fact that the stimulation energy is provided to all spinal levels including the nerves and the spinal cord generally and indiscriminately. Even if the epidural electrode is reduced in size to simply stimulate only one level, that electrode will apply stimulation energy indiscriminately to everything (i.e., all nerve fibers and other tissues) within the range of the applied energy 8. Moreover, larger epidural electrode arrays may alter cerebral spinal fluid (CSF) flow thus further altering local neural excitability states.

Another challenge confronting conventional neurostimulation systems is that since epidural electrodes must apply energy across a wide variety of tissues and fluids (i.e., CSF fluid amount varies along the spine as does pia matter thickness) the amount of stimulation energy needed to provide the desired amount of neurostimulation is difficult to precisely control. As such, increasing amounts of energy may be required to ensure sufficient stimulation energy reaches the desired stimulation area. However, as applied stimulation energy increases so too increases the likelihood of deleterious damage or stimulation of surrounding tissue, structures or neural pathways.

To achieve stimulation the targeted tissue, the applied electrical energy should be properly defined and undesired energy application to non-targeted tissue be reduced or avoided. An improperly defined electric field may not only be ineffective in controlling/managing the desired condition(s) but may also inadvertently interfere with the proper neural pathways of adjacent spinal nervous tissue. Accordingly, a need exists for stimulation methods and systems that enable more precise delivery of stimulation energy.

SUMMARY OF THE DISCLOSURE

In one embodiment, there is provided a method of stimulating a dorsal root ganglion by implanting an electrode in proximity to the dorsal root ganglion; and activating the electrode to stimulate a portion of the dorsal root ganglion, or activating the electrode to stimulate substantially only the dorsal root ganglion.

In another embodiment, there is provided a method of stimulating a nerve root ganglion by implanting an electrode into the nerve root ganglion; and activating the electrode to stimulate the nerve root ganglion.

In another embodiment, there is provided, a method of stimulating the spinal cord by implanting an electrode into the spinal cord; and providing stimulation energy to spinal cord fibers using the electrode.

In another embodiment, there is provided a method of modulating nervous tissue within a dorsal root ganglion by implanting an electrode within a dorsal root ganglion; and providing electrical stimulation from the electrode to stimulate neural tissue within the dorsal root ganglion.

In another embodiment, there is provided a method of modulating a neural pathway in the sympathetic nervous system by stimulating a spinal dorsal root ganglion upstream of at least one ganglion of the sympathetic nerve chain to influence a condition associated with the at least one ganglion of the sympathetic nerve chain.

In yet another embodiment, there is provided a neurostimulation system having an electrode adapted for stimulation of only a nerve root ganglion; a signal generator coupled to the electrode; and a controller to control the output of the signal generator.

In yet another embodiment, there is provided a method of stimulating the spinal cord by piercing the spinal dura matter; and placing an electrode into contact with a portion of the intra-madullary of the spinal cord.

In yet another embodiment, there is a method of stimulating the nervous system by implanting an electrode such that when the electrode is activated, the electrode stimulates only a nerve root ganglion.

In yet another embodiment, there is provided a method of stimulating neural tissue to treat a condition including stimulating an electrode implanted to stimulate only a dorsal root ganglion on a spinal level wherein the stimulation treats the condition.

In yet another embodiment, there is provided a pulse generator, comprising at least one switch connected to at least one implantable electrode having an impedance greater than 2,500 ohms; a DC-DC converter adapted to provide a stimulation signal to the at least one implantable electrode; and a controller configured to control the output of the DC-DC converter.

In yet another embodiment, there is provided a stimulation component, comprising a proximal connector; a distal electrode configured to be implanted within the body at a stimulation site; an electrical lead connected to the proximal connector and the distal electrode; a strain relief mechanism in proximity to the stimulation site; and a fixation element adapted to reduce the amount of movement of the electrical lead proximal to a fixation point in an anatomical structure proximal to the stimulation site.

In another embodiment, there is provided a stimulation component, comprising a proximal connector; a distal electrode configured to be implanted within the body at a stimulation site; an electrical lead connected to the proximal connector and the distal electrode; a strain relief mechanism in proximity to the stimulation site; and a fixation element adapted to reduce the amount of movement of the electrical lead proximal to a fixation point in an anatomical structure proximal to the stimulation site.

In another embodiment, there is provided a stimulation system, comprising a pulse generator; an electrode connector having a flexible, elongate body with a proximal end electrically connected to the pulse generator and a distal end adapted to connect to a microelectrode lead, wherein the microelectrode lead connects proximally to the electrode connector distal end and has a distal microelectrode electrically connected to the pulse generator.

In yet another embodiment, there is provided a stimulation system, comprising a battery; a pulse generator separate from the battery; an electrical connection between the battery and the pulse generator; a microelectrode lead connected proximally to the pulse generator and distally to a microelectrode.

In yet another embodiment, there is provided a neurostimulation component, comprising a body having a distal end and a proximal end and a length selected to implant the body within a targeted neural tissue; a tip on the distal end of the body adapted to pierce through the targeted neural tissue; and an electrode structure positioned on the body adapted to neurostimulate only the targeted neural tissue.

In yet another embodiment, there is provided a method of neurostimulating targeted neural tissue, comprising implanting an electrode in a position adapted to neurostimulate only targeted neural tissue; and providing a controlled stimulation signal from a signal generator coupled to the electrode.

BRIEF DESCRIPTION OF THE DRAWINGS

A better understanding of the features and advantages of the various embodiments of the present invention will be obtained by reference to the following detailed description and the accompanying drawings of which:

FIG. 5A illustrates a single electrode per level, two level activation pattern

FIG. 9A is a section view of a spinal level with an electrode being implanted into a dorsal root ganglia using an approach that crosses a medial line of the level of interest and FIG. 9B is an enlarged view of the DRG in FIG. 9A with an implanted electrode;

FIG. 15A is a chart illustrating the relationship between impedance and electrode surface area;

FIG. 15B is a chart illustrating representative electrode areas for stimulation components of several embodiments of the invention;

FIGS. 16-20 are various alternative electrode embodiments;

FIG. 23A illustrates a combination stimulation and agent delivery electrode that provides the threshold adjustment illustrated in FIG. 23B;

FIG. 24 is a table listing several exemplary pharmacological agents and their uses;

DETAILED DESCRIPTION

Figure 1:
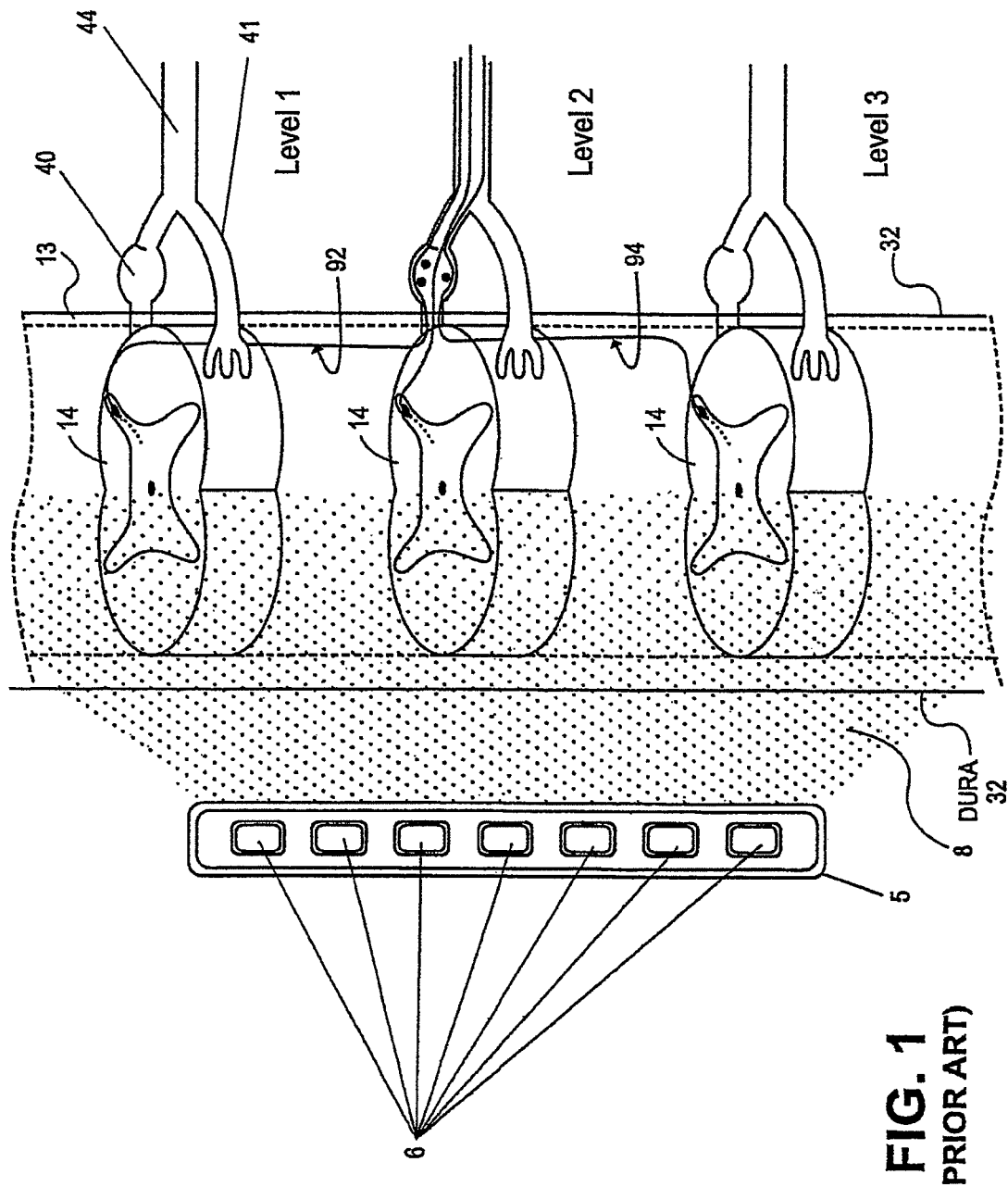
FIG. 1 illustrates a conventional epidural electrode array positioned external to and stimulating a portion of the spinal cord.

Embodiments of the present invention provide novel stimulation systems and methods that enable direct and specific neurostimulation techniques. For example, there is provided a method of stimulating a nerve root ganglion comprising implanting an electrode into the nerve root ganglion and activating the electrode to stimulate the nerve root ganglion. As discussed in greater detail below, the nerve root ganglion may be a dorsal root ganglion in some embodiments while in other embodiments the nerve root ganglion may be a nerve root ganglion in the sympathetic nervous system or other ganglion or tissue. In some embodiments, implanting the electrode includes forming an opening in the epinurium of the root ganglion and passing the electrode through the opening and into the interior space or interfascicular space of the ganglion.

In other embodiments, portions of an electrode body pass completely through a ganglion while maintaining an active electrode area appropriately positioned to deliver stimulation energy to the ganglion. In still other embodiments of the microelectrodes and stimulation systems of the invention, the size, shape and position of a microelectrode and the stimulation pattern or algorithm is chosen to stimulated targeted neural tissue and exclude others. In other additional embodiments, the electrode stimulation energy is delivered to the targeted neural tissue so that the energy dissipates or attenuates beyond the targeted tissue or region.

Once the electrode is in place on, in or adjacent the desired nerve root ganglion, the activating step proceeds by coupling a programmable electrical signal to the electrode. In one embodiment, the amount of stimulation energy provided into the nerve ganglion is sufficient to selectively stimulate neural tissue. In a specific embodiment, the stimulation energy provided only stimulates neural tissue within the targeted DRG. Alternatively, the stimulation energy beyond the DRG is below a level sufficient to stimulate, modulate or influence nearby neural tissue.

In an example where the electrode is implanted into a dorsal root ganglion, the stimulation level may be selected as one that preferentially activates myelinated, large diameter fibers (such as $A\beta$ and $A\alpha$ fibers) over unmyelinated, small diameter fibers (such as c-fibers). In additional embodiments, the stimulation energy used to activate an electrode to stimulate neural tissue remains at an energy level below the level to used ablate, lesion or otherwise damage the neural tissue. For example, during a radiofrequency percutaneous partial rhizotomy, an electrode is placed into a dorsal root ganglia and activated until a thermolesion is formed (i.e., at an electrode tip temperature of about 67° C.) resulting in a partial and temporary sensory loss in the corresponding dermatome. In one embodiment, the stimulation energy levels applied to a DRG remain below the energy levels used during thermal ablation, RF ablation or other rhizotomy procedures.

Tissue stimulation is mediated when current flow through the tissue reaches a threshold, which causes cells experiencing this current flow to depolarize. Current is generated when a voltage is supplied, for example, between two electrodes with specific surface area. The current density in the immediate vicinity of the stimulating electrode is an important parameter. For example, a current of 1 mA flowing through a 1 mm$^2$ area electrode has the same current density in its vicinity as 10 mA of current flowing through a 10 mm$^2$ area electrode, that is 1 mA/mm$^2$. In this example, cells close to the electrode surface experience the same stimulation current. The difference is that the larger electrode can stimulate a larger volume of cells and the smaller electrode can stimulate a smaller volume of cells in proportion to their surface area.

In many instances, the preferred effect is to stimulate or reversibly block nervous tissue. Use of the term "block" or "blockade" in this application means disruption, modulation, and inhibition of nerve impulse transmission. Abnormal regulation can result in an excitation of the pathways or a loss of inhibition of the pathways, with the net result being an increased perception or response. Therapeutic measures can be directed towards either blocking the transmission of signals or stimulating inhibitory feedback. Electrical stimulation permits such stimulation of the target neural structures and, equally importantly, prevents the total destruction of the nervous system. Additionally, electrical stimulation parameters can be adjusted so that benefits are maximized and side effects are minimized.

Figure 2A:
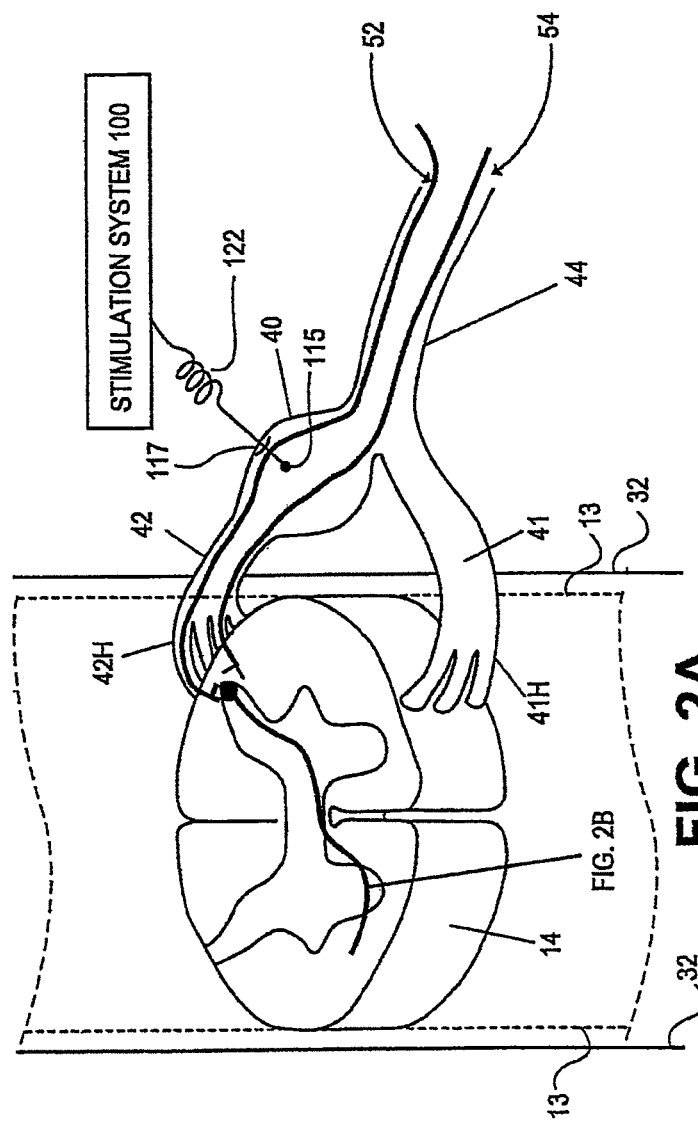
FIG. 2A illustrates an embodiment an electrode implanted into a spinal dorsal root ganglion.
Figure 2B:
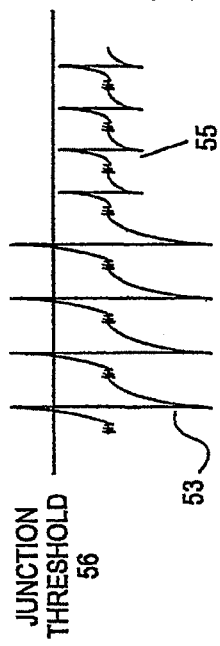
FIG. 2B illustrates how selective stimulation techniques of FIG. 2A may raise a response threshold.

FIG. 2A illustrates an embodiment of a stimulation system 100 of the present invention in place with an electrode 115 implanted into a spinal dorsal root ganglion 40. For purposes of illustration, spinal level 14, a sub-section of the spinal cord 13, is used to depict where the dorsal root 42 and ventral root 41 join the spinal cord 13, indicated by 42H and 41H respectively. The peripheral nerve 44 divides into the dorsal root 42 and dorsal root ganglion 40 and the ventral nerve root 41. For simplicity, the nerves of only one side are illustrated and a normal anatomical configuration would have similar nerves positioned on the other side. The spinal dura layer 32 surrounds the spinal cord 13 and is filled with cerebral spinal fluid (CSF). For clarity, the spinal dura layer or dura mater 32 alone is used to represent the three spinal meninges—the pia mater, the arachnoid mater and the dura mater—that surround and protect the spinal cord 13.

Note that the electrode 115 is implanted medial to the peripheral nerve 44 after the nerve root splits into the ventral nerve 41 containing the motor nerves and the dorsal root 42 containing the sensory nerves. The electrode 115 is also implanted lateral of the dura layer 32. The advantageous placement of one or more electrode embodiments of the present invention enables selective stimulation of neural tissue, such as a nerve root ganglion, without stimulation of surrounding neural tissue. In this example, a dorsal root ganglion 40 is stimulated with little or imperceptible amounts of stimulation energy provided to the motor nerves within the ventral nerve root 44, portions of the spinal cord 13, spinal level 14, or the peripheral nerve 44. Embodiments of the present invention are particularly well suited for providing pain control since the sensory fibers running through the dorsal root ganglion 40 may be specifically targeted. Advantageously, embodiments of the present invention may neuromodulate one or more the dorsal root ganglia for pain control without influencing surrounding tissue.

The stimulation system 100 includes a pulse generator that provides stimulation energy in programmable patterns adapted for direct stimulation of neural tissue using small area, high impedance microelectrodes. The level of stimulation provided is selected to preferentially stimulate the Aβ and Aα fibers 52 over the c-fibers 54. Stimulation energy levels used by embodiments of the present invention utilize lower stimulation energy levels than conventional non-direct, non-specific stimulations systems because the electrode 115 is advantageously placed on, in or about a dorsal root ganglion 40. Based on conventional gate control theory, it is believed that by stimulating of the faster transmitting Aβ and Aα fibers 52 by the stimulation methods of the present invention, the signal 53 from the fibers 52 will release opiates at the junction of the dorsal root 42 and the spinal cord 13. This release raises the response threshold at that junction (elevated junction threshold 56). The later arriving c-fiber signal 55 remains below the elevated junction threshold 56 and goes undetected.

Accordingly, some embodiments of the present invention provide selective stimulation of the spinal cord, peripheral nervous system and/or one or more dorsal root ganglia. As used herein in one embodiment, selective stimulation means that the stimulation substantially only neuromodulates or neurostimulates a nerve root ganglion. In one embodiment, selective stimulation of a dorsal root ganglion leaves the motor nerves unstimulated or unmodulated. In addition, in other embodiments, selective stimulation can also mean that within the nerve sheath, the A-myelinated fibers are preferentially stimulated or neuromodulated as compared to the c-unmyelinated fibers. As such, embodiments of the present invention advantageously utilize the fact that A-fibers carry neural impulses more rapidly (almost twice as fast) as c-fibers. Some embodiments of the present invention are adapted to provide stimulation levels intended to preferentially stimulate A-fibers over c-fibers.

Figure 21:
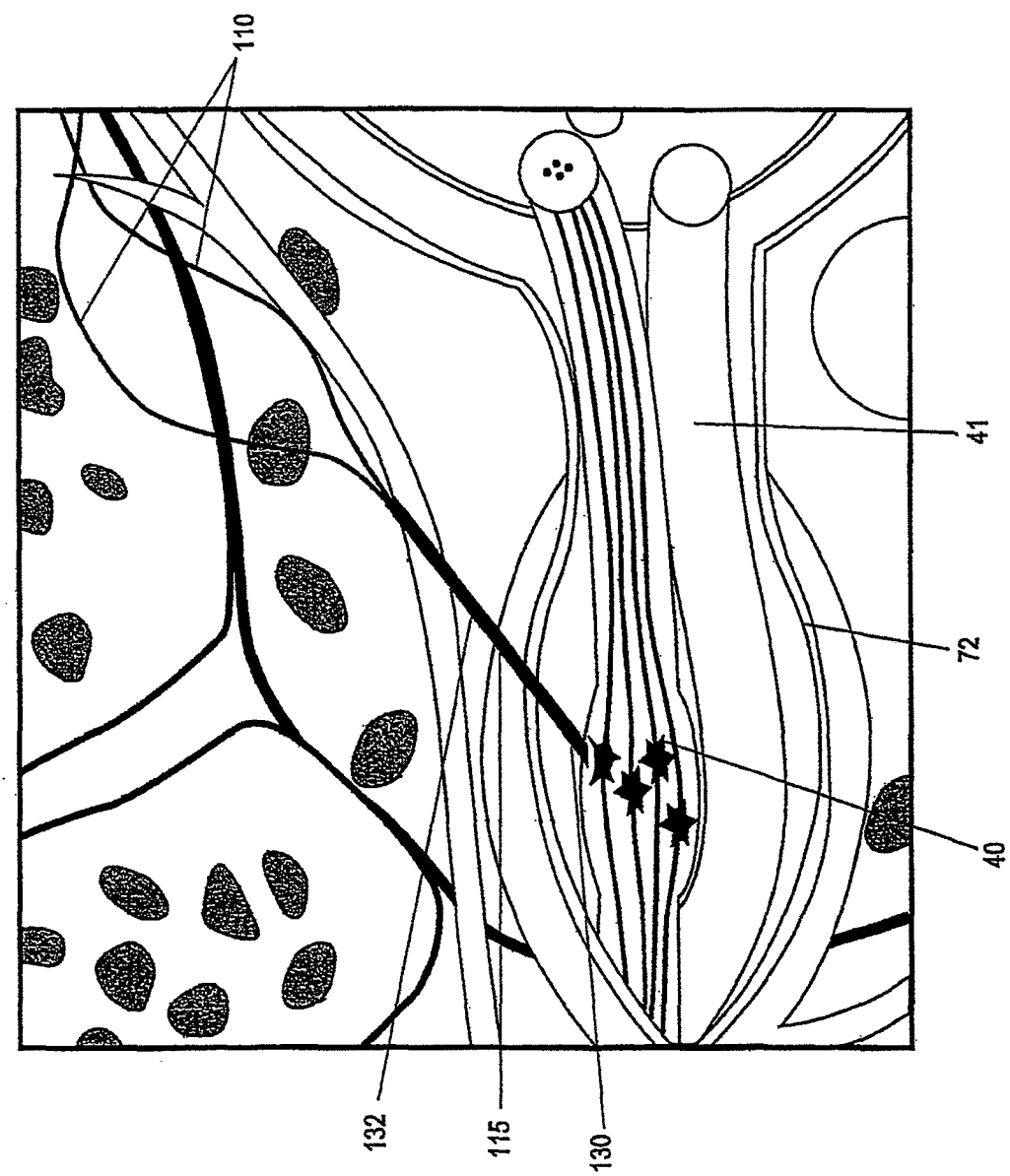
FIG. 21 illustrates a coated electrode implanted into a DRG.

In additional embodiments, selective stimulation can also mean that the electrode (including an electrode coated with or adapted to deliver a pharmacological agent, e.g., FIGS. 21, 23A, C and D) is in intimate contact with the tissue or other nervous system component that is the subject of stimulation. This aspect recognizes our advantageous use of electrode placement. In specific illustrative embodiments discussed further below, one or more stimulation electrodes are placed (1) against or in contact with the outer sheath of a nerve root ganglion; (2) within a nerve root ganglion; (3) within the root ganglion interfascicular space; (4) in contact with a portion of the spinal cord; (5) in a position that requires piercing of the epidural space, the dura, nerve root epinurium or a portion of the spinal cord; (6) in contact with a portion of the sympathetic nervous system or (7) in contact with neural tissue targeted for direct stimulation.

Moreover, selective stimulation or neuromodulation concepts described herein may be applied in a number of different configurations. Unilateral (on or in one root ganglion on a level), bi-lateral (on or in two root ganglion on the same level), unilevel (one or more root ganglion on the same level) or multi-level (at least one root ganglion is stimulated on each of two or more levels) or combinations of the above including stimulation of a portion of the sympathetic nervous system and one or more dorsal root ganglia associated with the neural activity or transmission of that portion of the sympathetic nervous system. As such, embodiments of the present invention may be used to create a wide variety of stimulation control schemes, individually or overlapping, to create and provide zones of treatment.

Figure 3A:
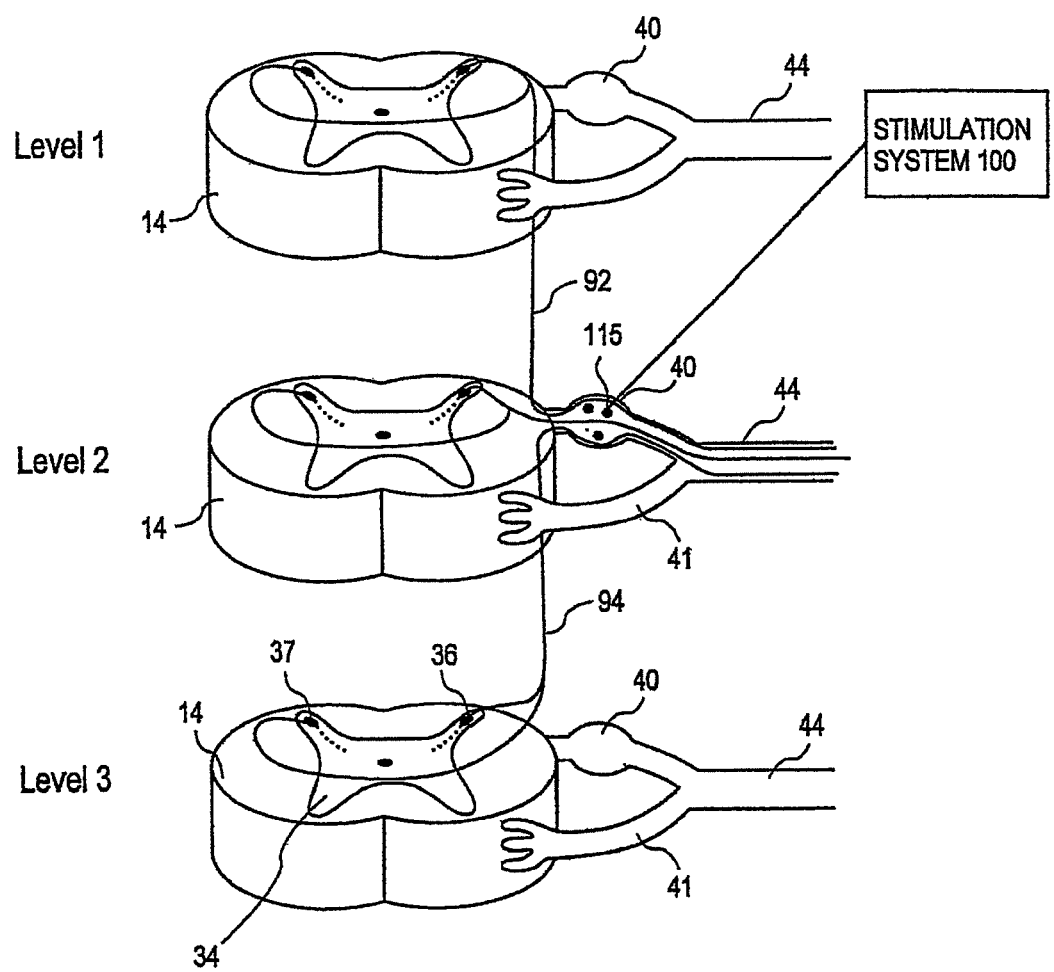
FIG. 3A illustrates a stimulation system with an electrode embodiment of the present invention implanted into a dorsal root ganglion (DRG) of a spinal level.

FIG. 3A illustrates an embodiment of a stimulation system 100 of the present invention with an electrode 115 implanted into a dorsal root ganglion (DRG) 40. The figure illustrates three representative spinal levels 14 (i.e., spinal levels 1-3) of the spinal cord 13. The peripheral nerve 44 feeds into the dorsal root ganglion 40 and the ventral nerve root 41 each of which feed into the spinal cord 13. The dorsal horns 37, 36 are also indicated. For clarity, the dura 32 and complete spinal cord 13 are not illustrated but are present as described elsewhere in this application and as occur in human anatomy. These exemplary levels 1, 2 and 3 could be anywhere along the spinal cord 13. For simplicity, each level illustrates the nerves of only one side.

Using level 2 as a reference, an ascending pathway 92 is illustrated between level 2 and level 1 and a descending pathway 94 is illustrated from level 2 to level 3. Application of stimulation energy or signals to the DRG 40 in level 2 may be used to block signals progressing upstream from level 2 towards the path/pathways 92. Moreover, modulation applied to portions of level 2 but may also be used to effectively block the neuron paths/pathways from another level (here, alternatively using levels 1 and/or 3) from reaching the brain. As such, application of stimulation to the level 2 DRG 40 using an embodiment of an apparatus and/or method of the present invention may advantageously provide an effective block of intrasegment pain pathways as well. It is to be appreciated that while three continuous levels are illustrated, some embodiments of the present invention may be used to stimulate 2 or more adjacent levels and still other embodiments may be used to stimulate 2 or more non-adjacent levels, or combinations thereof.

Figure 3B:
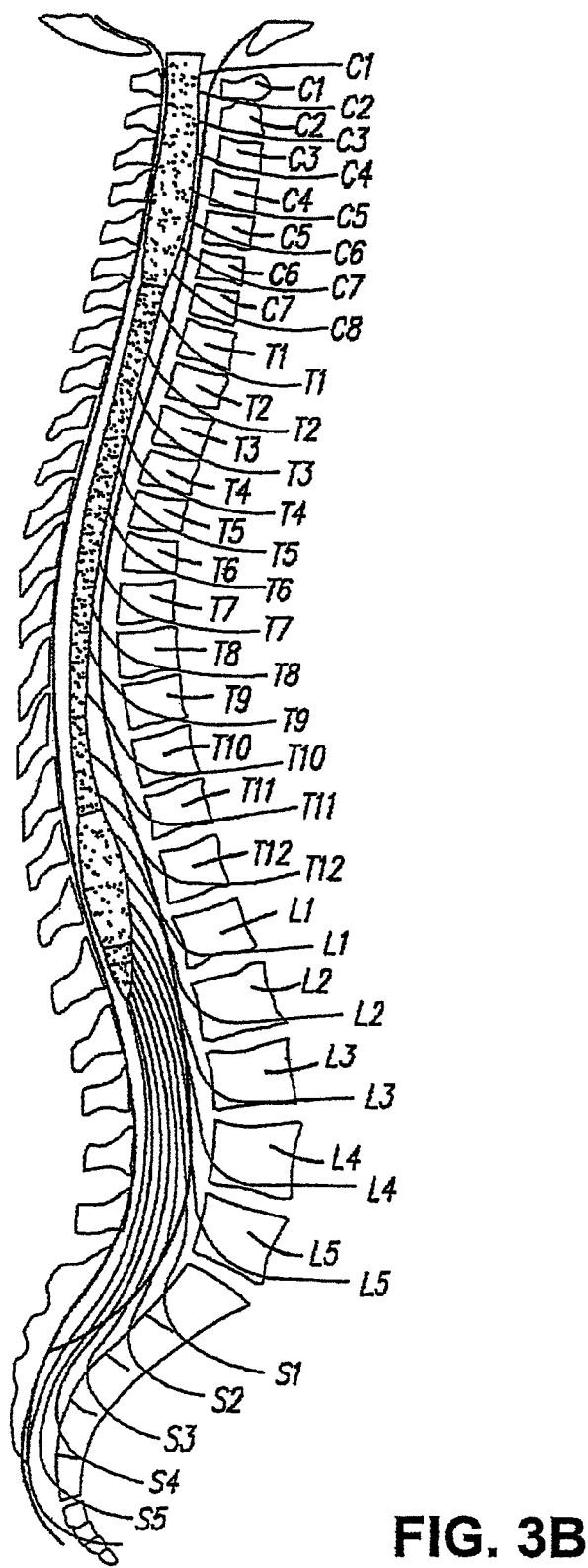
FIG. 3B relates the spinal nerve roots to their respective vertebral spinal levels.
Figure 3C:
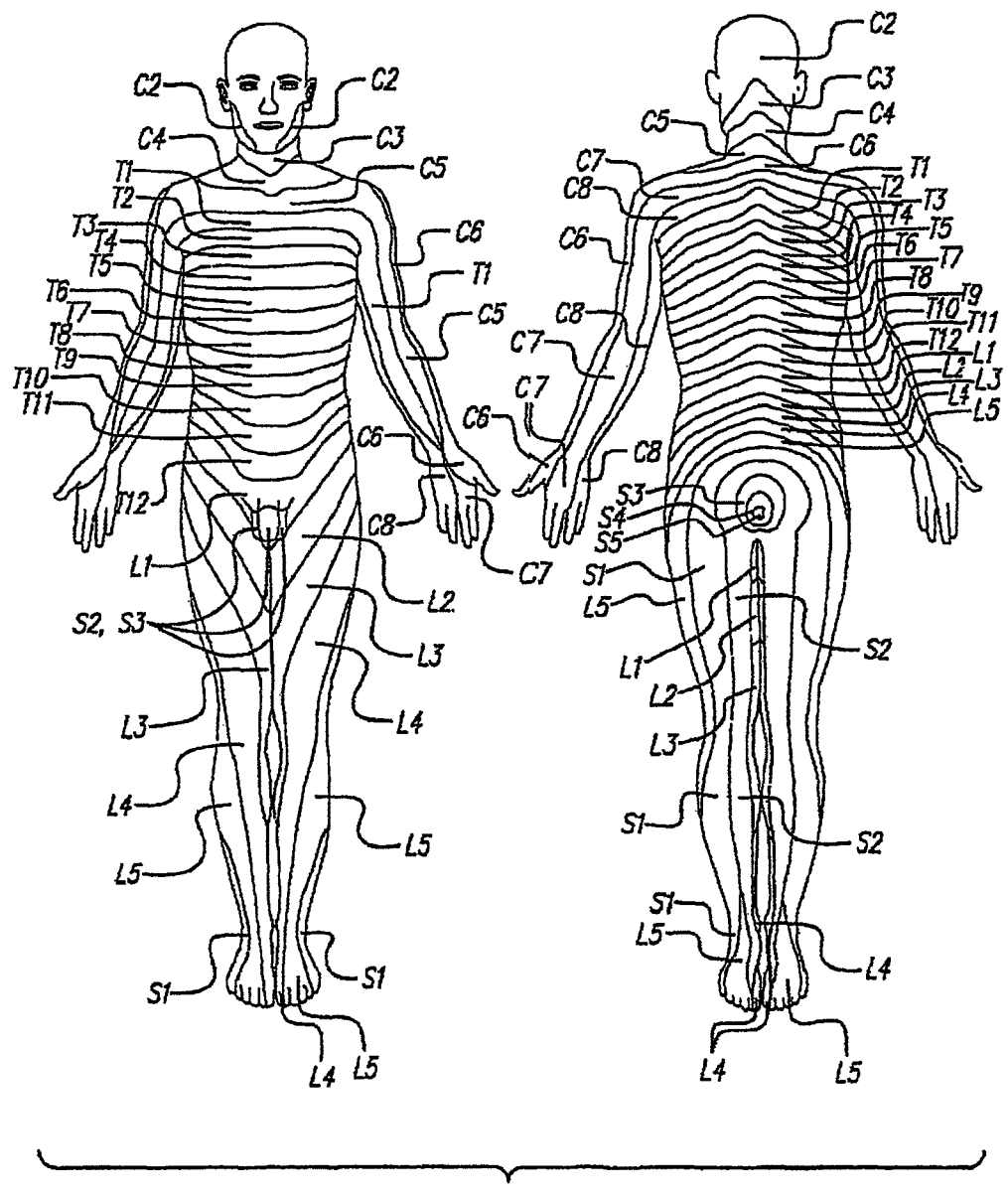
FIG. 3C illustrates the various dermatomes of the body related to their respective nerve roots in FIG. 3B.

FIG. 3B relates the spinal nerve roots to their respective vertebral spinal levels. The letter C designates nerves and vertebrae in the cervical levels. The letter T designates vertebrae and nerves in the thoracic levels. The letter L designates vertebrae and nerves in the lumbar levels. The letter S designates vertebrae and nerves in the sacral levels. FIG. 3C illustrates the various dermatomes of the body related to their respective nerve roots using the designations in FIG. 3B.

FIGS. 4-7 illustrate one embodiment of a stimulation system activated under a variety of control conditions to provide different levels and degrees of pain control. FIGS. 4A, 5A, 6A and 7A all illustrate the stimulation system in various degrees of activation. FIGS. 4B, 5B, 6B and 7B illustrate a correspondingly influenced dermatome.

FIGS. 4A, 5A, 6A and 7A illustrate a stimulation system 100 having 3 electrodes 115 implanted into dorsal root ganglia 40 on two adjacent spinal levels. For simplicity, each spinal level illustrates a dorsal root ganglion 40, a ventral root 41 and a peripheral nerve 44. The exception is spinal level 3 that illustrates an additional dorsal root ganglion 38, a ventral root 39 and a peripheral nerve 42. The three electrodes 115 are designated channels 1, 2 and 3 by the controller 106. Each electrode is activated to provide modulation energy or signals under the control of the controller 106. Exemplary electrodes for implantation into a nerve root ganglion are further described with regard to FIGS. 12A-13B. Level 3 is an example of bilateral electrode placement and level 2 is an example of unilateral electrode placement. As such, the illustrated embodiment is a multi-level, unilateral and bi-lateral stimulation system. Stimulation energy is provided by a pulse generator (not illustrated but described in greater detail below in FIGS. 26-29) under control of a suitable neurostimulation controller 106. Those of ordinary skill will recognize that any of a wide variety of known neurostimulation controllers may be used. Not illustrated in this view but present in the system are suitable connections between the various electrodes 115, electrode leads 110 and the controller 106. In the illustrations that follow, a line connecting the electrode lead 110 to the controller 106 indicates "stimulation on" communication from the controller 106 to one electrode 115 (see FIG. 4A) or more than one electrode 115 (see FIG. 5A).

A signal of "stimulation on" indicates any of a wide variety of stimulation patterns and degrees of stimulation. The "stimulation on" signal may be an oscillating electrical signal may be applied continuously or intermittently. Furthermore, if an electrode is implanted directly into or adjacent to more than one ganglion, the oscillating electrical signal may be applied to one electrode and not the other and vice versa. One can adjust the stimulating poles, the pulse width, the amplitude, as well as the frequency of stimulation and other controllable electrical and signally factors to achieve a desired modulation or stimulation outcome.

The application of the oscillating electrical signal stimulates the area of the nerve chain where the electrode 115 is placed. This stimulation may either increase or decrease nerve activity. The frequency of this oscillating electrical signal is then adjusted until the symptoms manifest by physiological disorder being treated has been demonstrably alleviated. This may step may be performed using patient feedback, sensors or other physiological parameter or indication. Once identified, this frequency is then considered the ideal frequency. Once the ideal frequency has been determined, the oscillating electrical signal is maintained at this ideal frequency by storing that frequency in the controller.

In one specific example, the oscillating electrical signal is operated at a voltage between about 0.5 V to about 20 V or more. More preferably, the oscillating electrical signal is operated at a voltage between about 1 V to about 30 V or even 40V. For micro stimulation, it is preferable to stimulate within the range of 1V to about 20V, the range being dependent on factors such as the surface area of the electrode. Preferably, the electric signal source is operated at a frequency range between about 10 Hz to about 1000 Hz. More preferably, the electric signal source is operated at a frequency range between about 30 Hz to about 500 Hz. Preferably, the pulse width of the oscillating electrical signal is between about 25 microseconds to about 500 microseconds. More preferably, the pulse width of the oscillating electrical signal is between about 50 microseconds to about 300 microseconds.

The application of the oscillating electrical signal may be provided in a number of different ways including, but not limited to: (1) a monopolar stimulation electrode and a large area non-stimulating electrode return electrode; (2) several monopolar stimulating electrodes and a signal enlarge area non-stimulating return electrode; (3) a pair of closely spaced bi-polar electrodes; and (4) several pairs of closely spaced bi-polar electrodes. Other configurations are possible. For example, the stimulation electrode(s) of the present invention may be used in conjunction with another non-stimulating electrode—the return electrode—or a portion of the stimulation system may be adapted and/or configured to provide the functionality of a return electrode. Portions of the stimulation system that may be adapted and/or configured to provide the functionality of the return electrode include, without limitation, the battery casing or the pulse generator casing.

Figure 4A:
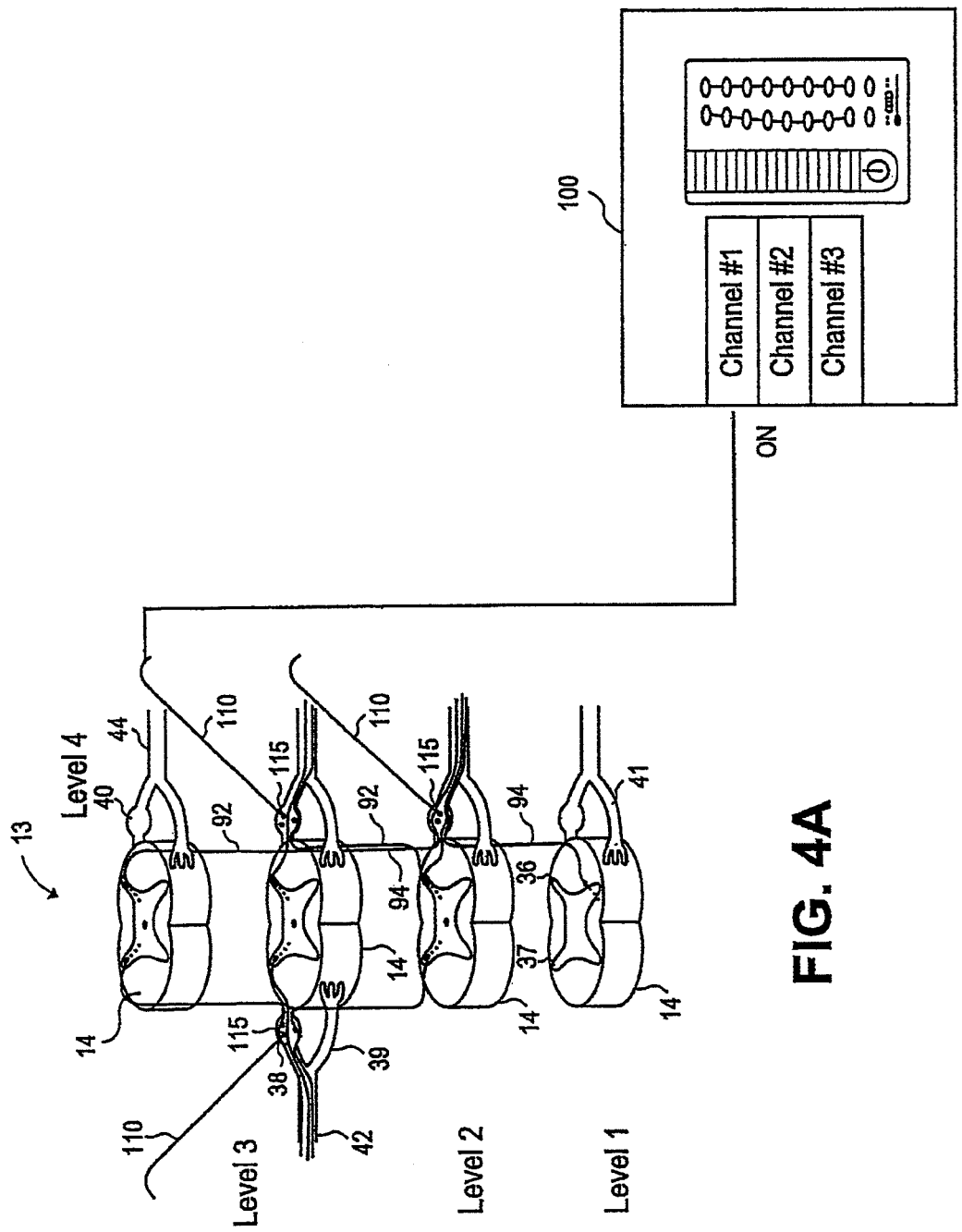
FIG. 4A illustrates a single electrode, single level activation pattern
Figure 4B:
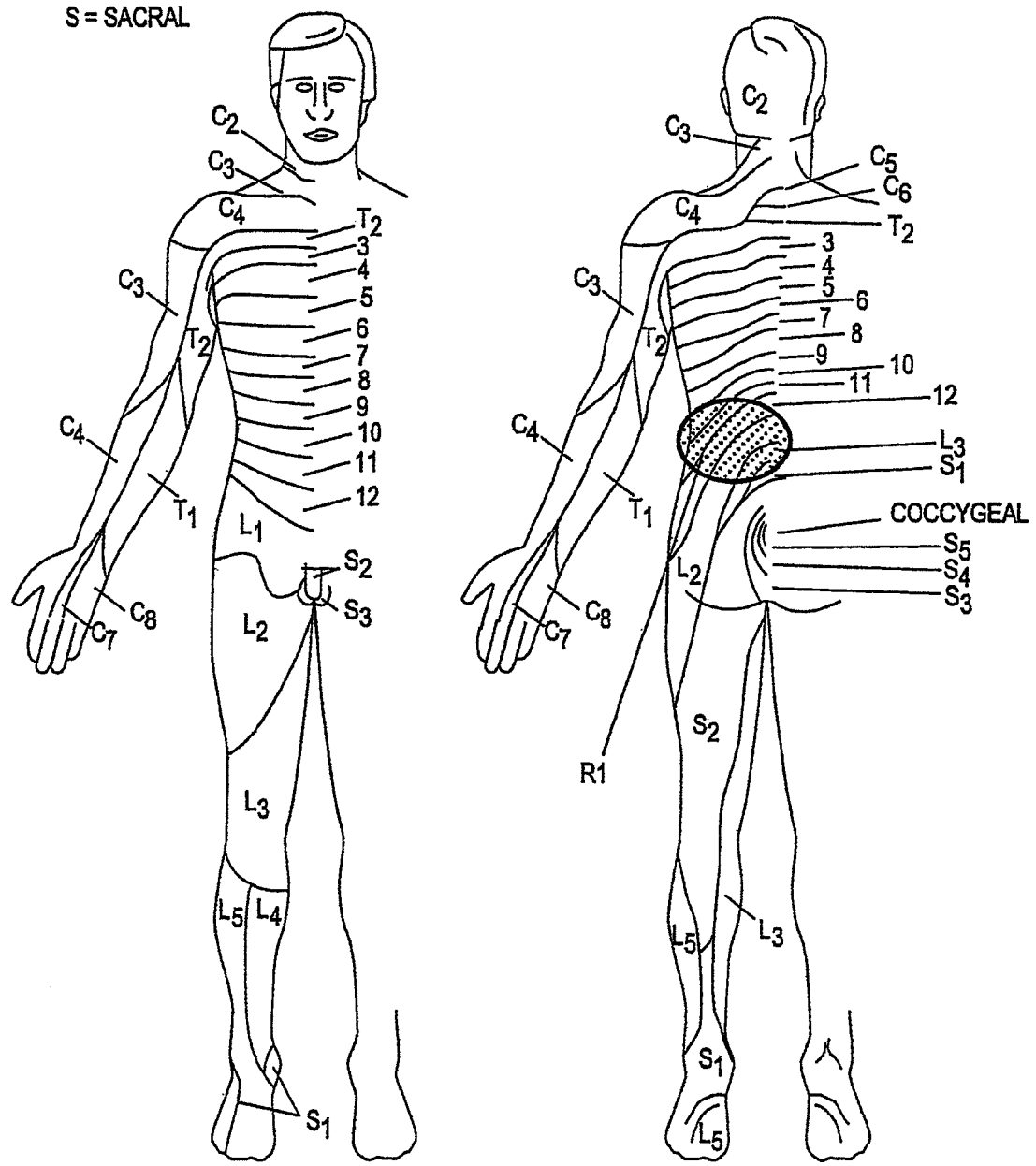
FIG. 4B illustrates an exemplary corresponding dermatome to the stimulation pattern of FIG. 4A.

In the illustrated configuration, a stimulation pattern provided to one of the electrodes positioned in level 3 (i.e., channel #1 "ON") produces pain blocking/relief in the indicated region of the body (i.e., shaded area R1) in FIG. 4B.

It will be appreciated that embodiments of the present invention can stimulate specific dermatome distributions to probe which electrode or group electrodes or combination of electrodes (including drug coated or delivery electrodes) is best positioned or correlates most closely to one or more specifications of pain. As such, a stimulation system according to an embodiment of the present invention may be "fine tuned" to a specific area of coverage type of pain. The results obtained from such testing can be used to one or more stimulation or treatment regimes (i.e., series of stimulations in the presence of or in combination with a therapeutic agent from a coated electrode) for a particular patent for a particular type of pain. These pain treatment regimes may be programmed into a suitable electronic controller or computer controller system (described below) to store the treatment program, control and monitor system components execution of the stimulation regime as the desired therapeutic regime is executed.

Figure 5B:
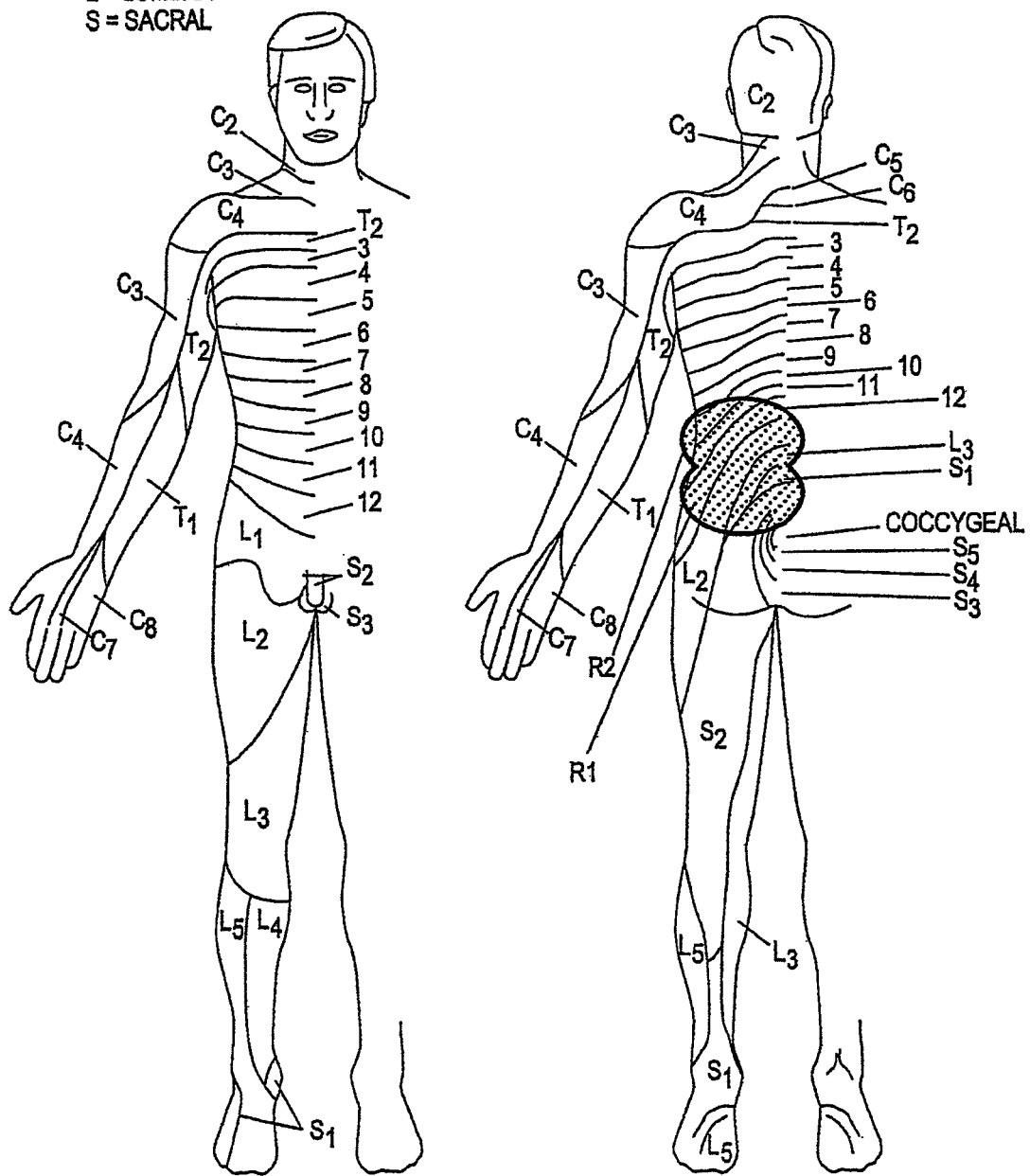
FIG. 5B illustrates an exemplary corresponding dermatome to the stimulation pattern of FIG. 5A.

FIG. 5A provides another example of distribution of pain relief using a multi-channel stimulation system and method. In the illustrated configuration and stimulation pattern, a stimulation pattern is provided to one electrode each in levels 2 and 3 via channels #1 and #2. This stimulation electrode pattern provides pain blocking/relief in the indicated region of the body (i.e., areas R1, R2) of FIG. 5B.

Figure 6A:
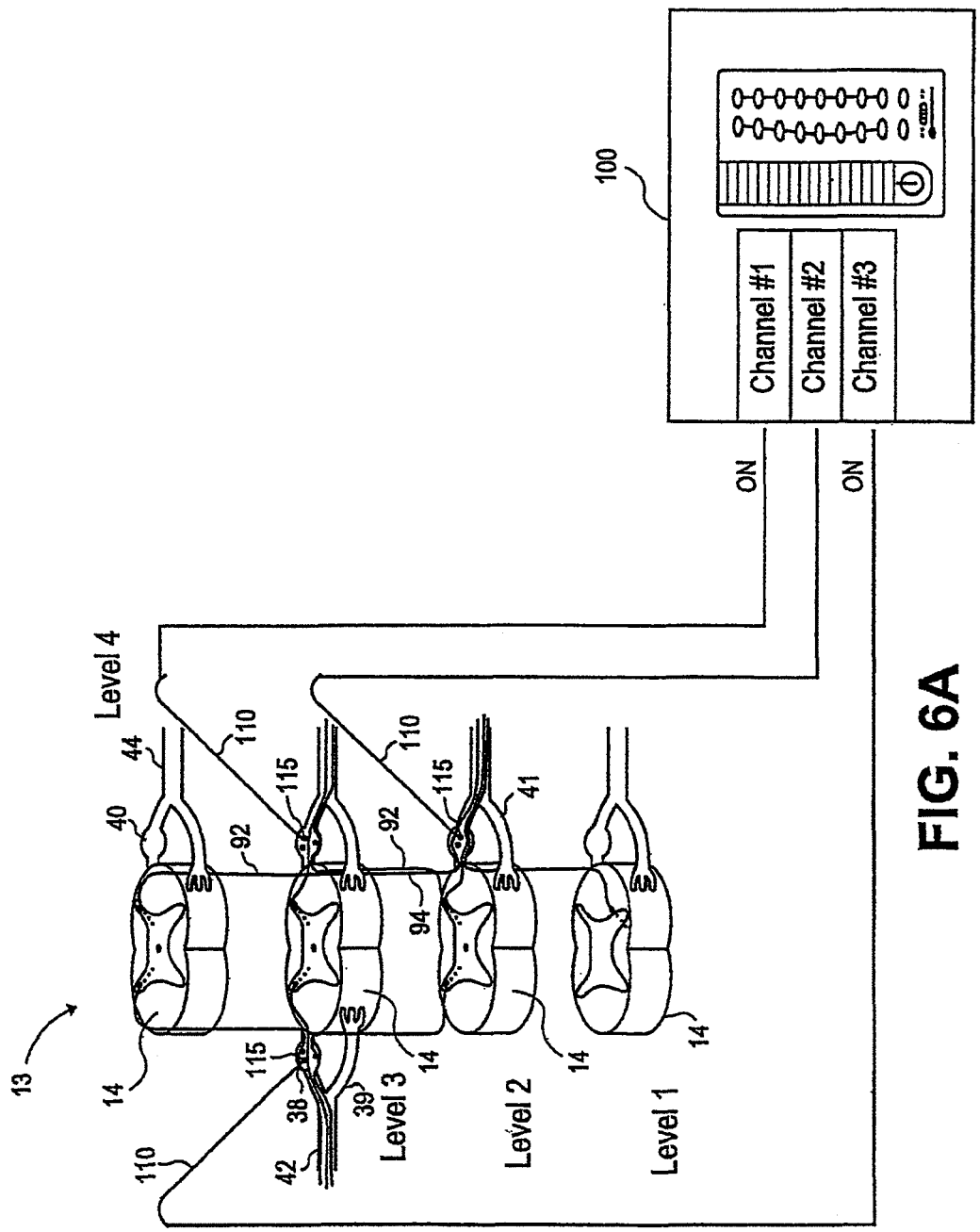
FIG. 6A illustrates a two electrode, single level activation pattern
Figure 6B:
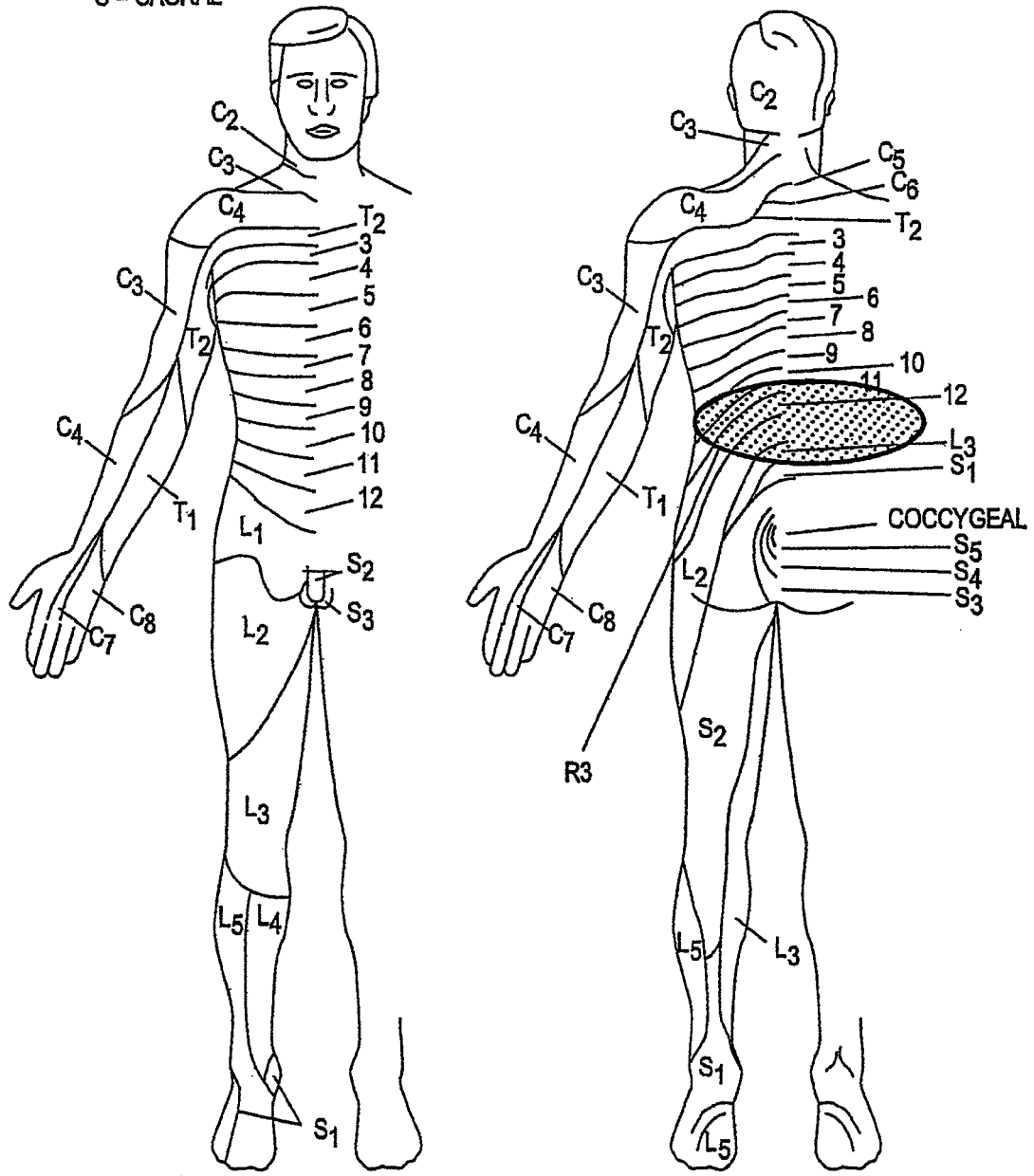
FIG. 6B illustrates an exemplary corresponding dermatome to the stimulation pattern of FIG. 6A.

FIG. 6A provides another example of distribution of pain relief using a multi-channel stimulation system and method. In the illustrated configuration and stimulation pattern, a stimulation pattern provided to both electrodes in level 3 via channels #1 and #3 provides pain blocking/relief in the indicated region of the body (i.e., area R3) of FIG. 6B.

Figure 7A:
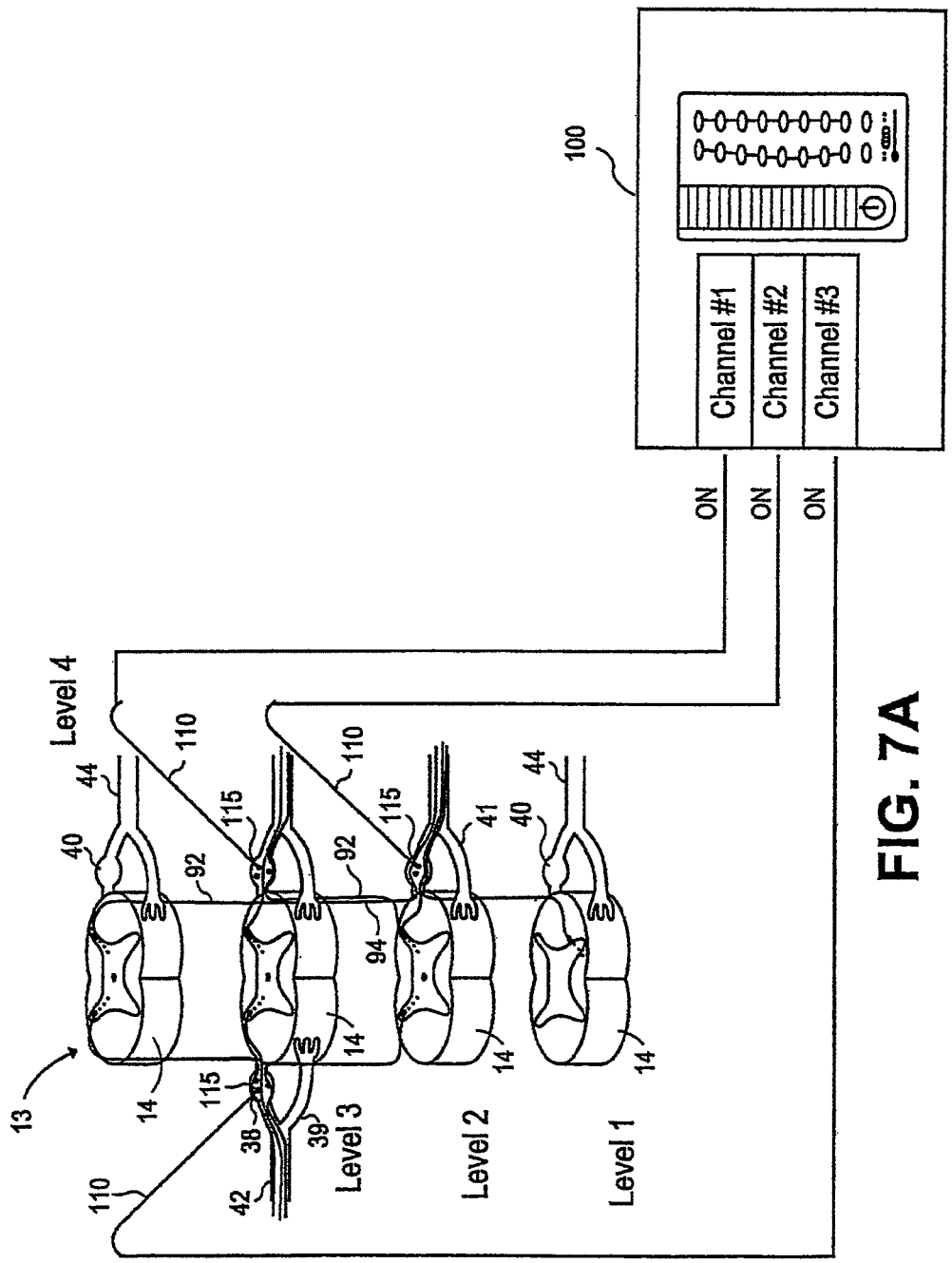
FIG. 7A illustrates a single electrode level and a two electrode level activation pattern and FIG. 7B illustrates an exemplary corresponding dermatome to the stimulation pattern of FIG. 7A.
Figure 7B:
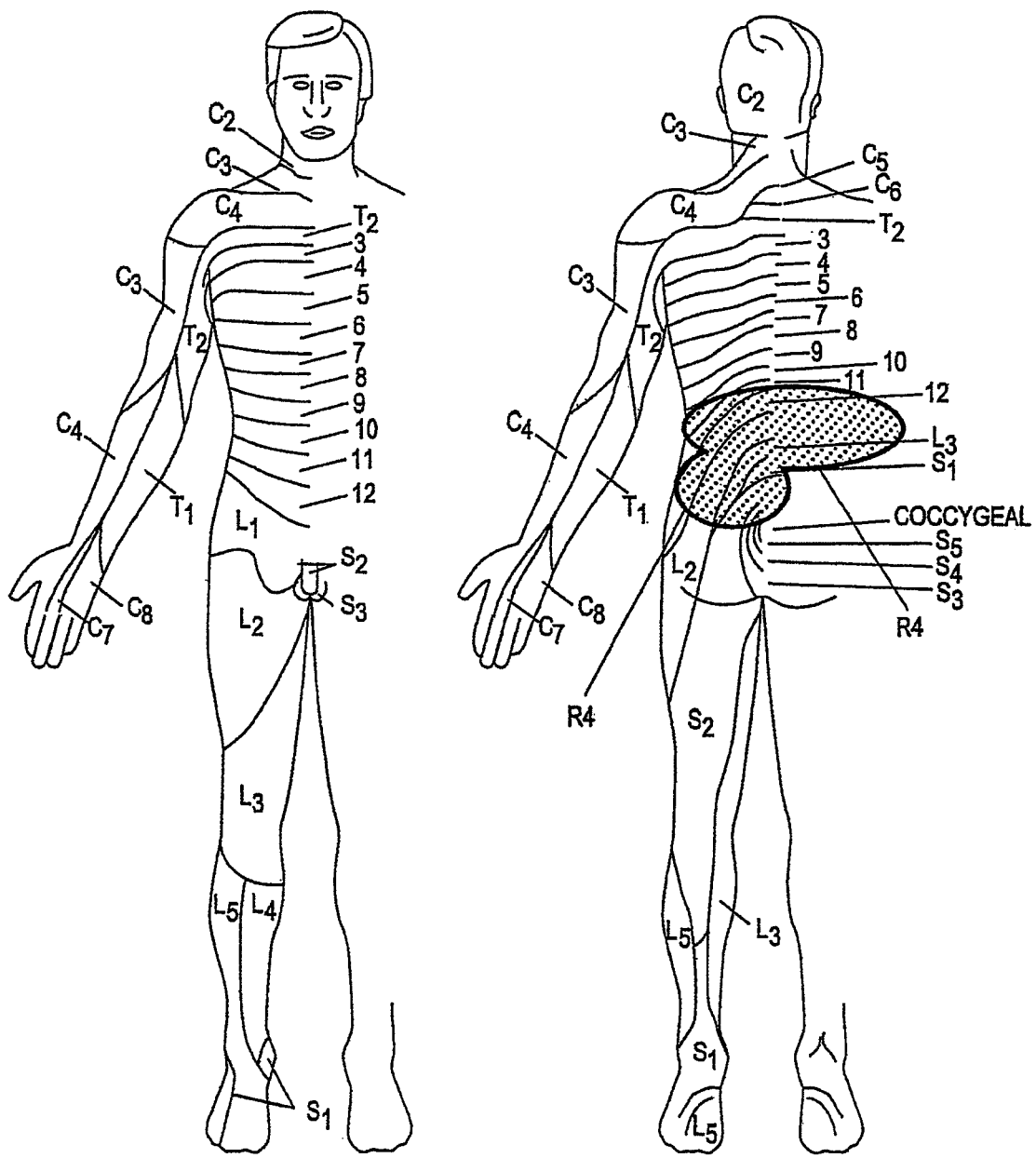

FIG. 7A provides another example of distribution of pain relief using a multi-channel stimulation system and method. In the illustrated configuration and stimulation pattern, a stimulation pattern is provided to all electrodes in the system via channels #1, #2 and #3. This stimulation electrode pattern provides pain blocking/relief in the indicated region R4 of the body (i.e., FIG. 7B). It is to be appreciated that the electrode placement and blocking region patterns illustrated by FIGS. 4A-7B may be modified using information such as in FIGS. 3B and 3C for targeted placement to specific portions of the body depending upon individual needs.

Micro-electrode and stimulation system embodiments of the present invention may be implanted into a single nerve root ganglion utilizing the implantation methods of the present invention. The implantation methods described herein provide numerous advantages, including but not limited to: low risk percutaneous access route similar to other procedures, direct delivery of localized quantities of pharmacological agents at the nerve root when using embodiment having electrodes coated with pharmacological agents, and electrode placement that enables preferential, selective nerve fiber stimulation.

Figure 8A:
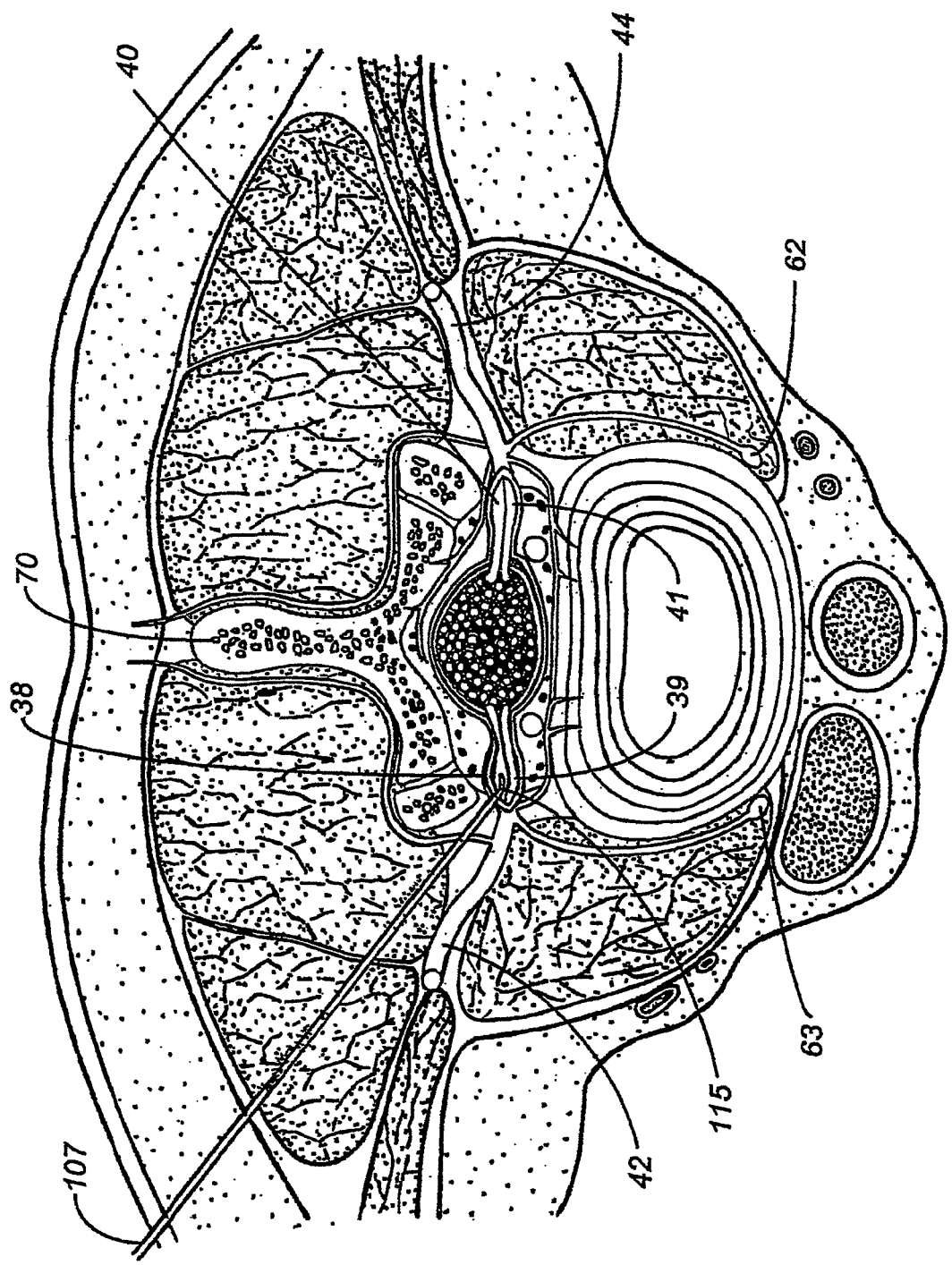
FIG. 8A is a section view of a spinal level with an electrode being implanted into a dorsal root ganglia and FIG. 8B is the view of FIG. 8A with the delivery catheter being withdrawn and the electrode implanted into the dorsal root ganglia.

FIG. 8A illustrates a cross section view of a spinal level. Peripheral nerves 44, 42 feed into dorsal root ganglia 40, 38 and ventral nerves 41, 39 respectively. A vertebral body 70 and two sympathetic nerve ganglia 62, 63 are also illustrated. In this embodiment, the method includes advancing a suitable catheter 107 medially towards the vertebral body 70, then along the peripheral nerve 42 towards the dorsal root ganglion 38. The catheter 107 is advanced using external imaging modalities for guidance such as fluoroscopy or other suitable medical imaging technique. The vertebral foramen offers a good landmark visible under fluoroscopy and useful in locating the DRG 38.

Figure 8B:
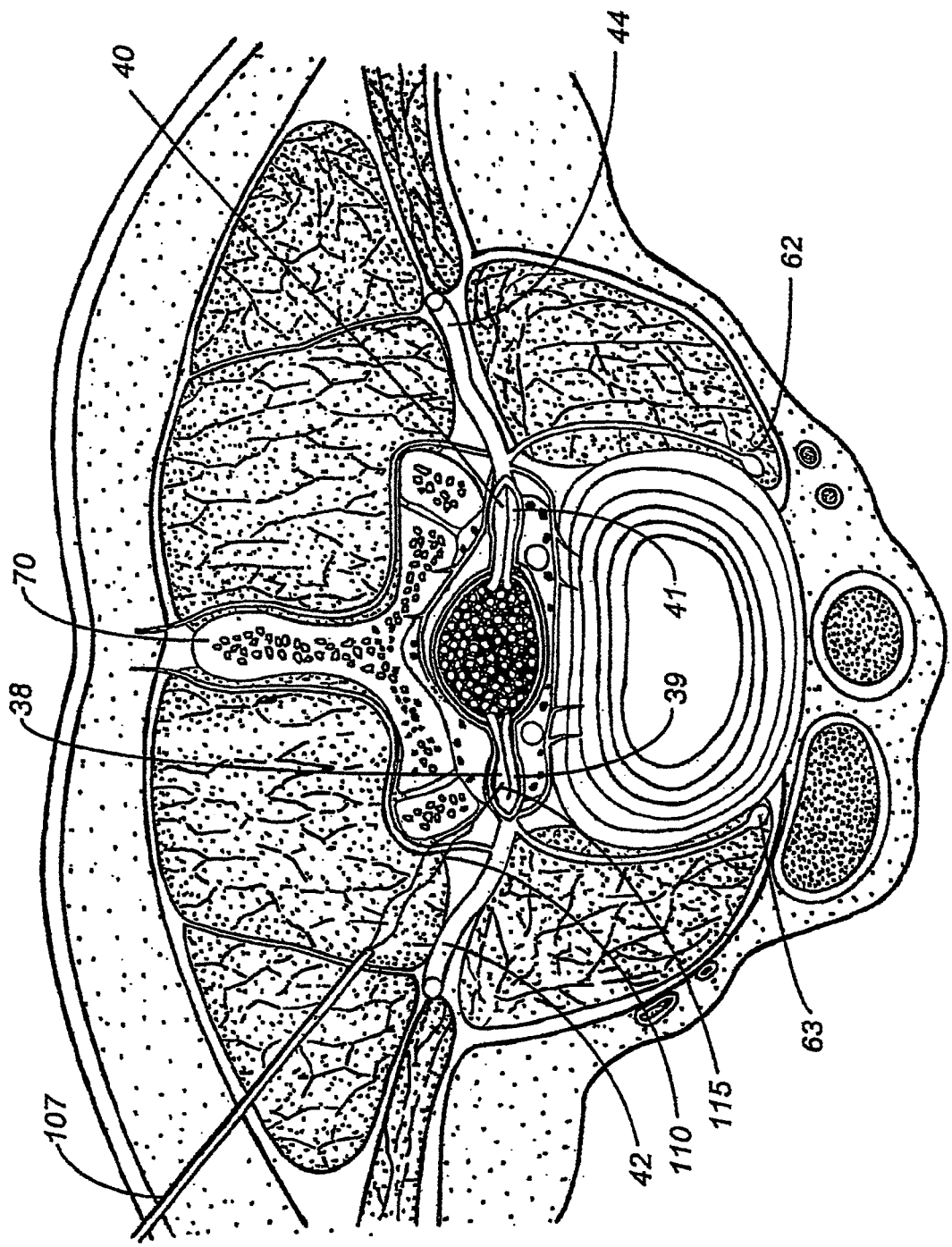

The electrode 115 is implanted in proximity to the dorsal root ganglion by forming an opening in the dorsal root ganglion epinurium and passing the electrode through the opening (FIGS. 8A, 8B). The opening may be formed using conventional methods such as a cutting edge on or provided to the tip of the catheter 107, with an instrument advanced through a working channel within the catheter 107 or through the use of other suitable endoscopic or minimally invasive surgical procedure. Alternatively, the electrode body or distal end may be provided with a tissue cutting or piercing element to aid in piercing tissue (see, e.g., tip 908 in FIG. 20A). As the catheter 107 is withdrawn, the microelectrode leads 110 are deployed and attached, anchored or otherwise secured to the tissue, anatomy or bones adjacent the DRG 38 to reduce the likelihood that electrode 115 will be pulled from the DRG 38. In alternative embodiments described below, the microelectrode leads 110 may be fixed prior to electrode implantation into a nerve root ganglion.

Note that the electrode 115 is sized and shaped to fit within the DRG 38. A typical DRG is generally spherical with a diameter of 3-5 mm. Of course, a range of DRG sizes occur in humans and may vary in size depending on the age and sex of the individual and other factors. Electrode embodiments may be provided in a range of sizes to accommodate the specific anatomical characteristics of a patient. A number of factors are considered when selecting an appropriate DRG electrode embodiment for use in an individual.

Electrode placement within the DRG may be confirmed using neurodiagnostic testing techniques such as somatosensory evoked potential (SSEP) and electromyography (EMG) adapted for the methods and systems described herein. One illustrative example includes the placement of sensing electrodes in the sensory nervous system above and below the DRG level having the implanted electrode(s). Implant the electrode into the targeted DRG. Apply a test stimulation to the DRG and measure voltage potential at the sensory electrodes above and below the targeted DRG to confirm that the electrode is implanted in the targeted DRG. A test stimulation may range from 0.4 v to 0.8 v at 50 Hz or may be some other suitable stimulation level based on the evoked potential measurement technique used. In this way, conventional fluoroscopy techniques and instruments may be used to advance towards and implant the electrode into the DRG and confirm that the electrode is correctly implanted and stimulating the targeted DRG.

Figures 10A, 10B:
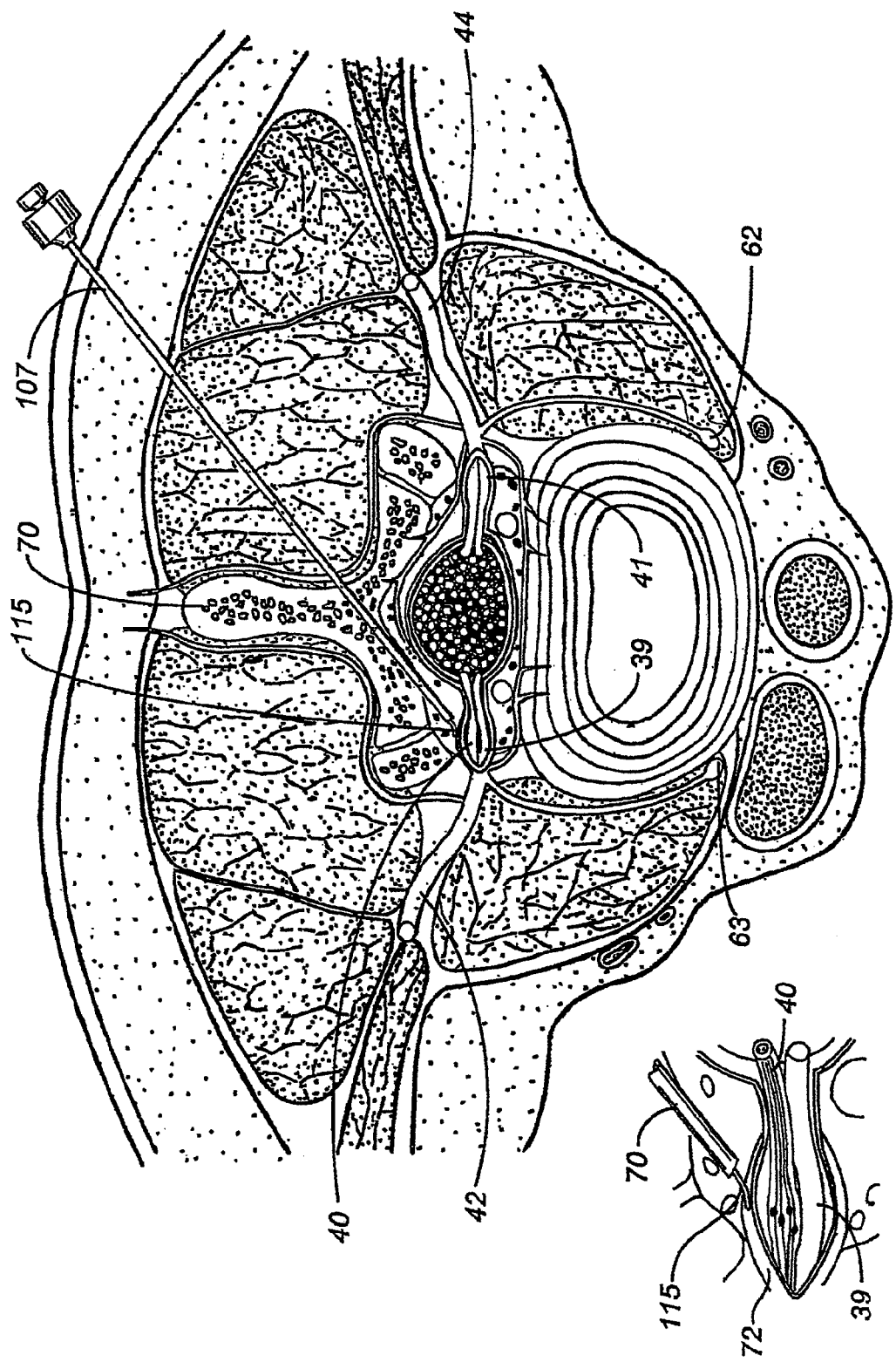
FIG. 10A is a section view of a spinal level with an electrode being implanted onto or in the nerve root epinurium using an approach that crosses a medial line of the level of interest and FIG. 10B is an enlarged view of the implanted electrode in FIG. 10A.

A number of different approaches are available for maneuvering an electrode into position on, in or about a DRG. Several exemplary approaches are provided in FIGS. 8-10 in a section view of the cauda equina portion of the spinal cord. In these examples, electrodes 115 are placed on or in a ganglion on a representative sacral spinal level. Sympathetic nervous system ganglia 62, 63 are also indicated. DRG 40 and ventral root 41 are associated with peripheral nerve 44. DRG 38 and ventral root 39 are associated with peripheral nerve 42.

FIGS. 8A and 8B illustrate a lateral approach to a DRG 38 using a suitable catheter 107. The catheter advances adjacent to the peripheral nerve 42 medially towards the DRG 38. The DRG dura is pierced laterally and the electrode 115 is advanced into the DRG interior. Thereafter, the electrode 115 is implanted into the DRG interior. Next, as is illustrated in FIG. 8B, the catheter 107 is withdrawn from the DRG 38 and deploys the electrode leads 110. The electrode leads 110 may be anchored to the vertebral body 70 using suitable fixation techniques. The leads 110 are then connected to a pulse generator/controller (not shown).

FIG. 9A is anatomically similar to FIGS. 8A and 8B. FIG. 9A illustrates an alternative DRG implantation approach that crosses the medial line inferior to the DRG of interest. The catheter 107 is advanced in a superior pathway towards the foramen and using the foramen under fluoroscopic guidance into the DRG. As illustrated in FIGS. 9A and 9B, there is provided a method of stimulating a dorsal root ganglion by implanting an electrode within the dorsal root ganglion. In some embodiments, the implanting procedure includes passing a portion of the electrode through the spinal epidural space. Electrodes in systems of the present invention onto or in the nerve root epinurium 72 (FIGS. 10A and 10B) or within the nerve root (i.e., FIGS. 9A,B). Moreover, in some embodiments, there is also the step of forming an opening in the dorsal root ganglion epinurium 72 and then passing the electrode through the opening (see, i.e., FIG. 9B).

Figure 11:
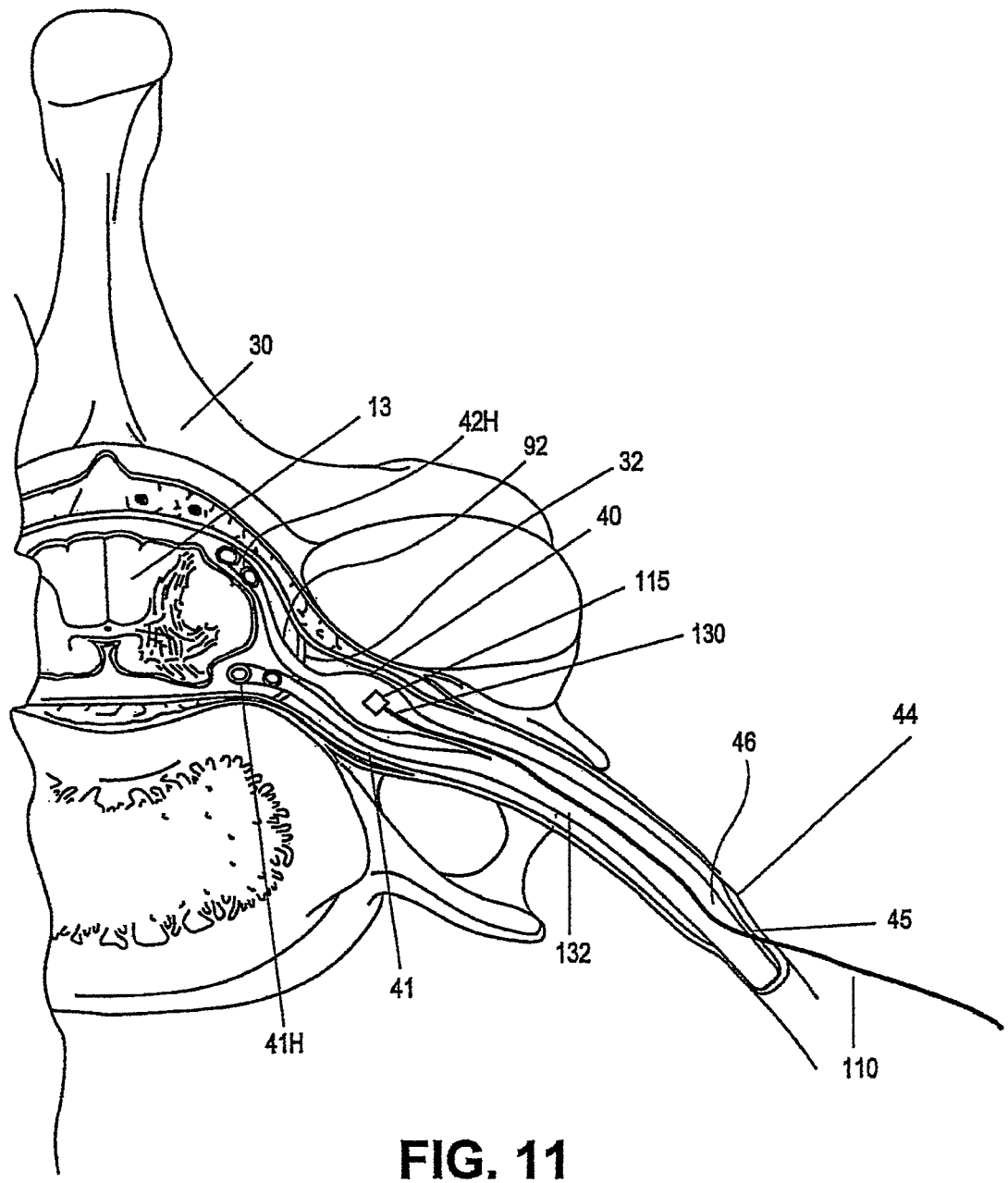
FIG. 11 is a illustrates an alternative DRG implantation technique using an approach along the peripheral nerve.

FIG. 11 illustrates a section view through a portion of the spinal cord 13 with another alternative electrode implantation technique. In contrast to the earlier described methods that externally approach the DRG and involve piercing or entering the DRG epinurium 72, FIG. 11 illustrates an internal approach to the DRG interlascular from within the nerve sheath of a peripheral nerve 44. FIG. 11 illustrates a section view of the nerve sheath partially removed to reveal the underlying nerve bundle 46. In this illustrative example, an opening is made in the peripheral nerve 44 sheath at a point 45 lateral to the DRG 40. The microelectrode 115 enters the nerve 44 sheath through opening 45 using suitable endoscopic or minimally invasive surgical techniques. Next, the electrode 115 is advanced towards and into the DRG 40.

As each of these illustrative embodiments make clear, the placement of the electrode relative to the DRG enables activating the electrode to selectively stimulate sensory nerves. Additionally, the placement of the electrode according to the methods of the invention enable activating the electrode to stimulate sensory nerves within the DRG or without stimulating motor nerves in the nearby ventral root. The control system described herein also provides stimulation levels that activate the electrode to stimulate at a level that preferably stimulates myelinated fibers over unmyelinated fibers.

In addition, as will be described in greater detail below, FIG. 11 illustrates an electrode embodiment where the electrode tip and shaft may be coated with pharmacological agents to assist in the stimulation therapy or provide other therapeutic benefit. As illustrated, the electrode includes a tip coating 130 and a shaft coating 132. The pharmacological agent in each coating 130, 132 could be the same or different. One advantage of implanting through the nerve sheath is that the coated shaft 132 may include a pharmacological agent active or beneficial to neural activity in the ventral nerve root 41 since this coated shaft is advantageously positioned proximal to the ventral root 41. The shaft coating 132 may also be selected to reduce inflammation or irritation caused by the presence of the shaft within the nerve sheath.

Figure 12A:
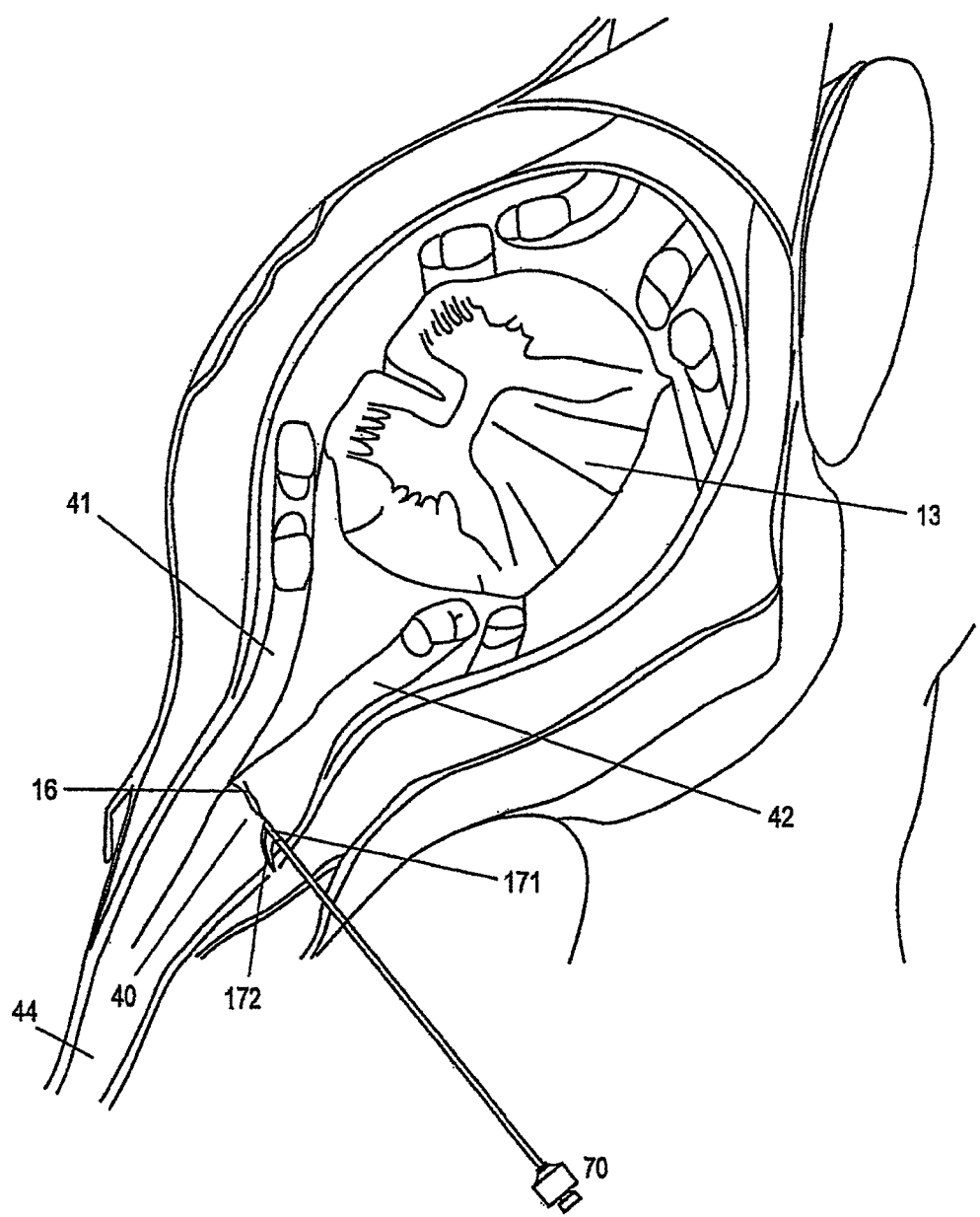
FIG. 12A illustrates an implantation technique using an electrode and anchor design illustrated in FIG. 12B.
Figure 12B:
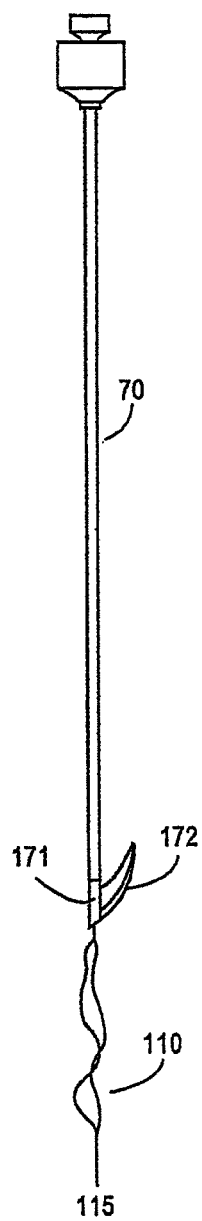
FIG. 12C illustrates an alternative anchoring technique using the surrounding vertebral bone.

FIGS. 12A and 12B illustrate an embodiment of an exemplary anchor body 171 with a fixation hook 172 used to secure the leads 110 once the electrode 115 is implanted into the DRG 40. FIG. 12A is a section view of a portion of the spinal cord 13 showing the dorsal root 42, ventral root 41, DRG 40 and peripheral nerve 44. In this illustrative embodiment, a catheter 70 is used to maneuver the electrode 115, leads 110 and anchor 171 about the DRG 40 implantation site. Once a suitable site is identified, the hook 172 is inserted into the fascia layer of the DRG. The hook 172 may have various shapes and contours to adapt it to engaging with and securing to the outer DRG layer or within the outer DRG layer. FIG. 12B illustrates an exemplary anchor body 171 and hook 172 mounted onto the distal end of a catheter 70. The anchor body 171 and hook 172 may be maneuvered into position using the catheter 70 alone or in combination with other suitable surgical, endoscopic or minimally invasive tools. Similarly, the electrode 115, leads 110 may be moved into position for implantation on, in or about targeted neural tissue. In other alternative electrode embodiments, the electrode 115 is implanted on, in or about a DRG is provided with a flexible tip that helps to prevent or mitigate chronic friction and ulceration.

Alternatively, the electrode leads 110 or other supporting or anchoring structures may be attached to the adjacent bony structure, soft tissue or other neighboring anatomical structures. In addition, there may also be provided a fixation, anchoring or bonding structure positioned proximal to the electrode anchor 172 that absorbs some or all proximal movement of the leads 110 so that the electrode is less likely to be pulled from or dislodged from the implantation site. The goal of the anchoring and other strain absorbing features is to ensure the electrode remains in place within or is less likely to migrate from the implanted position because of electrode lead 110 movement (i.e., lead 110 movement pulls the electrode 115 from the implantation site or disrupts the position of the electrode 115 within the implantation site). It is to be appreciated that numerous techniques are available to aid in electrode placement including percutaneous placement of single/multiple hooks or anchors, vertebral anchor or posts, microsutures, cements, bonds and other joining or anchoring techniques known to those of ordinary skill in the art. It is also to be appreciated that other components of the stimulation system embodiments described herein may also be adapted for attachment to surrounding tissue in proximity to the stimulation site or near the electrode implantation site. Other components include, for example, the stimulation controller, master controller, slave controller, pulse generator, pharmacological agent reservoir, pharmacological agent pump and the battery.

Figure 12C:
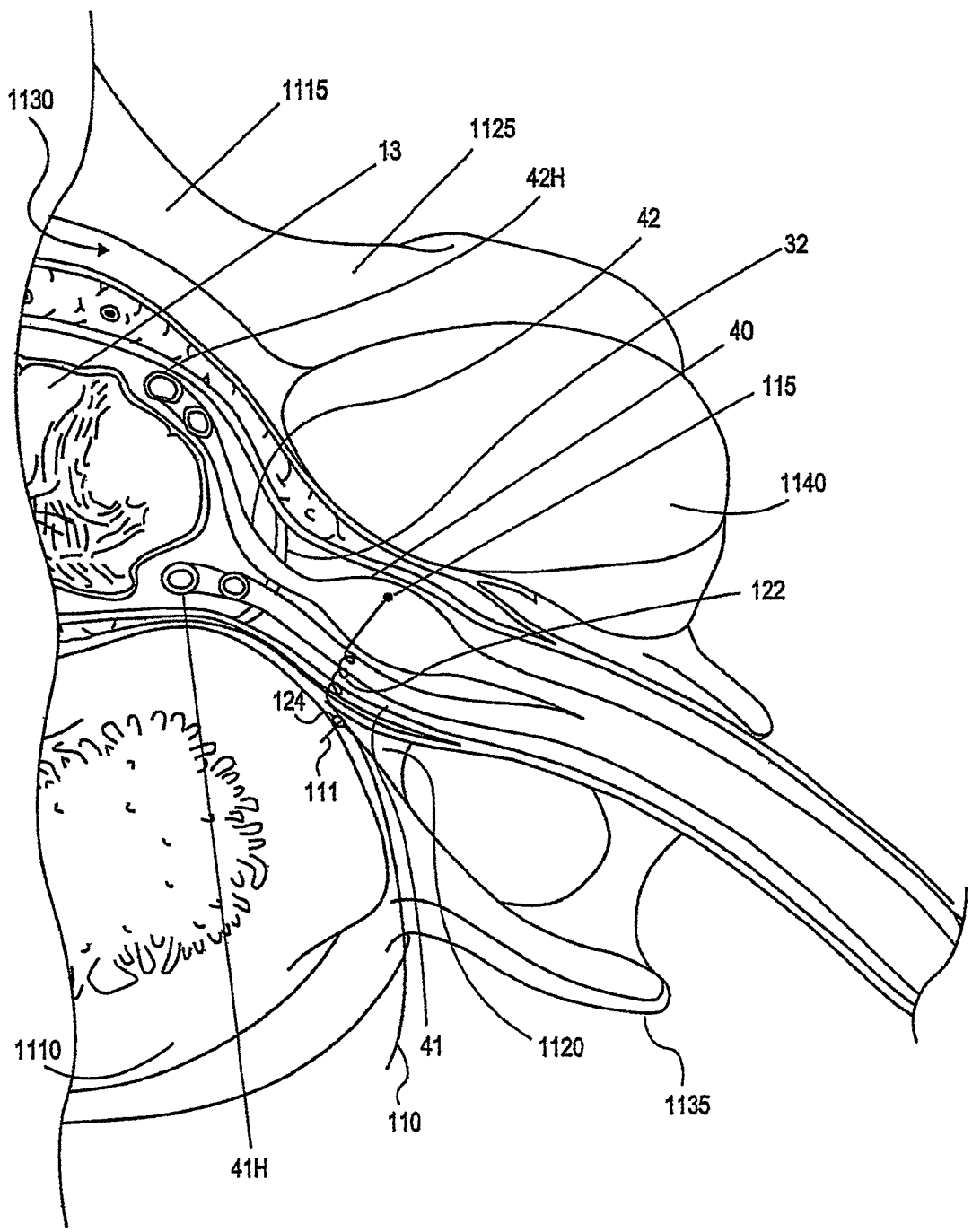

FIG. 12C illustrates an exemplary anchoring of electrode leads 110 to bone surrounding the electrode implantation site. FIG. 12C illustrates a section view through a portion of the spinal cord 13 showing the ventral root 41, the dorsal root 42 and dorsal root ganglion 40. FIG. 12C also illustrates the surrounding bone of the spine such as vertebral body 1110, the spinous process 1115, the pedicle 1120, the lamina 1125, the vertebral arch 1130, transverse process 1135, and facet 1140. Electrode 115 is implanted into the DRG 40 and the electrode leads are held in place using a suitable anchor 111. In this embodiment, the anchor 111 is secured to the vertebral body 1110. The anchor 111 represents any suitable manner of securing the bony portions of the spine such as tacks, staples, nails, cement, or other fixation methods known to those in the surgical or orthopedics arts. A strain relief 122 is present between anchor 111 and the DRG 40 (see FIGS. 13A and 14A). The strain relief 122 is used to absorb motion that may move the electrode 115 within the DRG 40 or remove the electrode from the DRG 40. In this illustrative embodiment, the strain relief 122 is a coiled portion of the electrode lead 110. One or more strain reliefs 122 may be provided between the anchor 111 and the DRG 40 or between the anchor 111 and the battery or controller of the stimulation system (not shown).

Figure 13A:
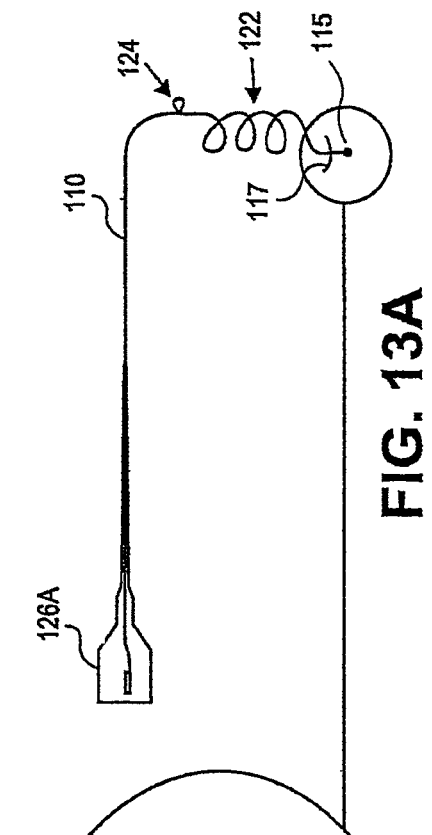
FIG. 13A illustrates the monopolar stimulation component embodiment illustrated in FIG. 13B implanted in a DRG.
Figure 14A:
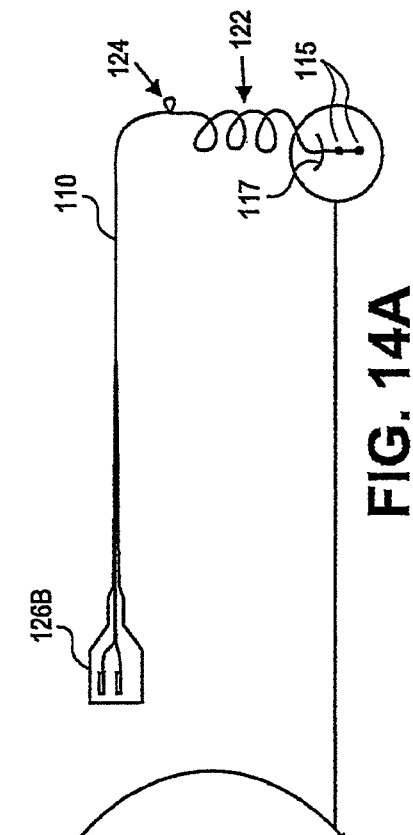
FIG. 14A illustrates the bi-polar stimulation component embodiment illustrated in FIG. 14B implanted in a DRG.
Figure 13B:
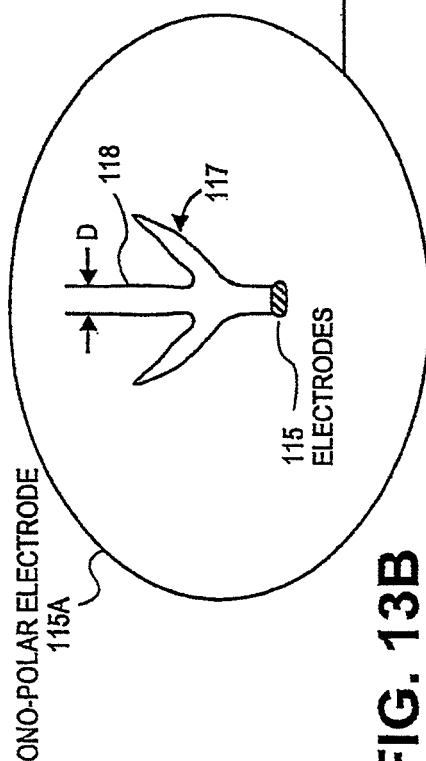
Figure 14B:
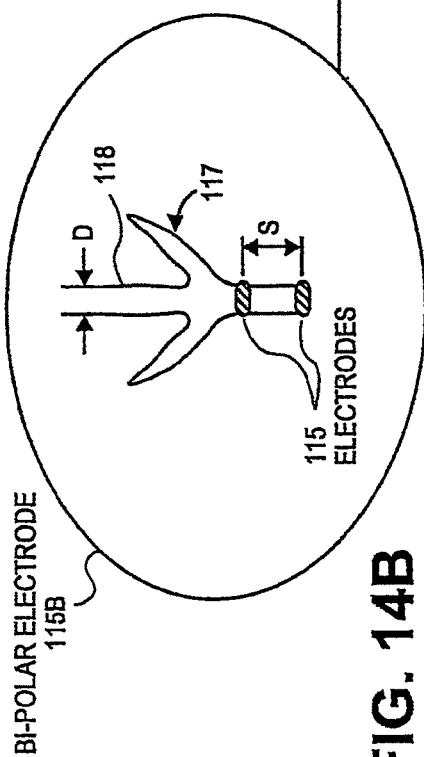

FIGS. 13A-14B illustrate mono-polar and bi-polar stimulation component embodiments of the present invention. FIG. 13A illustrates a mono-polar stimulation component that has a proximal connector 126A adapted to be connected to a pulse generator. A distal electrode 115 is configured to be implanted within the body at a stimulation site. The distal electrode may be a mono-polar electrode 115A (FIG. 13B) or a bi-polar electrode 115B (FIG. 14B). The electrodes are sized for implantation into a nerve root ganglion and will vary according to the nerve root selected. In additional alternative embodiments, the electrode leads and electrode are adapted and sized to advance within a nerve sheath to a nerve root ganglion. The electrodes or their casing may be made of inert material (silicon, metal or plastic) to reduce the risk (chance) of triggering an immune response. Electrodes should be studied for suitability to MRI and other scanning techniques, including fabrication using radio-opaque materials as described herein.

Returning to FIG. 13A, an electrical lead 110 is connected to the proximal connector 126A and the distal electrode 115. A strain relief mechanism 122 is connected in proximity to the stimulation site. The illustrated strain relief mechanism is formed by coiling the electrical lead 110. Other well known strain relief techniques and devices may be used. A fixation element 124 adapted to reduce the amount of movement of the electrical lead proximal to a fixation point is positioned in, on, or through an anatomical structure proximal to the stimulation site. Multiple elements are provided to mitigate or minimize strain and force transmission to the micro-leads 110 or the microelectrodes 115 because the microelectrodes and microelectrode leads used herein are very small and include fine, flexible wires on the order of 1 mm or less and in many cases less than 0.5 mm. Representative electrode and lead dimensions will be described in greater detail below (FIGS. 15A, 15B). As such, in some embodiments, strain and movement may be absorbed or mitigated by the fixation element 124, the strain relief 122 and the electrode anchor 117 (if included). The fixation element 124 may be, for example, a loop, or a molded eyelet. The fixation element may be sutured, tacked, screwed, stapled, bonded using adhesives or joined using other techniques known to those of ordinary skill to secure the fixation element within the body for the purposes described herein.

In one specific implantation embodiment, the method of implanting the electrode is modified based on consideration of the small size and delicate nature of the microelectrode and microelectrode leads. As such, high force actions are taken first followed by light force actions. In this way, the fine microelectrode and microelectrode lead materials are not present during high force operations. Consider an example where an electrode of the present invention will be implanted into a DRG. In an exemplary embodiment, the fixation element 124 is a loop sized to allow passage of the electrode 115. Perform the high force operation of anchoring or otherwise fixing (i.e., adhesion) the fixation element into a vertebral foramen adjacent the selected DRG stimulation site. In general, the fixation site should be as close as practical to the stimulation site. In one specific embodiment, the fixation site is within 3 cm to 5 cm of the stimulation site. Optionally, a guide wire attached to the loop remains in place and is used to guide the electrode and leads to the loop and hence to the implant site. The electrode and leads are passed through the loop (with or without use of a guide wire). The electrode is then implanted on or in the DRG. Optionally, an anti-strain device 122 may also be positioned between the electrode in the implantation site and the fixation element 124. In one illustrative embodiment, a section of microelectrode lead containing a plurality of loops is used as an anti-strain device 122. Finally, the microelectrode lead is secured to the loop using a suitable locking device. It is to be appreciated that the above method is only illustrative of one method and that the steps described above may be performed in a different order or modified depending upon the specific implantation procedure utilized.

In some embodiments, there may also be provided an anchoring mechanism proximal to the distal electrode 115. Examples of anchoring mechanisms include, for example, anchors 117 illustrated in FIGS. 13B and 14B. In still further embodiments, the anchoring mechanism is adapted to anchor the distal electrode 115 within the stimulation site. For example, the anchor mechanism may remain stowed flat against the electrode body 118 during implantation and then deploy from within a nerve root ganglion to anchor against the interior nerve root wall to support the electrode and prevent electrode migration or pull-out. In some embodiments the anchoring mechanism and the distal electrode are integrally formed and in other embodiments they are separate components. In some embodiments, the anchoring mechanism is foamed from a polymer or a silicone.

Selective nerve stimulation affords the use of smaller electrodes. Smaller electrodes create less impingement and are less susceptible to unwanted migration. However, as electrode surface area decreases the impedance of the electrode increases (FIG. 15A). As such, some electrode embodiments will have an impedance much greater than the impedance of conventional stimulation electrodes. In one embodiment, the impedance of a microelectrode of the present invention is more than 2500Ω. This difference in impedance also impacts the performance requirements of stimulation systems, pulse generators and the like used to drive the microelectrodes described herein.

Distal electrodes may come in a wide variety of configurations, shapes and sizes adapted for implantation into and direct stimulation of nerve root ganglion. For example, the distal electrode 115 may be a ring of conductive material attached the leads 110. Alternatively, the distal electrode 115 may be formed from an un-insulated loop of electrical lead. The loop electrode is appealing and has improved wear properties because, unlike the ring that must be joined to the leads 110, the loop is formed from the lead and no joining is needed. In still other embodiments, the electrode may be an un-insulated portion of the lead.

Regardless of configuration, electrodes of the present invention are sized and adapted for implantation into, on or about a ganglion such as, for example, a dorsal root ganglion or a ganglion of the sympathetic nervous system. It is to be appreciated that the size of the electrode varies depending upon the implantation technique and the size of the target ganglion. An electrode implanted through the DRG dura (i.e., FIG. 9A) may be less than 5 mm since the diameter of a DRG may be only 3-5 mm. On the other hand an electrode adapted for implantation along the peripheral nerve sheath (i.e., FIG. 11) may be longer than the electrode that passes through the dura but may face other design constraints since it must advance distally within the nerve sheath to reach the DRG. It is to be appreciated that dimensions of electrode embodiments of the present invention will be modified based on, for example, the anatomical dimensions of the implantation site as well as the dimensions of the implantation site based on implantation method.

FIG. 15B provides some exemplary electrode surface areas for electrode embodiments formed from wire diameters between 0.25 mm to 1 mm, having widths of 0.25 mm or 0.5 mm. As such, embodiments of the present invention provide distal electrode surface area that is less than 0.5 mm$^2$. In other embodiments, the distal electrode surface area is less than 1 mm$^2$. In still other embodiments, the distal electrode surface area is less than 3 mm$^2$.

The sizes of the electrodes of the present invention stand in contrast to the conventional paddle 5 having dimensions of about 8 mm wide and from 24 to 60 mm long (FIG. 1). One result is that conventional stimulation electrodes have larger electrode surface areas than electrode embodiments of the present invention. It is believed that conventional electrodes have an impedance on the order of 500 to 1800Ω operated using a stimulation signal generated by a 10-12 volt pulse generator. In contrast, stimulation electrode embodiments of the present invention have an impedance on the order of 2 kΩ or about 2500Ω, from 2 kΩ to 10 kΩ or higher or even in the range of 10 kΩ to 20 kΩ. As will be described in greater detail below, some pulse generator embodiments of the present invention operate with voltages produced by DC-DC conversion into ranges beyond conventional stimulation systems.

The electrodes may be formed from materials that are flexible and have good fatigue properties for long term use without material failure. The electrode material should be formed from a biocompatible material or coated or otherwise treated to improve biocompatibility. Additionally, electrode materials should be opaque to imaging systems, such as fluoroscopy, used to aid electrode placement during implantation procedures. Examples of suitable materials include but are not limited to Pt, Au, NiTi, PtIr and alloys and combinations thereof. Electrodes may also be coated with a steroid eluding coating to reduce inflammation at the implantation or stimulation site.

With the small surface areas, the total energy required for stimulation of the DRG is drastically reduced because we can achieve high current densities with low currents. One advantage of using microelectrodes is that only a small volume of tissues in the immediate vicinity of the electrodes is stimulated. Another advantage of using microelectrodes is the correspondingly smaller pulse generator and because of decreased battery size.

In addition to the implantable electrodes described above, alternative electrode embodiments may also be used to selectively stimulate a nerve root ganglion. FIG. 16 illustrates an embodiment where conductive rings 205, 207 are positioned on either end of a dorsal root ganglion 40. When activated, the rings 205, 207 capacitively couple stimulation energy into the DRG 40. FIG. 17 illustrates an alternative capacitive stimulation configuration where the capacitive plates 210, 212 are attached to the DRG dura. Embodiments of the present invention are not limited to only one pair of capacitive plates but more than one pair may be used. FIG. 18 illustrates two pairs of capacitive plates attached to the dura of a DRG 40. One pair includes plates 210, 212 and the other pair includes plate 214 and another plate (not shown). As an alternative to attaching the plates directly to the dura, the plates may be attached to an electrode support element 230 adapted to slip around and engage with the DRG dura. Once the electrode support element 230 is in position about the DRG, the plates are properly positioned to selectively stimulate a DRG. The present invention is not limited to only capacitively coupled stimulation energy. FIG. 20 illustrates another alternative embodiment where a wire 235 is wrapped around a DRG 40 creating coils 236 that may be used to inductively couple stimulation energy into a nerve root ganglion. For purposes of discussion, these embodiments have been described in the context of stimulation a DRG. It is to be appreciated that the techniques and structures described herein may also be used to stimulate other nerve root ganglion, other neural structures or other anatomical features.

Figure 20A:
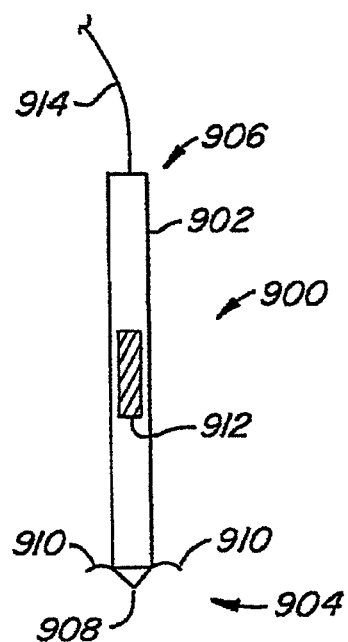
FIG. 20A illustrates an electrode adapted to pierce through and anchor to targeted neural tissue.
Figure 20B:
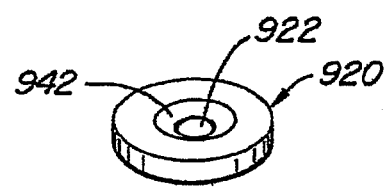
FIG. 20B illustrates a securing ring adapted for use with the electrode in FIG. 20A.

FIGS. 20A and 20B illustrate another electrode embodiment adapted for implantation through neural tissue. Piercing electrode 900 has a body 902, a distal end 904, and a proximal end 906. An electrode surface or component 912 receives stimulation signals and energy from a pulse generator/controller (not shown) via a suitable lead 914. The distal and 904 has a tip 908 adapted to pierce the targeted neural tissue. In addition, one or more anchors 910 are provided at the distal end to help secure the electrode body 902 within the targeted neural tissue. A securing ring 920 (FIG. 20B) is provided to secure the electrode body 902 to or relative to the targeted neural tissue. The anchors 910 may be in a first or stowed position against the electrode body 902 during insertion through the neural tissue and then be moveable into a second or deployed position away from the electrode body 902. In the deployed position (FIGS. 20A, 20C and 20D) the anchors 910 resist the movement of the electrode 900 out of the neural tissue. Numerous alternative anchor configurations are possible. Anchor 910 could be a series of individual struts arrayed in a circular pattern or struts with material between them similar to the construction of an umbrella. Anchor 910 could also be a single anchor.

Figure 20C:
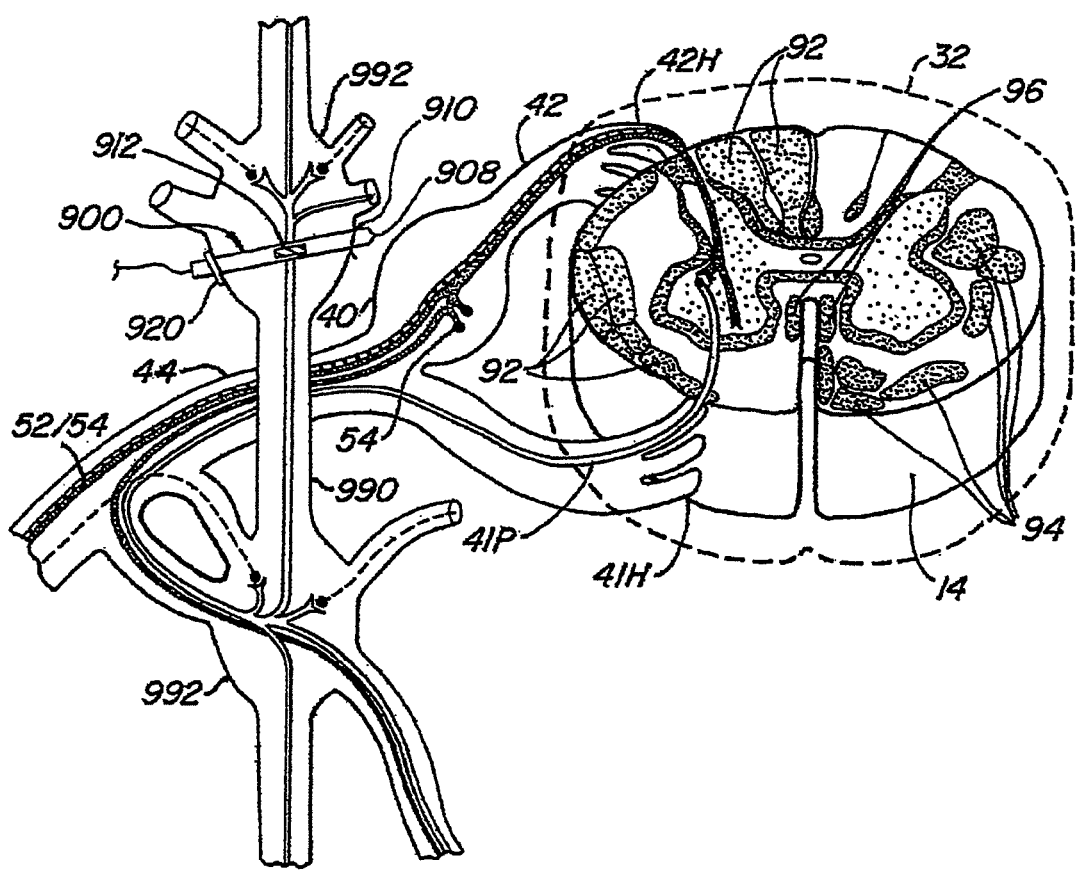
FIG. 20C illustrates a piercing electrode embodiment in position to stimulate a ganglion in the sympathetic chain.

The electrode 900 includes a body 902 adapted to pass completely through targeted neural tissue while positioning the electrode 912 within a portion of the targeted neural tissue. In this illustrative embodiments that follow, the electrode body 902 is adapted to fit within a DRG 40 (FIG. 20D) or a ganglion of the sympathetic chain (FIG. 20C). The electrode 912 may be placed in any location on the electrode body 902 to obtain the desired stimulation or modulation level. Additionally, the electrode 912 may be placed so that modulation or stimulation energy patterns generated by the electrode 912 will remain within or dissipate only within the targeted neural tissue.

A securing ring 920 is used to hold the electrode body 902 in position within and relative to the targeted neural tissue. The securing ring 920 is ring shaped having an annulus 922. In some embodiments, the inner surface 942 is used as a friction locking surface to engage and hold the electrode body 902. In other embodiments, the inner surface 942 contains a surface treatment to secure the electrode body. In still other embodiments, the inner surface 942 is adapted to mechanically engage with and secure the electrode body 902. The securing ring 920 may be formed from a suitable elastic or inelastic material that may be secured to the electrode body 902 and the outer layer of the targeted neural tissue to help prevent electrode pull out or dislodgement. The securing ring 920 may be formed from a biocompatible material suited to gluing or mechanically affixing the ring 920 to the electrode body 902 and the tissue outer layer. The securing ring 920 may be present during or positioned after the electrode 900 is implanted into the targeted neural tissue. In one alternative embodiment, the securing ring 920 is secured to the DRG outer layer and has a complementary engaging feature positioned to engage with an engaging feature on the electrode 900. The electrode body 902 advances through the securing ring annulus 922 and into the DRG 40 until the complementary engaging features engage and stop further distal motion of the electrode body 902 into the DRG. The complementary engaging features may be used alone or in combination with anchors 910 to assist in electrode 900 placement within neural tissue such as a DRG or other ganglion.

Figure 20D:
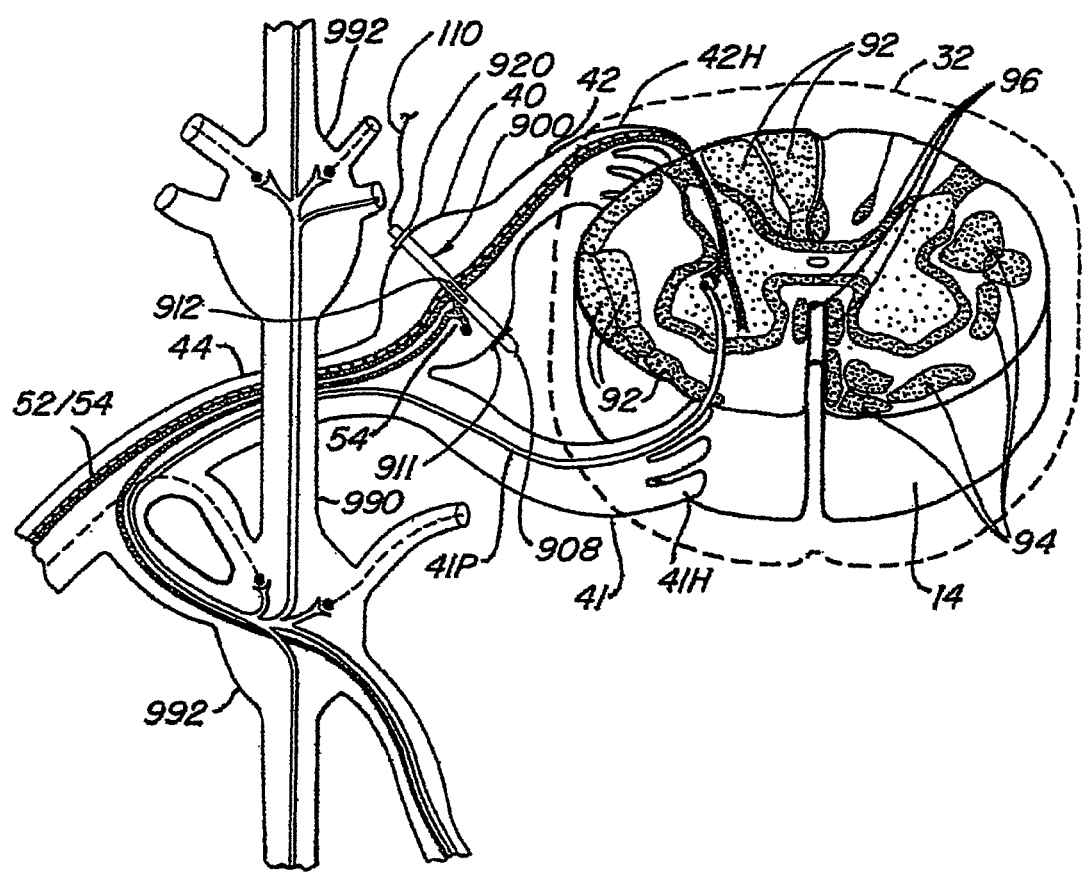
FIG. 20D illustrates a piercing electrode embodiment in position to stimulate a dorsal root ganglion.

FIGS. 20C and 20D illustrate electrode embodiments adapted for implantation through targeted neural tissue illustrated in a section view of the spinal cord 13. Additional details of the various portions of the spinal cord section 14 are described below with regard to FIG. 38. Also illustrated in these views are exemplary sensory pathways 52/54 and motor pathways 41P within peripheral nerve 44 and roots 41/42 and entering the spinal cord. Alternative implantation sites and stimulation alternatives are described in U.S. Pat. No. 6,871,099, incorporated herein by reference in its entirety.

In the illustrative embodiment of FIG. 20C, the electrode 900 is positioned to remain in a non-central location within the targeted neural tissue. In this embodiment, the targeted neural tissue is a ganglion 992 within the sympathetic chain 990. Additional details and specific targeted neural tissue within the sympathetic chain are described below with regard to FIGS. 32 and 33. The electrode 912 is placed on or in the electrode body 902 so that when the electrode body 902 passes through the ganglion 992 and is seated within the securing ring 920 the electrode 912 is in the desired position within the interior of the ganglion 992. Other electrode 912 placement within the targeted neural tissue is possible, for example, by varying the length of the electrode body 902, the angle of penetration into the targeted neural tissue or the position of initial penetration into the targeted neural tissue.

In the illustrative embodiment of FIG. 20D, the electrode 900 is positioned to remain in a generally central location within the targeted neural tissue. In this embodiment, the targeted neural tissue is a DRG 40. The electrode 912 is placed on or in the electrode body 902 such that when the electrode body 902 is seated within the securing ring 920, then the electrode 912 is in the middle of about the middle or center the DRG 40. As before the securing ring 920 and flat anchor 911 secure the electrode 900 in the desired position within the DRG 40. The flat or flap anchor 911 provides similar functionality as the anchor 910. The anchor 911 has flat anchors rather than the curved anchors 910.

In some embodiments, the stimulation electrode tip may be coated with a pharmacological agent. In the embodiment illustrated in FIG. 21, a coating 130 covers that portion of the electrode within the DRG 40. In other embodiments, less or more of the electrode or other implanted components may be suitably coated to achieve a desired clinical outcome. FIG. 21 also illustrates a coating 130 on the electrode shaft or portion of the electrode exterior to the DRG. The coating 132 may be the same or different than the coating 130. For example, the tip coating 130 may include a distal coating containing an agent to aid in the effective stimulation of the DRG. The tip coating 130 may also include a more proximal coating portion (i.e., near where the electrode pierces the dura) that contains an agent to prevent fibrous growth about the electrode. In a further embodiment, the shaft coating 132 would also contain an agent to prevent fibrous growth about the electrode. Additionally, the shaft coating 132 may be selected based on providing a pharmacological agent to interact with the tissue in the ventral root (i.e., the implantation technique in FIG. 11) or within the peripheral nerve sheath.

Examples of desired clinical outcomes provided by pharmacological agents used as coatings include but are not limited to reduction of scar tissue development, prevention of tissue growth or formation on the electrode, anti-inflammation, channel blocking agents and combinations thereof or other known pharmacological agents useful in treatment of pain, or neurological pathologies. In other alternative embodiments, the pharmacological agent may include other compounds that, when placed within the body, allow the pharmacological agent to be released at a certain level over time (i.e., a time released pharmacological agent). In some embodiments, the pharmacological agent is an anti-inflammatory agent, an opiate, a COX inhibitor, a PGE2 inhibitor, combinations thereof and/or another suitable agent to prevent pathological pain changes after surgery. Other suitable pharmacological agents that may be used include those used to coat cardiac leads, including steroid eluding cardiac leads or other agents used to coat other implantable devices.

Embodiments of the present invention include direct stimulation of a nerve root ganglion or other neurological structure while releasing a pharmacological agent from an electrode used to provide stimulation. In one embodiment, the pharmacological agent is released before the electrode is activated. In other embodiments, the pharmacological agent is released after or during the electrode is activated. In still other embodiments, the pharmacological agent is pharmacologically active in the nerve root ganglion during stimulation of the nerve root ganglion. It is to be appreciated that embodiments of the present invention may be altered and modified to accommodate the specific requirements of the neural component being stimulated. For example, embodiments of the present invention may be used to directly stimulate a dorsal root ganglion or a nerve root ganglion of the sympathetic system using the appropriate pharmacological agents, agent release patterns and amounts as well as stimulation patterns and levels.

Figure 22:
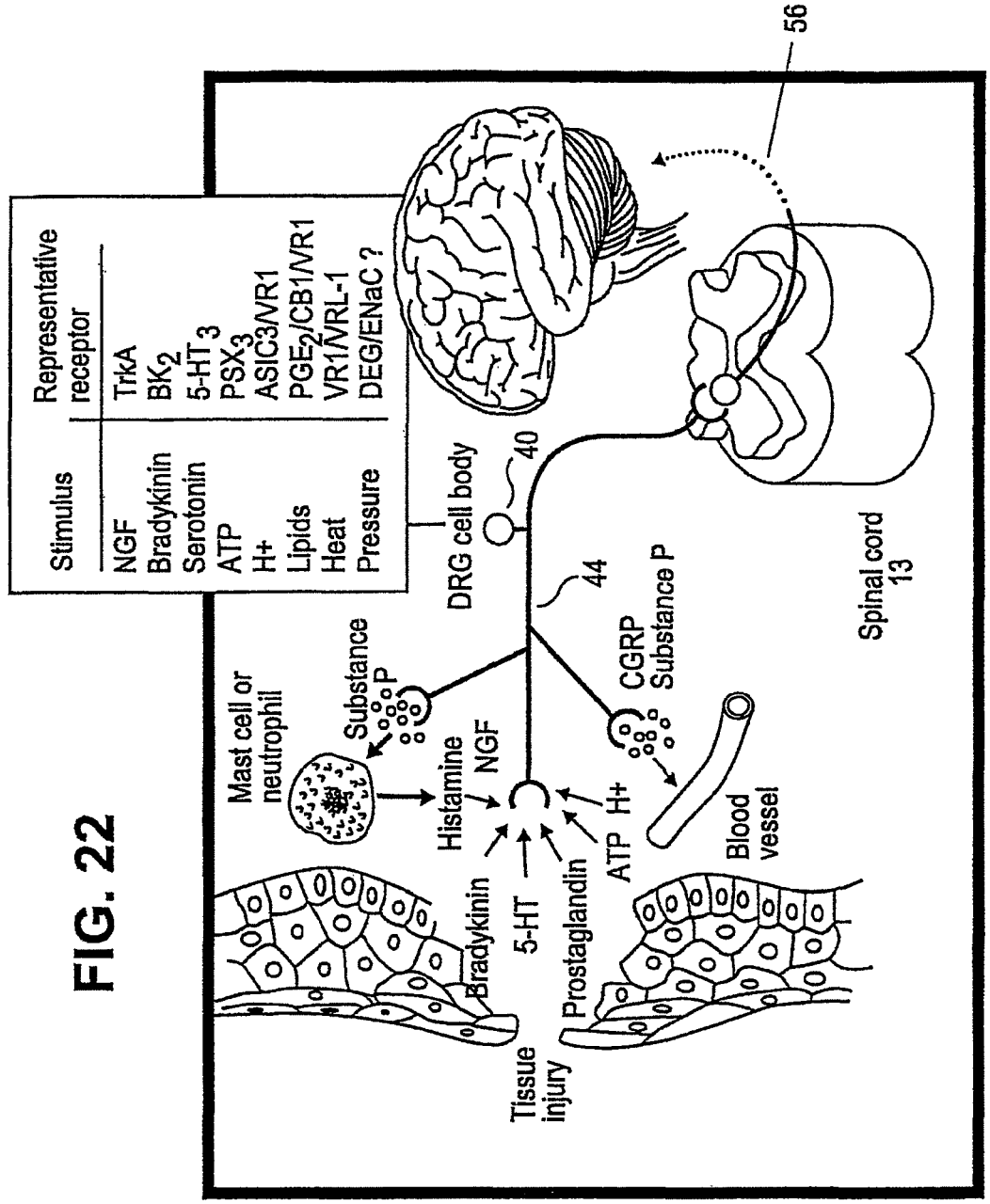
FIG. 22 illustrates the position of the DRG upstream of various a number of stimulation mechanisms.

Turning now to FIG. 22, various stimulation mechanisms are shown. While these various mechanisms potentate pain, each of them acts on the primary sensory neuron. The primary modulator of this cell is its cell body, the DRG 40. One aspect of the present invention is to advantageously utilize the anatomical placement of the DRG 40 within the nervous system to complement other treatment modalities. In another embodiment, stimulation of the DRG 40 as described herein is used in conjunction with a substance acting on a primary sensory neuron. As shown, the other mechanisms are nearer to the illustrated tissue injury than the DRG cell body 40. Put a different way, the DRG 40 is upstream (i.e., closer to the brain/spinal cord 13) of the other pain mechanisms. Thus, this is another illustration of how upstream DRG stimulation may be used to block and/or augment another pain signals.

Electrophysiological studies suggest that Prostaglandin E2 (PGE2), produced by COX enzymes, increases the excitability of DRG neurons in part by reducing the extent of membrane depolarization needed to activate TTX-R $Na^+$ channels. This causes neurons to have more spontaneous firing and predisposed them to favor repetitive spiking (translates to more intense pain sensation). Also illustrated here is how other pro-inflammatory agents (Bradykinin, Capsaicin on the Vanilloid Receptor [VR1]) converge to effect the TTX-R $Na^+$ channel. Opiate action is also upstream from the TTX-R $Na^+$ channel modulation. Embodiments of the present invention advantageously utilize aspects of the pain pathway and neurochemistry to modify electrophysiological excitability of the DRG neurons where electrical stimulation is coupled with pharmacological agents (electrical stimulation alone or in combination with a pharmacological agent) to optimize the efficacy of the stimulation system.

Synergy of electrical and pharmacological modulation may also be obtained using a number of other available pharmacological blockers or other therapeutic agents using a variety of administration routes in combination with specific, directed stimulation of a nerve root ganglion, a dorsal root ganglia, the spinal cord or the peripheral nervous system. Pharmacological blockers include, for example, $Na^+$ channel blockers, $Ca^{2+}$ channel blockers, NMDA receptor blockers and opoid analgesics. As illustrated in FIGS. 23A and 23B, there is an embodiment of a combined stimulation and agent delivery electrode. Note the bipolar electrodes 115B on the tip, the coating 130 and the beveled tip shape for piercing the dura during implantation. The electrode tip is within the DRG epineurium 72 and well positioned to modify and/or influence c-fiber 55 responsiveness. In the illustration, circles represent $Na^+$ ions, triangles represent $Na^+$ channel blockers (such as, for example, dilantin—[phenytoin], tegretol—[carbamazapine] or other known $Na^+$ channel blockers). As the agent is released from coating 130, receptors on c-fiber 55 are blocked thereby decreasing the response of the c-fiber below the response threshold (FIG. 23B). Because the activation potential of the c-fiber has been lowered, the larger diameter A-fiber is preferentially stimulated or the response of the A-fiber remains above the threshold in FIG. 23B.

Embodiments of the present invention also provide numerous advantageous combinational therapies. For example, a pharmacological agent may be provided that acts within or influences reactions within the dorsal root ganglia in such a way that the amount of stimulation provided by electrode 115B may be reduced and yet still achieve a clinically significant effect. Alternatively, a pharmacological agent may be provided that acts within or influences reactions within the dorsal root ganglia in such a way that the efficacy of a stimulation provided is increased as compared to the same stimulation provided) in the absence of the pharmacological agent. In one specific embodiment, the pharmacological agent is a channel blocker that, after introduction, the c-fiber receptors are effectively blocked such that a higher level of stimulation may be used that may be used in the presence of the channel blocking agent. In some embodiments, the agent may be released prior to stimulation. In other embodiments, the agent may be released during or after stimulation, or in combinations thereof. For example, there may be provided a treatment therapy where the agent is introduced alone, stimulation is provided alone, stimulation is provided in the presence of the agent, or provided at a time interval after the introduction of the agent in such a way that the agent has been given sufficient time to introduce a desired pharmacological effect in advance of the applied stimulation pattern. Embodiments of the stimulation systems and methods of the present invention enable fine tuning of C-fiber and Aβ-fiber thresholds using microelectrodes of the present invention having pharmacological agent coatings coupled with electrical stimulation.

Representative pharmacological agents include, but are not limited to: $Na^+$ channel inhibitors, Phenytoin, Carbamazapine, Lidocaine GDNF, Opiates, Vicodin, Ultram, and Morphine.

Figure 23C:
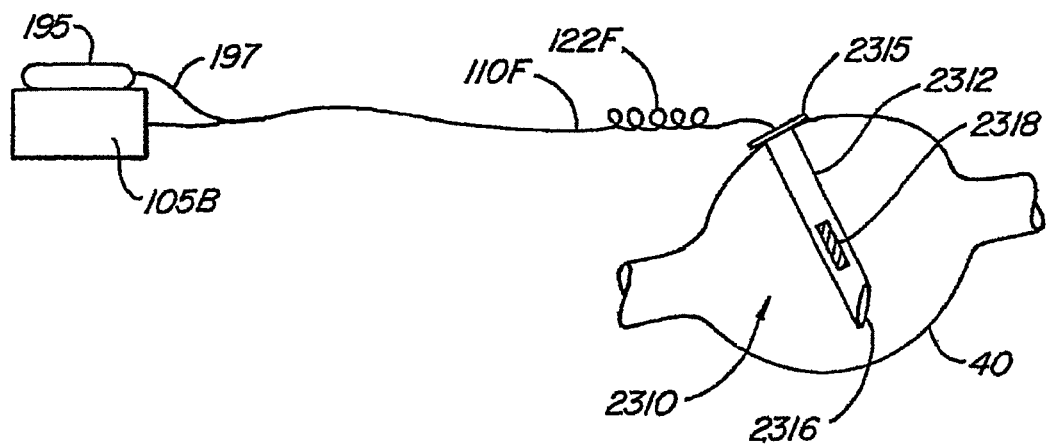
FIGS. 23C and 23D illustrate combined stimulation and pharmacological agent delivery electrodes and systems.
Figure 23D:
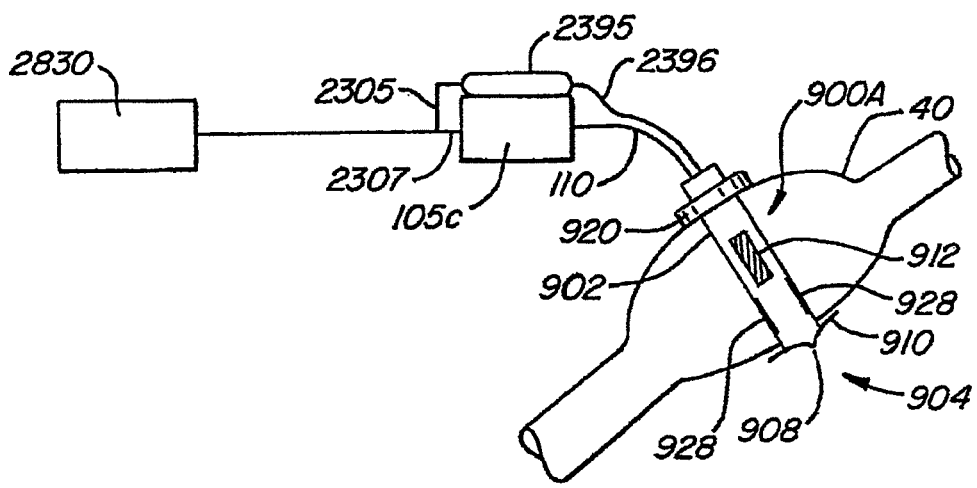

FIGS. 23C and 23D illustrate alternative embodiments for combination neurostimulation and pharmacological agent delivery systems. Additional details of the controller and pulse generated systems suitable for these operations are described below with reference to FIGS. 26-29. While described using combined pump and reservoir delivery systems, it is to be appreciated that the pump for moving the pharmacological agent from the reservoir to and out of the electrode and the reservoir for storing the pharmacological agent before delivery may be two separate components that operate in a coordinated fashion. Pumps and reservoirs may be any of those suited for controlled delivery of the particular pharmacological agent being delivered. Suitable pumps include any device adapted for whole implantation in a subject, and suitable for delivering the formulations for pain management or other pharmacological agents described herein. In general, the pump and reservoir is a drug delivery device that refers to an implantable device that provides for movement of drug from a reservoir (defined by a housing of the pump or a separate vessel in communication with the pump) by action of an operatively connected pump, e.g., osmotic pumps, vapor pressure pumps, electrolytic pumps, electrochemical pumps, effervescent pumps, piezoelectric pumps, or electromechanical pump systems. Additional details of suitable pumps are available in U.S. Pat. Nos. 3,845,770; 3,916,899; 4,298,003 and 6,835,194, each of which is incorporated herein by reference in their entirety.

FIG. 23C illustrates a combined system controller and pulse generator 105B adapted to control the delivery of pharmacological agents from the agent reservoir and pump 195. The pharmacological agent pumped from the agent reservoir and pump 195 travels via a dedicated conduit into a common supply 110F, through a strain relief 122F and into the agent and stimulation electrode 2310. The common supply 110F may be a single line containing both electrode control and power signals from the controller 105B as well as agent delivered from the pump 195 or there could be two separate lines joined together. Regardless of configuration, common supply 110F simplifies implantation procedures because a single line is used to connect the electrode 2310 to the controller 105B and the pump 195.

The combination neurostimulation and pharmacological agent delivery electrode 2310 includes a body 2312 adapted to fit within targeted neural tissue. In this illustrative embodiment, the electrode body 2310 is adapted to fit within a DRG 40. An electrode 2318 is positioned on or in the electrode body 2312 or may be the electrode body 2312. The electrode 2318 is adapted to receive signals and power from the pulse generator 105B via the common supply 110F. The electrode 2318 may be placed in any location on the electrode body 2312 to obtain the desired stimulation or modulation level. Additionally, the electrode 2318 may be placed so that modulation or stimulation energy patterns generated by the electrode will remain within or dissipate only within the targeted neural tissue. In this illustrative embodiment, the electrode 2318 is positioned to remain in a generally central location within the targeted neural tissue. In this embodiment, the targeted neural tissue is a DRG 40. The electrode 2318 is placed on or in the electrode body 2312 such that when the electrode 2310 is seated within the securing ring (described below), then the electrode 2318 is in the middle of about the middle or center the DRG.

A securing ring 2315 is used to hold the electrode body 2312 in position within and relative to the DRG 40. The securing ring 2315 may be formed from a suitable elastic or inelastic material that may be secured to the electrode body 2312 and the outer DRG layer to help prevent electrode pull out or dislodgement. The securing ring 2315 may be formed from a biocompatible material suited to gluing or mechanically affixing the ring 2315 to the electrode body 2312 and the DRG outer layer. The securing ring 2315 may be present during or positioned after the electrode 2310 is implanted into the DRG. In one alternative embodiment, the securing ring is secured to the DRG out layer and has a complementary engaging feature positioned to engage with an engaging feature on the electrode 2310. The electrode body 2312 advances through the securing ring 2315 and into the DRG 40 until the complementary engaging features engage and stop further distal motion of the electrode body 2312 into the DRG. The complementary engaging features may be used to prevent an electrode 2310 intended to be positioned within a DRG from piercing through a DRG.

There is at least one conduit or lumen (not shown) within the electrode body 2312 that provides communication from the portion of the common supply 110F containing the pharmacological agent to the distal opening 2316. In operation, pharmacological agent(s) within the pump/reservoir 195 are delivered, under the control of controller 105B, to the common supply 110F, through the electrode body 2312 and out the distal opening 2316 into the DRG interior. Note that this embodiment of the distal opening 2316 contains a beveled edge that may be used to pierce the DRG during the implantation procedure.

FIG. 23D describes several alternative embodiments suited to combined neurostimulation and pharmacological agent delivery systems and electrodes.

Figure 28:
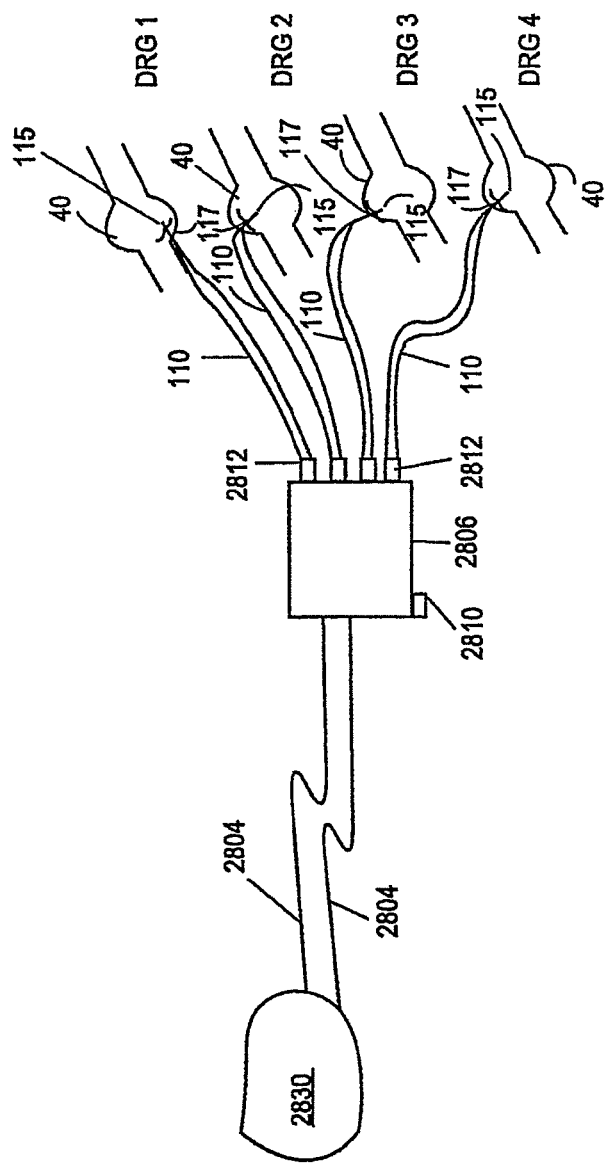
FIG. 28 is an alternative single pulse generator stimulation system embodiment.
Figure 29:
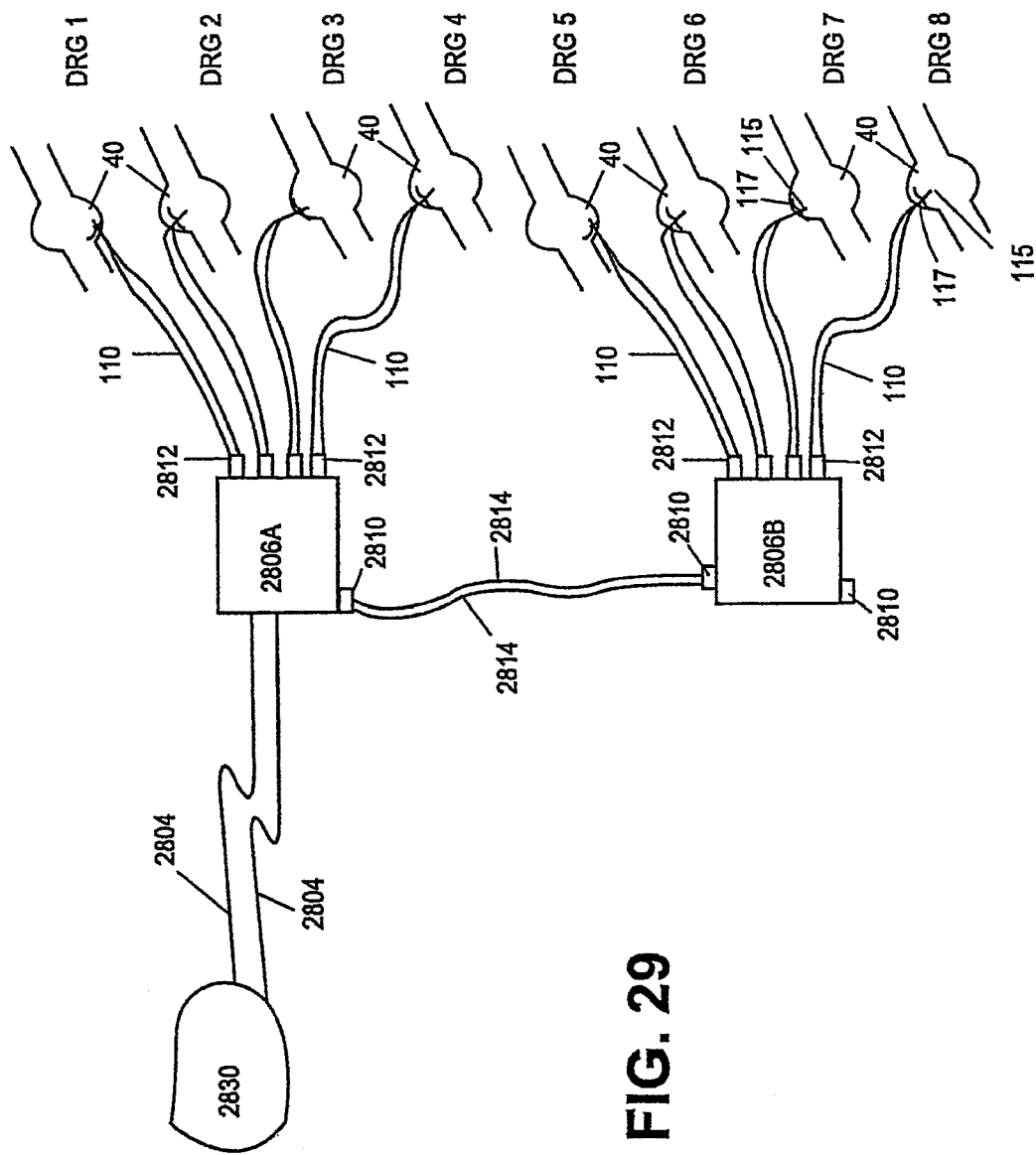
FIG. 29 is an alternative embodiment of a multi-pulse generator stimulation system with generators in a master-slave arrangement.

In contrast to FIG. 23C that uses a combined controller, pulse generator and battery 105B, the configuration in FIG. 23D provides a distributed system similar to those described with regard to FIGS. 28 and 29. A pulse generator and controller 105C and a pharmacological agent reservoir and pump 2395 receive power from battery 2830 using suitable connections 2307 and 2305, respectively. The pharmacological agent reservoir and pump 2395 may have its own controller operated independently of the controller/generator 105C, have its own controller operated under the control of the controller/generator 105C (i.e., in a master/slave relationship) or be operated under the control of the controller/generator 105C. Electrode 912 receives stimulation power from generator 105c via leads 110. Perfusion ports 928 are connected via one or more conduits (not shown) within the electrode body 902 and the conduit 2396 to the pharmacological agent reservoir and pump 2395.

The embodiment of electrode 900A is similar to the electrode 900 of FIG. 20A. Electrode 900A also includes perfusion ports 928 within the electrode body 902 that are in communication with the contents of the pump and reservoir 2395 via the conduit 2396. The electrode body 902 is long enough for implantation through targeted neural tissue. While illustrated implanted generally central to a DRG 40, it is to be appreciated that the electrode body 902 may be longer or shorter to accommodate different sizes of targeted neural tissue or different placement within neural tissue. For example, FIG. 20C illustrates an embodiment of electrode 900 implanted in a non-central position within a ganglion of the sympathetic chain. The electrode 900A includes a proximal end 906 with tip 908 and anchors 910. A securing ring 920 (described above) is provided to secure the electrode body 902 to or relative to the DRG 40. The anchors 910 may be in a first or stowed position against the electrode body 902 during insertion through the DRG and then be moveable into a second or deployed position away from the electrode body 902. In the deployed position (FIG. 23D) the anchors 910 resist the movement of the electrode 900A out of the DRG 40. Numerous alternative anchor configurations are possible. Anchor 910 could be a series of individual struts arrayed in a circular pattern or struts with material between them similar to the construction of an umbrella. Anchor 910 could also be a single anchor.

The electrode 912 and perfusion ports 928 may be positioned along the electrode body 902 in any position suited for the delivery of neurostimulation and pharmacological agents. In the illustrated embodiment, the electrode 912 is positioned generally central within the DRG and the perfusion ports 928 are near the distal end of the electrode body 902. Other configurations are possible and more or fewer electrodes and perfusion ports may be used in other embodiments. For example, a perfusion port 928 could be located near the center of the DRG while an electrode 912 could be located elsewhere on the electrode body 902 so as to minimize the stimulation energy transmitted beyond the DRG and into surrounding tissue. One or more electrodes 912 could be positioned along the electrode body 902 so that the stimulation energy remained within (i.e., nearly completely attenuated within) the DRG 40 or other targeted neural tissue.

In one specific embodiment, the distal tip 908 has a point suited for piercing the dura layers to provide access for the electrode body 902 through the DRG. The tip 908 is advanced through the DRG until the anchors 910 pass through the opening formed by the tip 908 and extend as shown in FIG. 23D. Once the anchors 910 are through the DRG and extended, the electrode body 902 may be withdrawn slightly to engage the anchors 910 against the DRG dura. Thereafter, the securing ring 920 is advanced into position around the electrode body 902 and against the outer layer of DRG 40. When implanted into the DRG 40, electrode 900A is held in place using the anchors 910 and the securing ring 920. In other embodiments, the securing ring 920 may be used without the anchors 910. In another embodiment, the anchors 910 are used without the securing ring 920 or the securing ring 920 is replaced by another set of anchors that are adapted to secure the proximal end of the electrode body 902 to or in proximity to the DRG.

FIG. 24 is a table that includes several exemplary infusion pharmacological agents. The pharmacological agents are listed along the left side. Moving to the right, closed circles and open circles are used to indicate the level of support for using a particular pharmacological agent with a particular type of pain or other condition. Closed circles indicate evidence from controlled trials or several open-label trials and general acceptance or utility. Open circles indicate a less extensive base of evidence. For example in the treatment of restless leg syndrome (RLS), benzodiazepines have evidence of general acceptance or utility while gabapentin has a less extensive base of evidence. These and other pharmacological agents may be provided into the body to have a cooperative pharmacological result on the neural tissue(s) either alone or in combination with stimulation provided by embodiments of the present invention. In some embodiments, the pharmacological agent is provided at the stimulation site and in other embodiments the pharmacological agent is provided using a stimulation electrode embodiment adapted to deliver one or more pharmacological agents.

Consider the following specific example. Nociceptors express a specific subclass of voltage-gated sodium channel. These TTX-R $Na^+$ channels are believed to contribute significantly to action potential firing rate and duration in small-diameter sensory neurons (i.e., c-fibers). Embodiments of the present invention may provide the appropriate channel blocker to synergistically improve neurostimulation capabilities. For example, a combination stimulation and release of a pharmacological agent may be used to provide Na channel blockers directly within the dorsal root ganglia interfascicular space, adjacent to c-fiber or within a pharmacologically active position such that the agent interacts with the channel.

Figure 25:
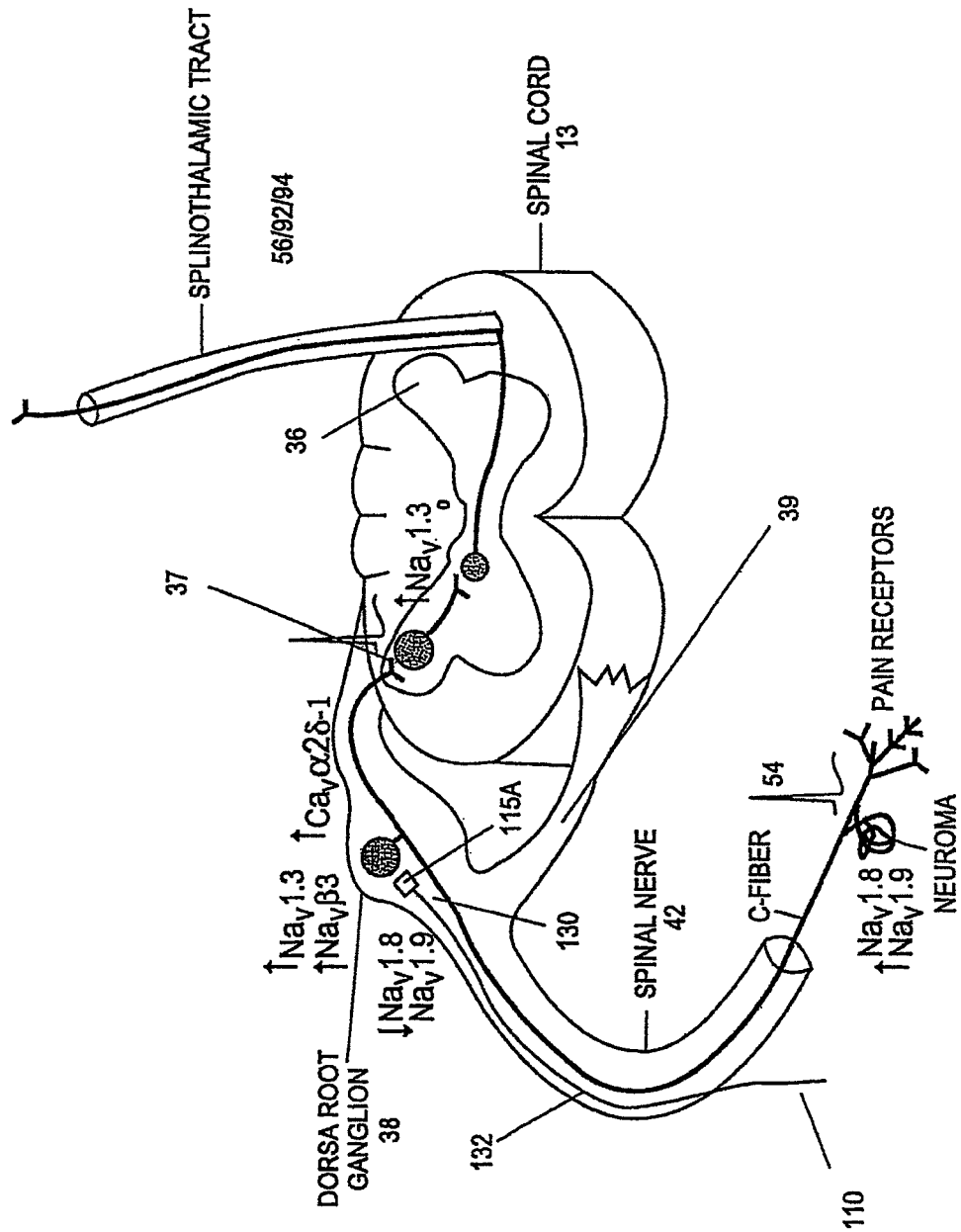
FIG. 25 is an illustration of $Na^+$ and $Ca^{2+}$ channel blocking targets to mitigate c-fiber activity.

Embodiments of the present invention also enable the advantageous use of ion channels in the nervous system as targets for pharmacological agents combined with selective direct stimulation. $Na^+$ channels and gabapentin sensitive $Ca^{2+}$ channels are upregulated after nerve-injury. Channel blockers can suppress abnormal C-fiber neural excitability. $Na^+$ and $Ca^+$ channel targets distributed along the pain pathway are illustrated in FIG. 25. Embodiments of the present invention advantageously utilize the specific anatomy and features of the dorsal root ganglia (DRG) to improve the efficacy of pharmacological agents. In one specific example, note that the DRG contains both TTX-sensitive $Na^+$ channels (Nav1.3), TTX-resistant $Na^+$ channels (1.8,1.9), and gabapentin sensitive $Ca^{2+}$ channels. FIG. 25 shows a number of dorsal root ganglia, peripheral nervous system and spinal cord afferent pain pathways. Note the alterations in voltage-dependent $Na^+$ and $Ca^{2+}$ channel subunits after chronic nerve injury associated with neuropathic pain. In addition, there is an increase in the expression of Nav1.3 channels and $Na^+$ channel 3 (Nav 3) and $Ca^{2+}$ channel 2-1 (Cav 2-1) subunits in dorsal root ganglion neuron cell bodies, and in the expression of Nav1.3 in second-order nociceptive neurons in the spinal cord dorsal horn 37. The tetrodotoxin-resistant $Na^+$ channel subunits Nav1.8 and Nav1.9 are also redistributed from dorsal root ganglion neuron cell bodies to peripheral axons and pain receptors at the site of injury. These changes are thought to result in spontaneous ectopic discharges and lower the threshold for mechanical activation that leads to paraesthesias, hyperalgesia and allodynia.

In one aspect of the present invention, these channels are the target of a stimulation provided by embodiments of the systems and stimulation methods of the present invention. The stimulation may include electrical stimulation alone, a pharmacological agent delivered directly or via the DRG, a pharmacological agent delivered directly or via the DRG in combination with electrical stimulation, or electrical stimulation of the DRG in combination with the delivery of a pharmacological agent elsewhere in the pain pathway. In one particular embodiment, delivery of a pharmacological agent elsewhere in the pain pathway is upstream of the dorsal root ganglion or the nerve root ganglion being stimulated. In another embodiment, delivery of a pharmacological agent elsewhere in the pain pathway is downstream of the dorsal root ganglion. In another specific embodiment, stimulation is provided to a nerve ganglion in the sympathetic nervous system and a dorsal root ganglion up stream of or otherwise positioned to influence or block signals originating from the nerve ganglion.

Alternative embodiments of the methods and systems of the present invention may be used to repair or assist in the repair of neurological tissue in the spinal cord.

In another aspect of the present invention, there is provided methods and systems for the selective neurostimulation of the dorsal root ganglia for the regeneration of neurological tissue. For example, electrical stimulation may be provided selectively to the DRG, a portion of the DRG or in proximity to the DRG with or without a pharmacological agent to produce conditions within the DRG to assist in, encourage or otherwise promote the regeneration of neurological tissue.

In a specific embodiment where pharmacological agents may be provided by embodiments of the present invention, there is provided a method and/or system to induce intraganglionic cAMP elevation for the regeneration of sensory axons utilizing the mechanisms suggested by Neumann S, Bradke F, Tessier-Lavigne M, Basbaum A I. in the article entitled, "Regeneration of Sensory Axons Within the Injured Spinal Cord Induced by Intraganglionic cAMP Elevation. (see Neuron. 2002 Jun. 13; 34(6):885-93, incorporated herein by reference in its entirety.) The work of Neuman et al. demonstrated the regeneration of the central branches of sensory neurons in vivo after intraganglionic injection of db-cAMP. Horizontal sections through a lesion site taken from db-cAMP-injected animals shows regenerating fibers. A neurostimulation electrode adapted for delivery of a pharmacological agent may be used for intraganglionic delivery of db-cAMP. Intraganglionic delivery of db-cAMP may be accomplished using any of the techniques described herein for the delivery of a pharmacological agent including, for example, a coating on all or part of an electrode body or the use of suitably positioned perfusion ports.

Figure 26:
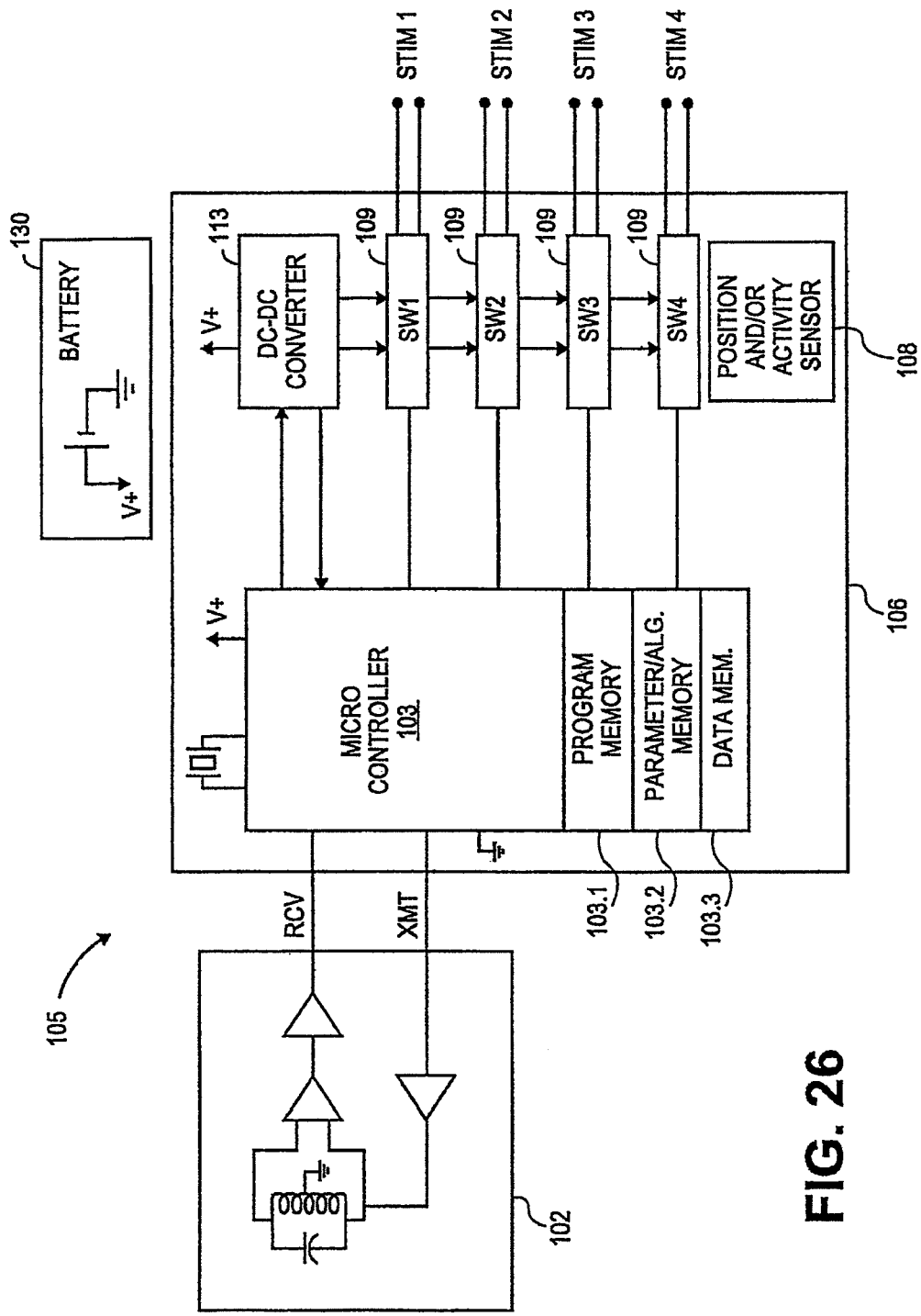
FIG. 26 is a schematic drawing of an embodiment of a pulse generator.

FIG. 26 illustrates an embodiment of a pulse generator 105 according to one aspect of the present invention. Similar to conventional stimulation pulse generators, communication electronics 102 have a receiver for receiving instructions and a transmitter for transmitting information. In one embodiment, the receiver and the transmitter are implantable in the body and adapted receive and transmit information percutaneously. The control electronics 106 includes a microcontroller 103 having conventional features such as program memory 103.1, parameter and algorithm memory 103.2 and data memory 103.3. A battery 130 is also provided and may be located with and part of the pulse generator (i.e., FIG. 27) or implanted at a location separate from the pulse generator (i.e., FIG. 28). Switches 109 are provided to couple stimulation energy from the DC-DC converter 113 to the stimulation sites (i.e., electrodes located at STIM1-STIM4) under the control of the microcontroller 103.

Programmable parameters are modified in accordance with transcutaneous RF telemetry information received by communication electronics 102. The telemetry information is decoded and used by the control electronics to modify the pulse generator 105 output as needed. The output of the pulse generator or a stimulation program may be modified dynamically. Pain often correlates to certain activities such as walking, bending or sitting. An activity level sensor may be used to detect the amount or degree of activity. The level of activity could be an input to dynamically modify the stimulation program to determine the appropriate level of stimulation. Alternatively or additionally, different pre-programmed stimulation algorithms may be designed for an individual patient based on that specific patient's pattern of activity. Pre-programmed stimulation algorithms may be stored in an appropriate medium for use by a stimulation system described herein. Conventional transcutaneous programming techniques may also be used to update, modify or remove stimulation algorithms.

Pain often correlates to certain positions such as standing or laying down. A position sensor may be used to detect position of the patient. The position of the patient could be an input to the stimulation control system to dynamically modify the stimulation program to determine the appropriate level of stimulation. One example of such a sensor is a multi-axis accelerometer. A conventional 3 or 4 axis accelerometer could be implanted into a patient or maintained on the patient to provide position, activity level, activity duration or other indications of patient status. The detected indications of patient status could in turn be used in determining stimulation level and pattern. The position sensor can be set up or calibrated once positioned or implanted on or in a person. The calibration aids the sensor in correctly recognizing the person's orientation and activity levels.

Optionally, a position sensor 108 is located within the same physical housing as implantable generator. If desired, the position sensor may be located elsewhere on the body in an implanted location or may be worn externally by the person. Position information from the position and/or activity sensor 108 is provided to the pulse generator 105 using suitable means including direct connections or percutaneous transmission. Although a number of embodiments are suitable, the preferred mode employs, by way of example and not to be construed as limiting of the present invention, one or more accelerometers to determine patient state including, at least, the ability to sense whether the person is erect or recumbent. Additionally, the position sensor could be adapted to provide an indication of activity or level of activity such as the difference between walking and running. In another embodiment, a position sensor 108 may be positioned to sense specific motion such as activity of a particular part of the body to detect specific movement of a body part or limb that, for example, is undergoing post-surgical physical therapy. Using this position sensor embodiment, when the person started activity related to physical therapy, the sensor would detect such activity and provide the appropriate stimulation. In additional alternatives, the position and/or activity sensor includes one or more multi-axis accelerometers.

As discussed above, microelectrode embodiments of the present invention have electrode sizes and surface areas that are considerably smaller that conventional stimulation electrodes so that they may be implanted according to the methods described herein. As discussed above, the smaller electrode size leads to increased electrical impedance and a need for voltages above 15 volts, above 20 volts or even up to as much as 40 volts in order to provide sufficient stimulation current to the microelectrode. Conventional pulse generators employ capacitive switching arrays to provide voltages up to 12v from a 3v battery for conventional neurostimulation systems. It is believed that the large electrical losses introduced by the switches used in conventional capacitive systems would render them incapable of providing sufficient current to drive the microelectrodes of the present invention. As such, the pulse generator 105 departs from conventional pulse generators by using a DC-DC converter to multiply the battery voltage up to the ranges needed to operate the stimulation systems described herein.

In one embodiment of the pulse generator of the present invention, there is at least one switch 109 connected to at least one implantable electrode having an impedance greater than 2,500 ohms. There is also provided a DC-DC converter adapted to provide a stimulation signal to the at least one implantable electrode under the control of the controller 103 that is configured to control the output of the DC-DC converter 113. Additionally, the pulse generator, the at least one switch, the DC-DC converter and the controller are implantable in the body. In another aspect, the controller 103 controls the output of the DC-DC converter 113 to deliver a stimulation signal according to an algorithm for blocking pain signals. In one aspect, the DC-DC converter is configured to provide a voltage from 0 volts to 30 volts. In another aspect, the DC-DC converter is configured to provide a voltage from 0 volts to 40 volts.

Figure 27:
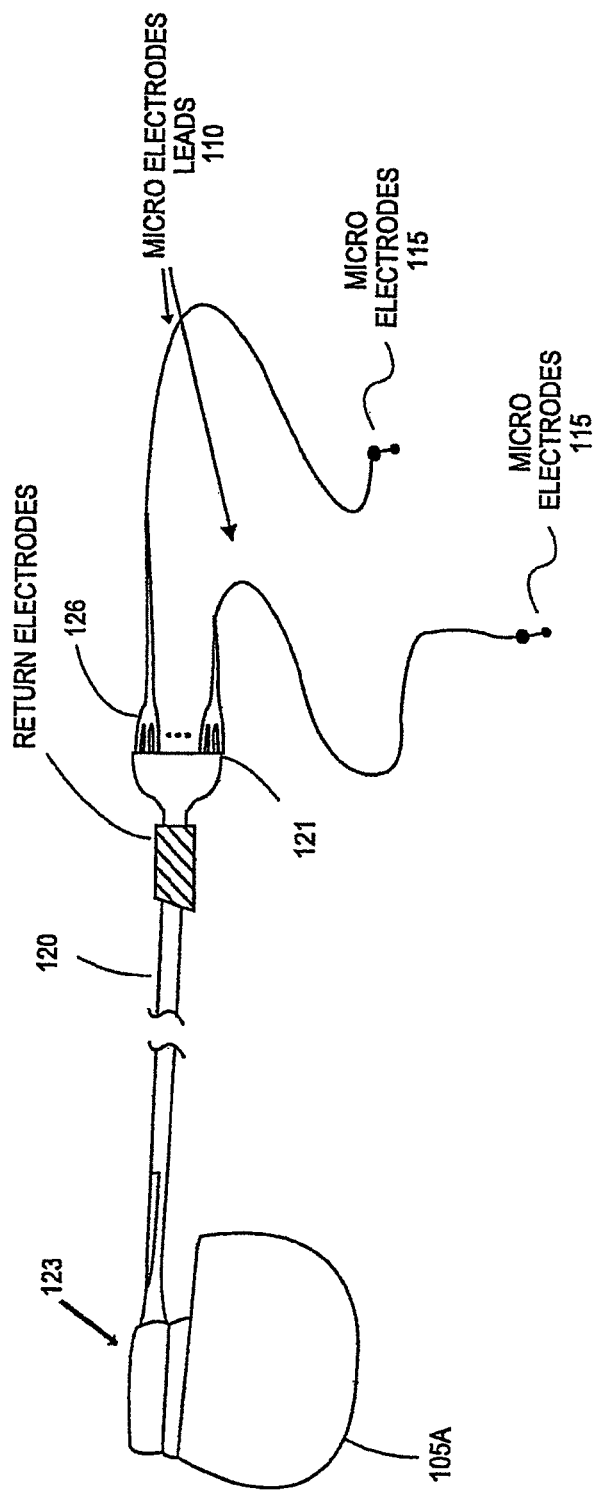
FIG. 27 is a schematic drawing of an electrode connector embodiment.

FIG. 27 illustrates one embodiment of an electrode connector according to the present invention. The electrode connector 120 has a proximate end 123 adapted to connect with a pulse generator 105A and distal end 121 adapted to connect with the electrode connector 126. The electrode connector distal 121 end is adapted to connect to a plurality of microelectrode leads 110/connectors 126 depending upon how many microelectrodes 115 are used. Optionally, a portion of the electrode connector 120 may be configured as a return electrode in some embodiments.

In conventional stimulation systems, the stimulation electrode leads are connected directly to the pulse generator resulting in an implantation procedure that includes tunneling multiple leads from the pulse generator to each electrode. This technique has the added shortcoming of multiple connection points into the pulse generator each one required to be sealed and a source of potential wear. In contrast, embodiments of the present invention utilize fine micro leads 110 and microelectrodes 115 that would likely hinder the success of conventional tunneling procedures. Rather than the conventional tunneling of multiple electrodes and their leads, the electrode connector 120 is a flexible electrical connector used to bridge the distance between the site where the pulse generator is implanted and the one or more stimulation sites where the microelectrodes will be implanted. It is to be appreciated that the electrode connector is sufficiently long to extend from the pulse generator implanted at a first anatomical site to the microelectrode implanted at a second anatomical site.

The pulse generator 105A differs from conventional pulse generators in that is has a single connection point to the electrode connector rather multiple connection points to each stimulation electrode. Advantageously, the fine micro leads and microelectrodes are thus implanted and span a distance now made much shorter by the electrode connector 120. The microelectrode leads 110 now only span a distance between the electrode connector distal end 121 and the microelectrode 115 at the nerve root ganglion implantation site.

FIG. 27 also illustrates an embodiment of a stimulation component. The stimulation component includes a proximal connector 126, a distal electrode 115 configured to be implanted within the body at a stimulation site and an electrical lead 110 connected to the proximal connector and the distal electrode. The distal electrode may be, for example, a mono-polar electrode or a bi-polar electrode. In some embodiments, there is also provided a strain relief mechanism in proximity to the stimulation site and/or a fixation element adapted to reduce the amount of movement of the electrical lead proximal to a fixation point in an anatomical structure proximal to the stimulation site (See e.g., 12A/B, 13A, 14A). The proximate connector 126 is adapted to connect with the electrode connector distal end 121.

In still further embodiments, the stimulation component may also include an anchoring mechanism proximal to the distal electrode (e.g., deformable anchor 117 in FIGS. 13B, 14B). In some embodiments, the anchoring mechanism is adapted to anchor the distal electrode within the stimulation site and may optionally be integrally formed with the distal electrode. The anchoring mechanism is formed from a polymer, a silicone or other flexible, biocompatible material. In some embodiments, the anchoring mechanism and/or the electrode body is formed from a flexible, biocompatible material that has been adapted to include a radio opaque material. Suitable biocompatible materials may biocompatible polymeric biomaterials featuring radio-opacity or other polymeric biomaterials made radio-opaque through addition of a 'contrast agent', usually a non-toxic salt or oxide of a heavy atom.

FIG. 28 illustrates another stimulation system embodiment of the present invention. In the illustrative embodiment, a pulse generator 2806 is connected to four individually controlled microelectrodes 115 implanted in four separate nerve root ganglion, here dorsal root ganglions DRG1 through DRG4. The innovative stimulation system of FIG. 28 differs from conventional stimulation systems in that the battery 2830 is separate from the pulse generator 2806. An electrical connection (e.g., wires 2804) suited to carry the battery power extends from the battery 2830 to the pulse generator 2806. A microelectrode lead 10 is connected proximally to the pulse generator 2806 using connectors 2812 and distally to a microelectrode 115. The pulse generator 2806 includes similar functionality of earlier described pulse generator embodiments such as a DC-DC converter configured to provide a voltage from 0 volts to 30 volts, a voltage from 0 volts to 40 volts or other suitable voltage ranges to drive microelectrodes described herein. The battery 2830, the pulse generator 2806 separate from the battery, the electrical connections 2804, the microelectrode lead 1110 and the microelectrode 115 are adapted to be implanted in the body.

Figure 30:
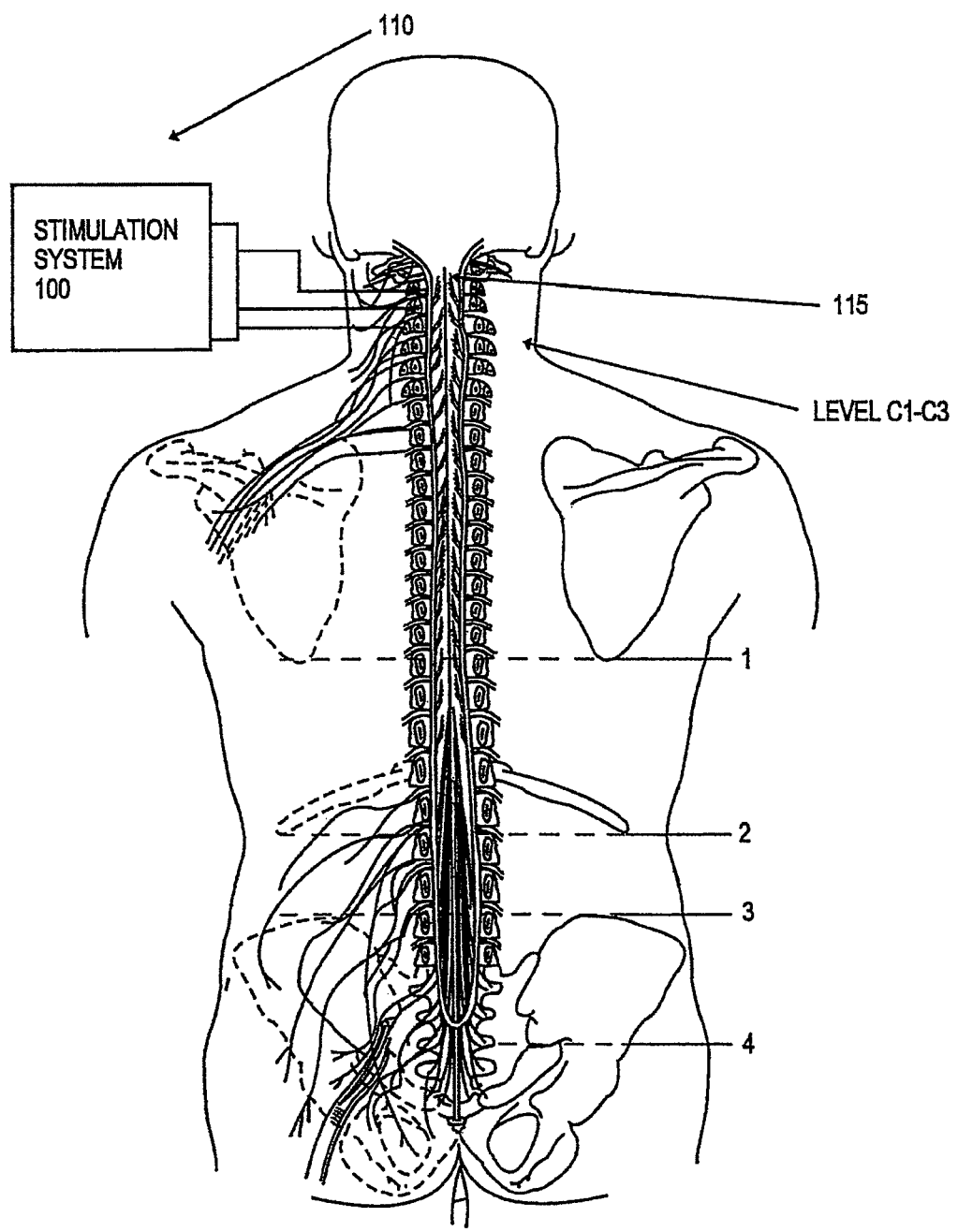
FIG. 30 is an embodiment of a stimulation system adapted to treat conditions in spinal levels C1-C3.

Additional embodiments of the local pulse generator 2806 have a compact size that enables implantation of the pulse generator 2806 in proximity to the stimulation site. Implanting the local pulse generator 2806 closer to the implantation site of the microelectrodes 115 desirably allows the use of shorter microelectrode leads 110. Embodiments of the pulse generator 2806 are sufficiently small to allow implantation in the back near the spinal levels to be stimulated, the upper back near the C1-C3 levels for migraine relief (FIG. 30). In one specific embodiment, the pulse generator 2806 has an overall volume of less than 200 mm$^3$. In another specific embodiment, at least one dimension of the pulse generator 2806 is 2 mm or less or at least one dimension of the pulse generator 2806 is 10 mm or less.

One embodiment of a multiple pulse generator system is illustrated in FIG. 29. The multiple pulse generator embodiment is similar to the system of FIG. 28 with the addition of a second pulse generator 2806B connected to the first pulse generator 2806A at connection points 2810 using connectors 2814. As with the earlier system, the second pulse generator 2806B is separate from the battery 2830. Additionally, there are provided microelectrode leads 110 connected proximally using connectors 2812 to the second pulse generator 2806B and distally to microelectrodes 115. The microelectrodes 115 are implanted within nerve root ganglia, here, dorsal root ganglia at implantation sites DRG5-DRG8. FIG. 29 illustrates eight implanted electrodes in separate implantation sites that could include dorsal root ganglion, nerve root ganglion of the sympathetic nervous system or other stimulation sites within the body.

It is to be appreciated that in one aspect the pulse generator 2806 and the second pulse generator 2806B are independently programmable. In another aspect, the pulse generator 2806A and the second pulse generator 2806B are adapted to operate in a master-slave configuration. Numerous coordinated stimulation patterns are possible for each electrode of a pulse generator or of all the electrodes in the system. In still further aspects, the activation of one microelectrode is coordinated with the activation of a second microelectrode. In one specific aspect, the microelectrode and the second microelectrode are activated by the same pulse generator. In another specific aspect, the microelectrode is activated by the pulse generator 2806A and the second microelectrode by the second pulse generator 2806B in a coordinated manner to achieve a therapeutic outcome. For example, the microelectrode is active when the second microelectrode is active or the microelectrode is inactive when the second microelectrode is active. In still further embodiments, the microelectrode is implanted in a dorsal root ganglion and the second microelectrode is implanted in a nerve root ganglion of the sympathetic nervous system. It is to be appreciated that the systems of FIGS. 27 and 28 may be configured as discussed above with regard to FIGS. 3-7.

In additional alternative aspects, specific embodiments of the present invention may be used to provide direct stimulation alone or in combination with released therapeutic agents as described herein for the treatment of headaches, migraine etc. As such, embodiments of the present invention may be used to provide direct, selective DRG, spinal cord and/or peripheral nervous system stimulation (using stimulation alone or in combination with the delivery of a therapeutic agent as described herein) to all, part or a combination of the C1-C3 levels to provide relief reduction or mitigation of pain resulting from headache, migraine or other such related conditions. There is provided a method of stimulating neural tissue to treat a condition by stimulating an electrode implanted to stimulate only a dorsal root ganglion on a spinal level wherein the stimulation treats the condition. As illustrated in FIG. 30, the spinal level comprises C1, C2 or C3 and the condition is a headache, or more specifically, a migraine headache.

Figures 31A, 31B:
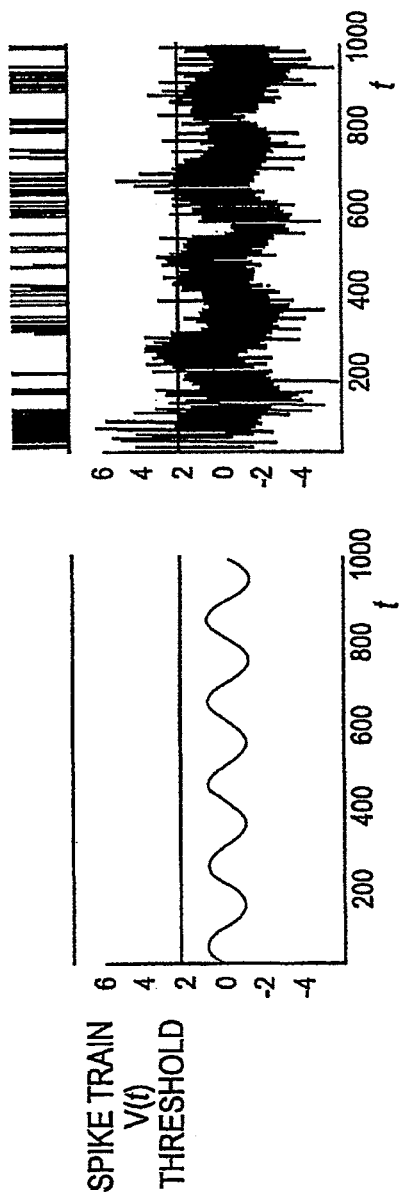
FIGS. 31A and 31B illustrate, respectively, the result of stimulation provided by embodiments of the present invention to increase sub-threshold signals above a threshold level.

In another alternative aspect, embodiments of the present invention provide sensory augmentation as a treatment for diabetic neuropathy. In one embodiment, direct stimulation of the DRG, spinal cord and/or peripheral nervous system using the techniques described herein are provided to stimulate or otherwise generate a type of stochastic resonance that will improve, enhance or provide added neurological stimulation. Stochastic resonance is the addition of noise to a system to improve signal clarity. For example, the introduction of direct neurological stimulation to the appropriate DRG, group of DRG, the spinal cord and/or peripheral nervous system may provide, for example, improved vestibular balance or other improvement or mitigation of a condition induced by diabetic neuropathy. The added neurological stimulation (either stimulation alone or in combination with therapeutic agent(s)) may be used, for example, to improve the nerve fiber function of nerve fibers damaged, improperly functioning or otherwise impaired as a result of diabetic neuropathy. Exemplary stimulation patterns induced utilizing direct stimulation techniques described herein to help raise the sub-threshold signal (FIG. 31A) to or above the threshold level (FIG. 31B).

Figure 32:
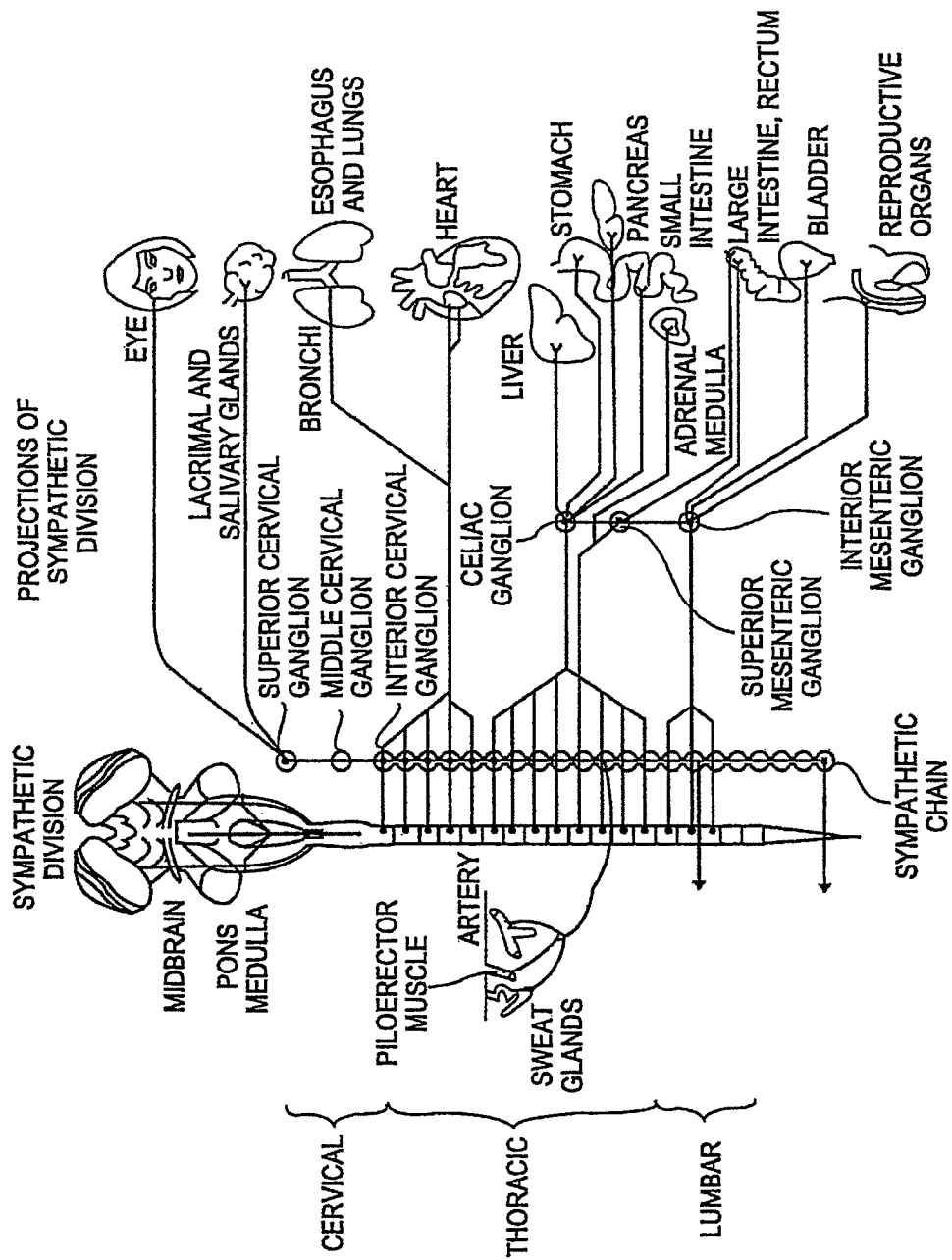
FIG. 32 is an illustration of the sympathetic nervous system.

In other embodiments of the present invention there are provided methods of treating physiological disorders by implanting at least one stimulation electrode at a specific location along the sympathetic nerve chain. Preferably, the present invention provides a method of therapeutically treating a variety of physiological disorders or pathological conditions by surgically implanting an electrode adjacent or in communication to a predetermined site along the sympathetic nerve chain on the affected side of the body or, if clinically indicated, bilaterally. FIG. 32 illustrates a schematic of the autonomic nervous system illustrating sympathetic fibers and parasympathetic fibers, including several nerve root ganglion.

Accordingly, embodiments of the present invention may be used in conjunction with other neurostimulation techniques by combining an upstream stimulation using specific DRG stimulation of the present invention with another stimulation acting downstream of the DRG stimulation. As used herein, downstream and upstream refer to pathways closer to the brain (i.e., upstream) or further from the brain (i.e., downstream). For example, several stimulation techniques are described by Rezai in US Patent Publication 2002/0116030 and U.S. Pat. No. 6,438,423 and by Dobak in publication 2003/0181958, all of which are incorporated herein by reference. In specific aspects, embodiments of the present invention may be used to provide electrical and combinational (i.e., with a pharmacological agent) stimulation of the sympathetic nerve chain as described by Rezai alone (i.e., using the appropriate DRG stimulation or implanting directly into a nerve root ganglion.). Alternatively or additionally, embodiments of the present invention provide specific, direct stimulation of one or more DRG are used in combination with the stimulation techniques described by Rezai (i.e., conventional stimulation of the sympathetic chain using one or more of Rezai's techniques).

Figure 33:
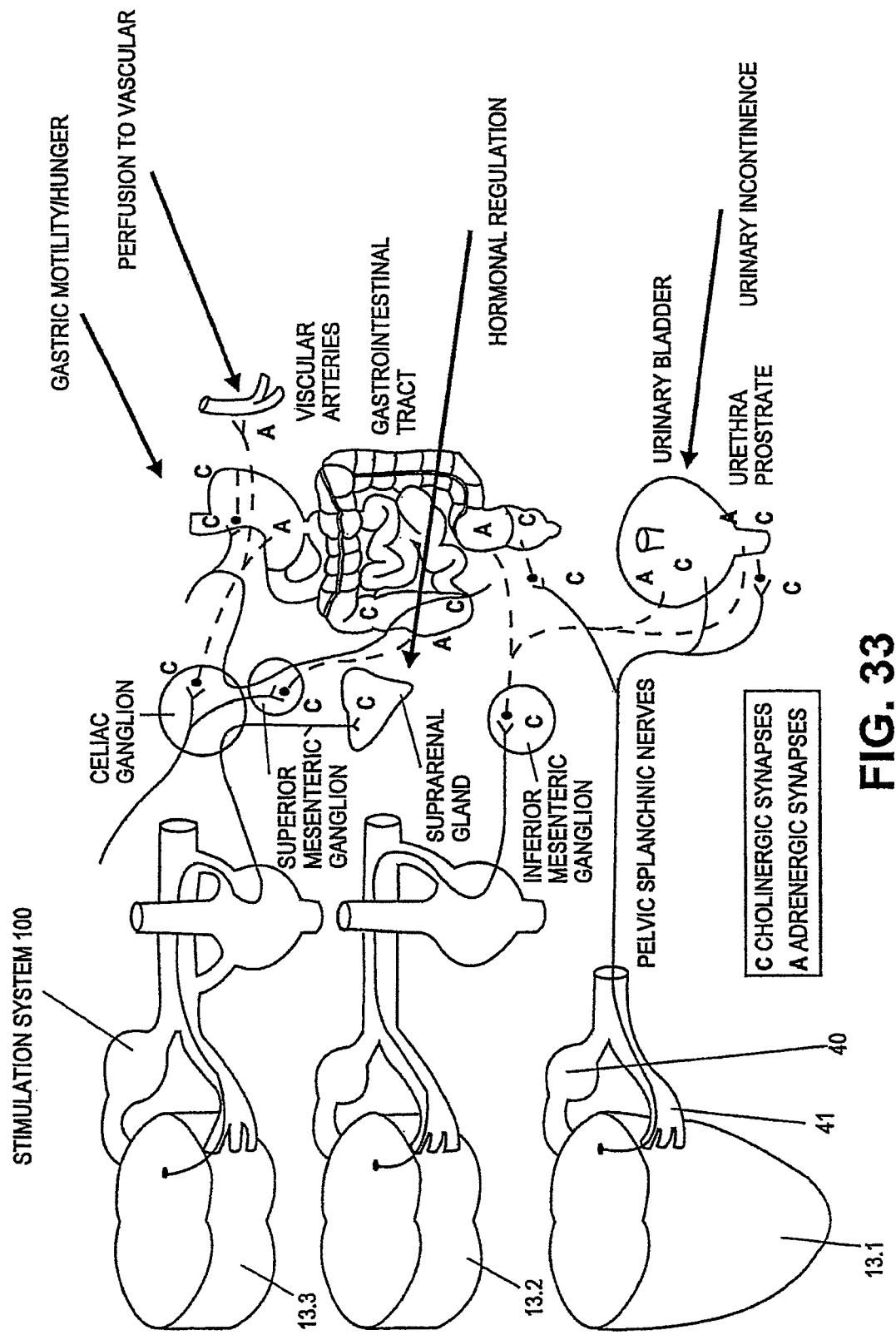
FIG. 33 is an illustration of a portion of sympathetic nervous system neuromodulated by a stimulation system embodiment of the present invention.

FIG. 33 illustrates how embodiments of the present invention may be advantageously utilized for neurostimulation of the sympathetic chain using direct stimulation of the associated DRG. This aspect of the present invention takes advantage of the anatomical placement of the DRG relative to the sympathetic chain in conjunction with gate control theory described herein to direct DRG stimulation for control of the sympathetic system. Thus, selective neurostimulation techniques of the present invention may be advantageously employed to, for example, provide and/or augment therapeutic tools in regards to weight control, hormonal regulation, vascular perfusion, etc. Additional alternative embodiments include the use of specific stimulation to provide organ system autonomic modulation. Through implantation of stimulation electrodes and systems of the present invention to stimulate the appropriate DRG upstream of the associated portion(s) of the sympathetic chain, the associated system may be controlled, modulated or influenced utilizing the electrical and/or pharmacological agent stimulation techniques described herein.

Figure 34:
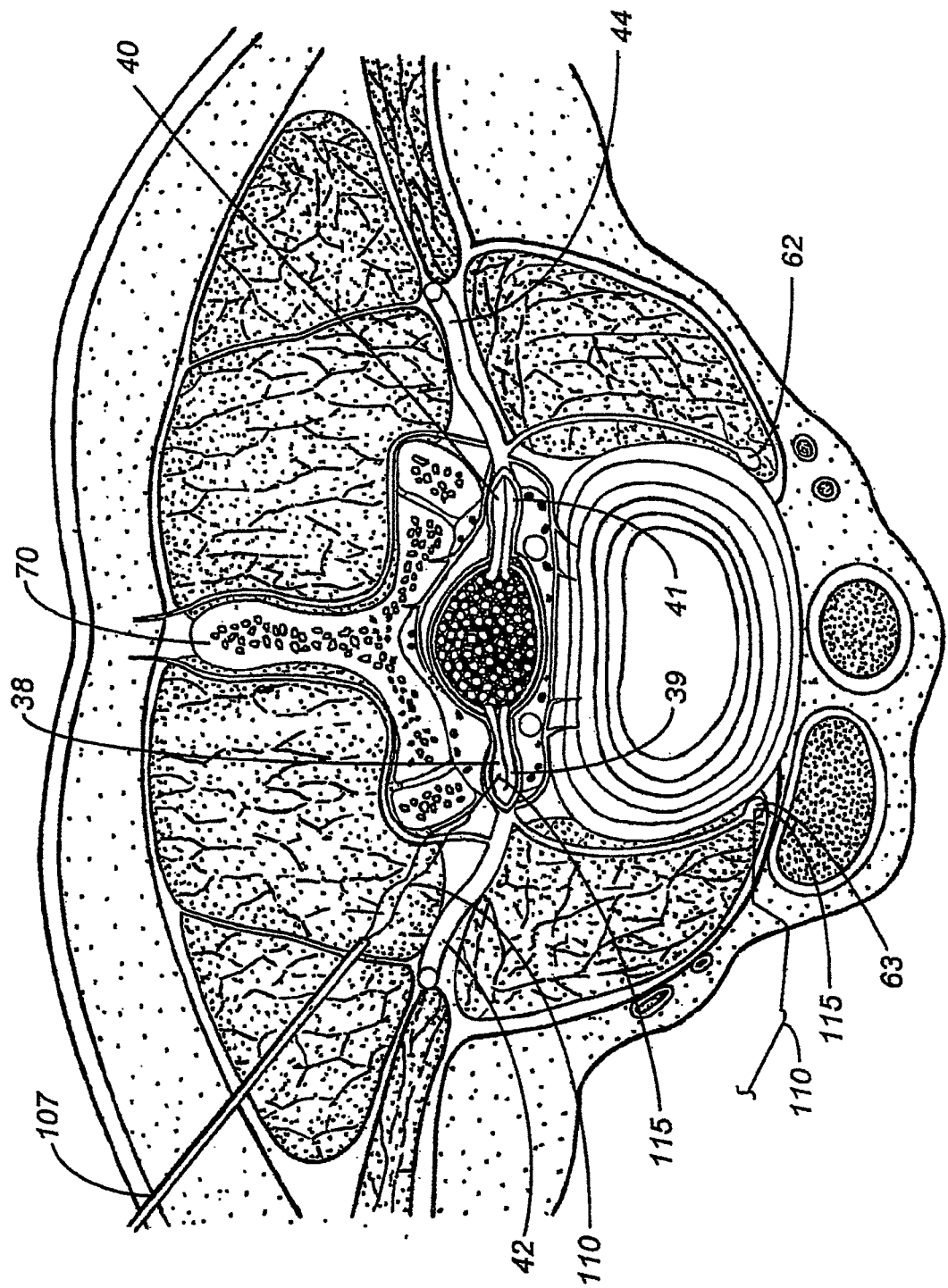
FIG. 34 is an illustration of embodiments of the present invention implanted for the direct stimulation of a single sympathetic nerve ganglion and a single dorsal root ganglion on the same spinal level.

In one specific example, by stimulating the DRG 40 associated with spinal level 13.3, the portion of the sympathetic chain associated with hormonal regulation may be altered, modified, influenced or controlled. Similarly, by stimulating the DRG 40 associated with spinal level 13.2 and/or level 13.1, the portion of the sympathetic chain associated with the gastrointestinal tract, or urinary incontinence (i.e., urinary bladder, urethra, prostate, etc.) may be altered, modified, influenced or controlled. Additionally, the direct stimulation techniques described herein may be used to directly stimulate individual nerve ganglion of the sympathetic nervous system, such as, for example, the celiac ganglion, superior mesenteric ganglion, inferior mesenteric ganglion and others listed in FIGS. 32, 33 or known to those of ordinary skill. It is to be appreciated that the stimulation systems, pulse generators and microelectrodes and other components are modified and sized as needed to allow for direct stimulation of the ganglion including implanting into the ganglion or within adjacent nerve sheaths leading to the ganglion. FIG. 34 illustrates the combined direct stimulation of a DRG 38 with microelectrode 115 as well as a suitable sized microelectrode 115 implanted in a sympathetic nerve root ganglion 63. The electrodes in FIG. 34 may stimulated independently or in a coordinated fashion to achieve the desired clinical outcome or other desired result. Similar to the discussion above for electrode placement in the DRG, electrode placement for the sympathetic chain may also be unilateral, bilateral, on adjacent portions of the chain or separate portions of the chain as needed.

One aspect of the present invention is a method of modulating a neural pathway in the sympathetic nervous system including stimulating a spinal dorsal root ganglion upstream of at least one ganglion of the sympathetic nerve chain to influence a condition associated with the at least one ganglion of the sympathetic nerve chain. In one specific embodiment, stimulating a spinal dorsal root ganglion comprises stimulating a spinal dorsal root ganglion upstream of at least one ganglion of the sympathetic nerve chain to influence functional activation of a bodily system associated with the at least one ganglion along the sympathetic nerve chain, to influence functional activation of an organ associated with the at least one ganglion along the sympathetic nerve chain, or to influence functional inhibition of a bodily system associated with the at least one ganglion along the sympathetic nerve chain. In specific embodiments, the ganglion of the sympathetic nerve chain is a cervical ganglion, a thoracic ganglion, or a lumbar ganglion.

In another aspect, the method of modulating a neural pathway in the sympathetic nervous system includes application of stimulation using an electrode exposed to the spinal dorsal root ganglion epinurium. In another aspect, the application of stimulation is performed using an electrode within the dorsal root ganglion. Alternatively, or in addition, stimulation may be applied to at least one ganglion along the sympathetic nerve chain using an electrode exposed to the at least one ganglion or using an electrode implanted within the at least one ganglion or applying stimulation along the sympathetic nerve chain.

Figure 35:
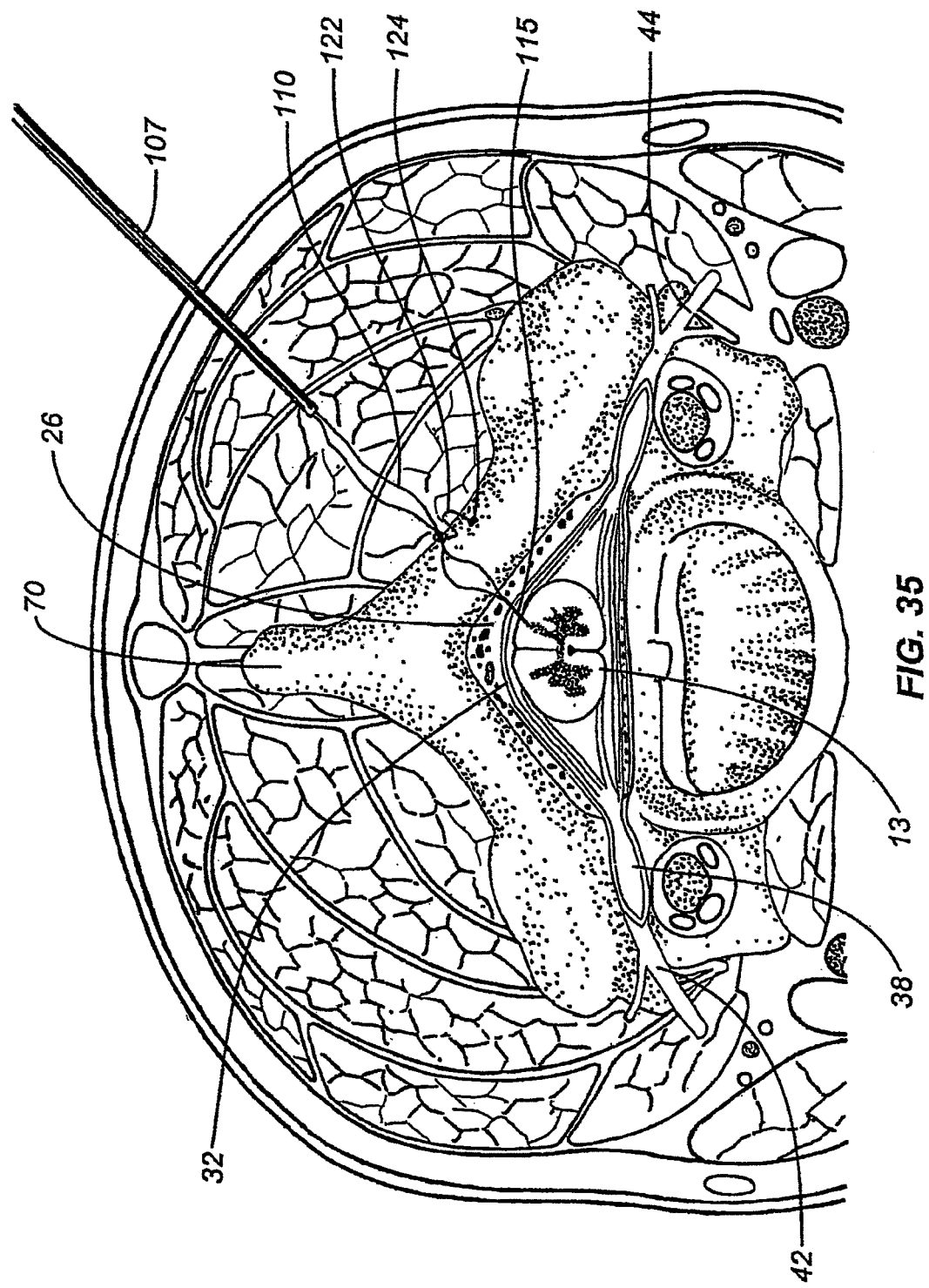
FIG. 35 is an illustration of an embodiment of the present invention implanted for the direct stimulation of the spinal cord.
Figure 36:
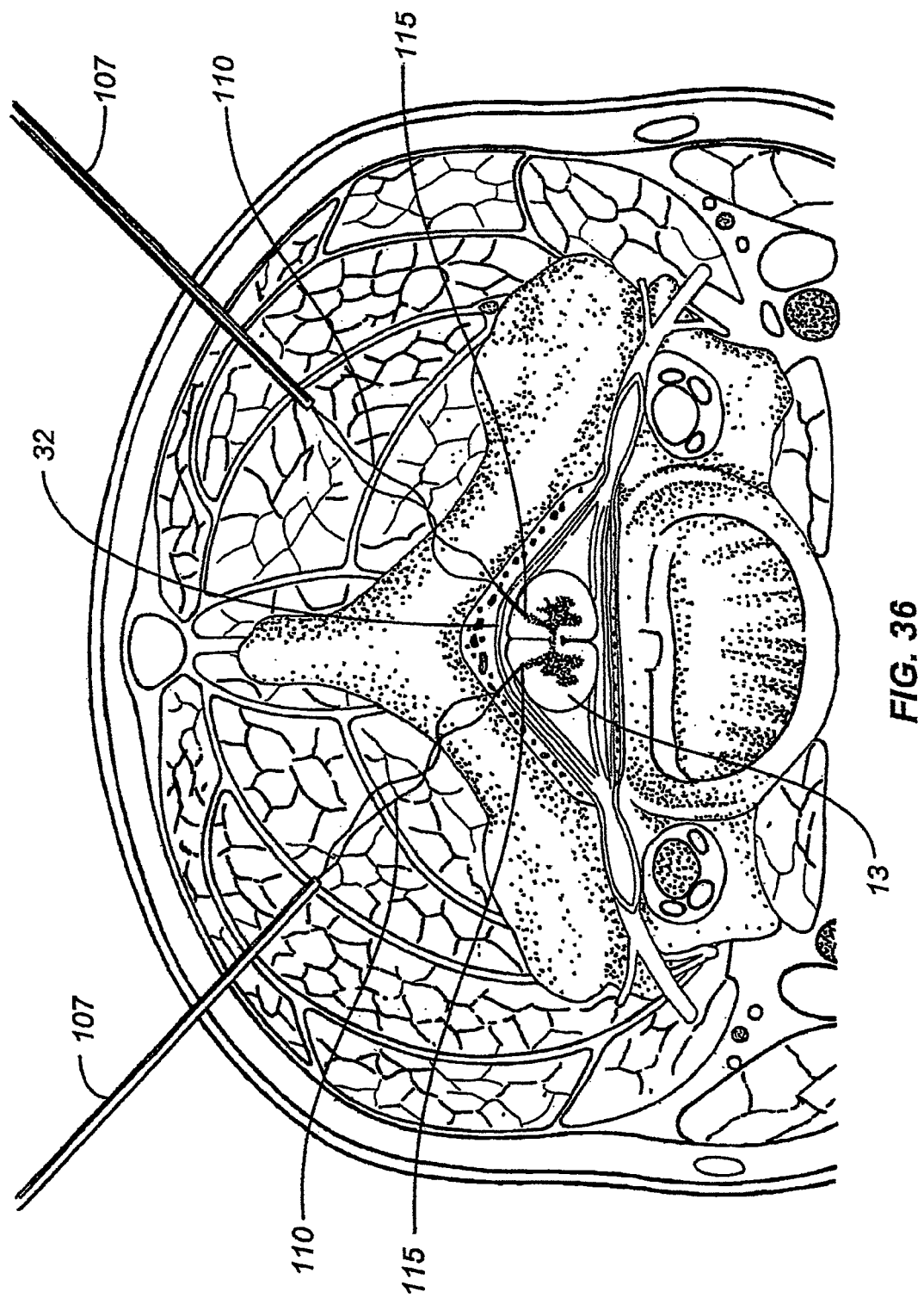
FIG. 36 is an illustration of two embodiments of the present invention implanted for the direct stimulation of the spinal cord.
Figure 37:
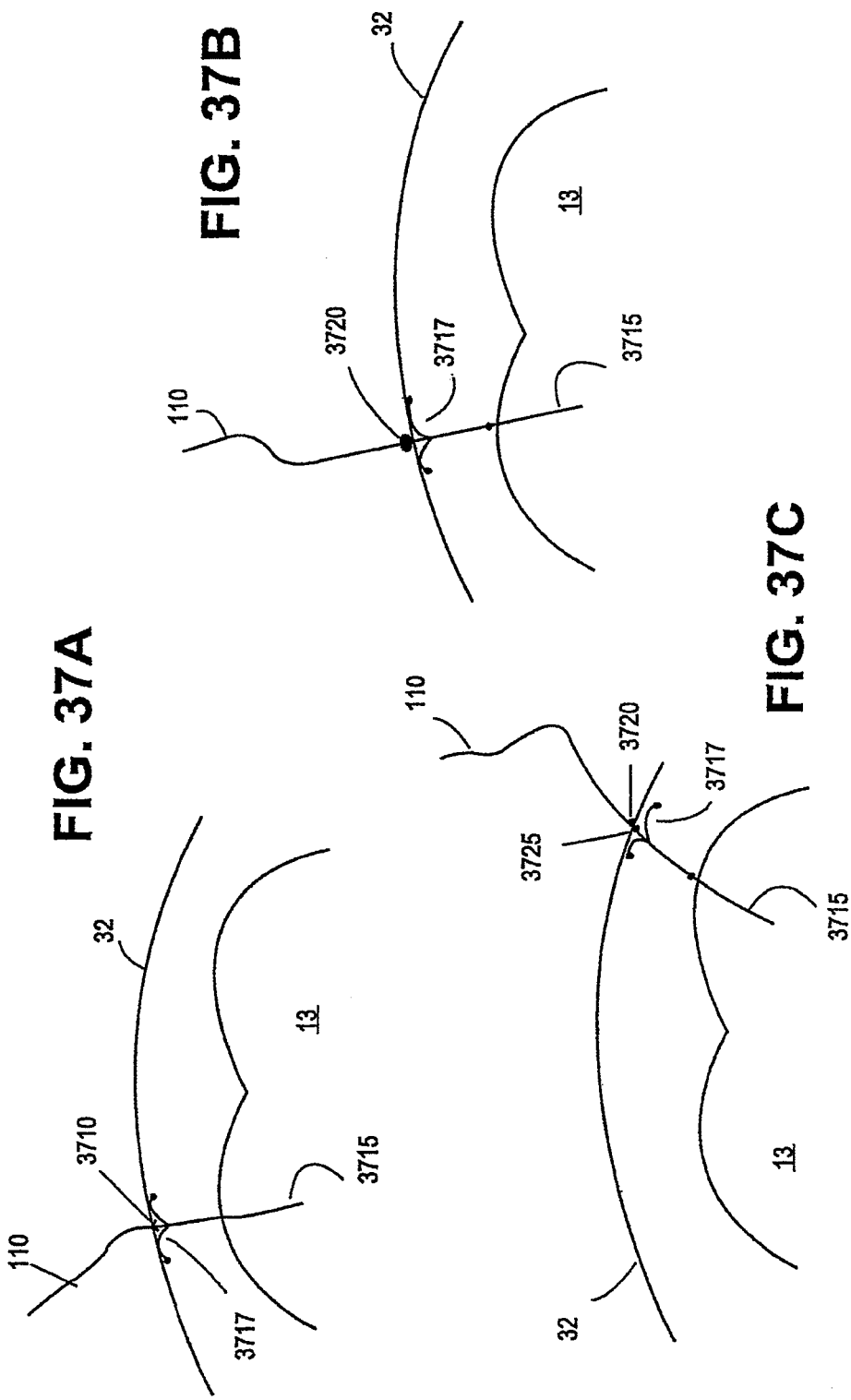
FIG. 37A-37C illustrate sealing embodiments used when implanting electrodes into the spinal cord.
Figure 38:
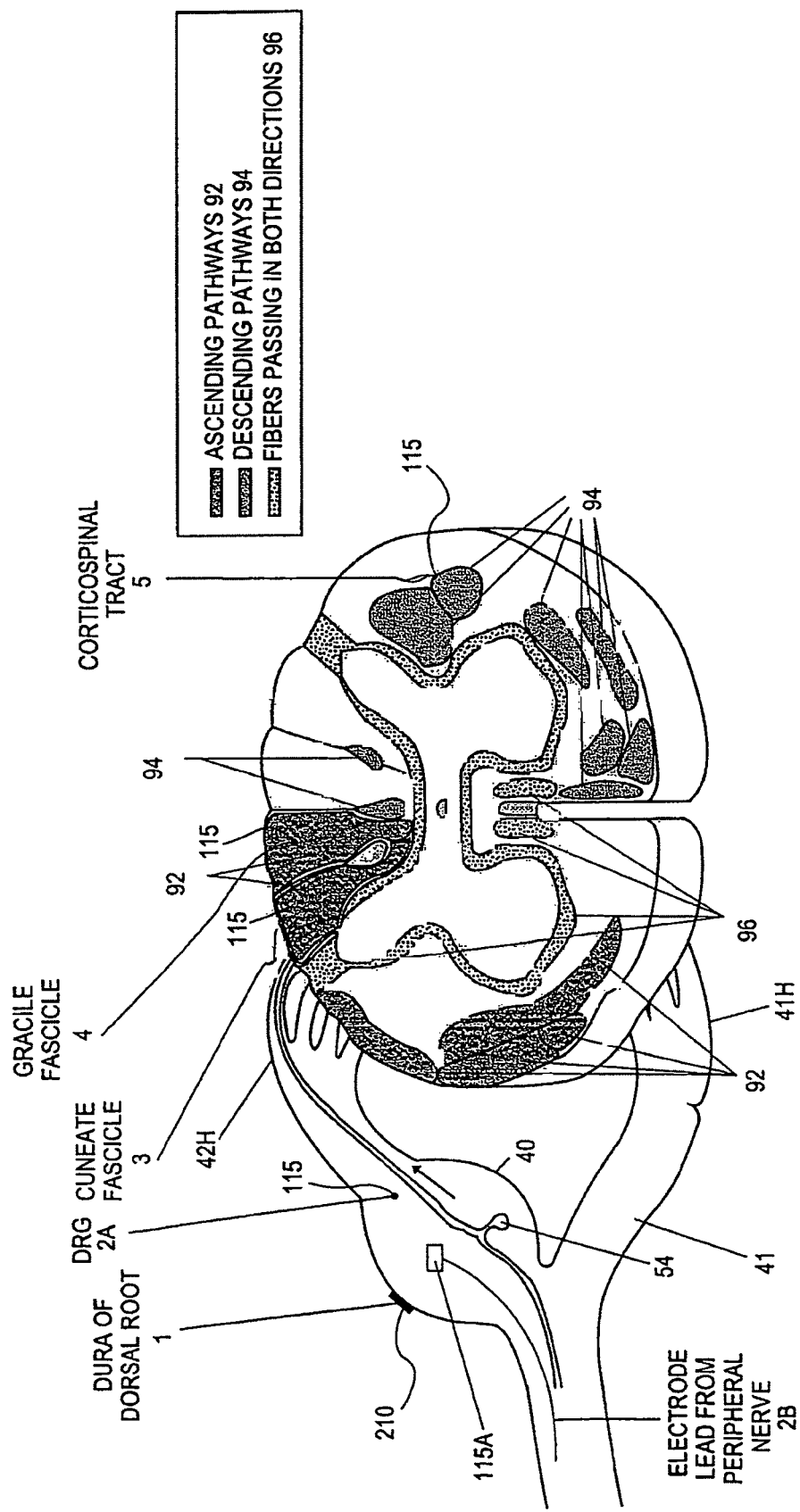
FIG. 38 summarizes numerous alternative embodiments of the stimulation system of the present invention as applied to different portions of the spine and dorsal root ganglion.

FIGS. 35, 36 and 38 illustrate how embodiments of the stimulation system, methods and microelectrodes described herein may be advantageously employed for direct stimulation of the spinal cord. Those of ordinary skill will appreciate that a pulse generator, battery and other stimulation system components described above would be used to drive the spinal electrodes described herein. As illustrated in FIG. 35, a microelectrode 115 has been advanced through the epidural space 26 through the dura matter 32 and into the spinal cord 13. In the illustrated embodiment the electrode 13 is positioned in the spinal cord 13 with an anchor 124 in the vertebral body 70 along with a strain reducing element 122 (i.e., a coil of microelectrode lead 110). FIG. 36 illustrates two electrodes implanted into the spinal cord 13 for direct stimulation. Optionally or additionally, anchors and seals may also be provided and are further described below with regard to FIGS. 37A, B and C. While the illustrative embodiments show an electrode implanted at a depth into the spinal cord, electrodes may be surface mounted as well. For example, electrodes may be placed in positions that just pierce the outer surface up to a depth of 1 mm or alternatively at depths from 2 mm to 12 mm or as otherwise needed to accomplish the desired stimulation therapy or treatment.

Embodiments of the present invention provide a method of stimulating the spinal cord that includes implanting an electrode into the spinal cord and providing stimulation energy to spinal cord fibers using the electrode. In one aspect, the stimulation energy is provided to the spinal cord using the electrodes at a level below the energy level that will ablate or otherwise damage spinal cord fiber. In specific embodiments, the spinal microelectrode is implanted into the cuneate fascicle, the gracile fascicle, the corticospinal tract, an ascending neural pathway, and/or a descending neural pathway.

In another specific embodiment, a method for stimulation of the spinal cord includes piercing the spinal dura matter and placing an electrode into contact with a portion of the intra-madullary of the spinal cord. Additionally, the portion of the intra-madullary of the spinal cord may include the cuneate fascicle, the gracile fascicle, the corticospinal tract. Additionally or optionally, the electrode may be implanted into the portion of the intra-madullary of the spinal cord including a portion of the intra-madullary that controls pain from the upper extremities, the lower extremities, an upper spinal cord pain pathway, or a lower spinal cord pain pathway. Additionally or optionally, an electrode may be implanted into and directly stimulate a portion of the intra-madullary of the spinal cord that influences control of an organ, such as for example, autonomic bladder stimulation, or other body function.

FIGS. 37A-37C illustrate alternatives to sealing the spinal dura 32 after the dura is pierced during the electrode implantation procedure. In one aspect, the present invention provides methods of forming an opening in the spinal dura, passing the electrode through the opening in the spinal dura and sealing the opening in the spinal dura 32. Additionally, atraumatic anchors 3717 may also be provided distal to the electrode 3715 to assist with maintaining electrode position in the spinal cord 13 after implantation, as well as resist pull out. The anchors 3717 may be formed from any suitable biocompatible material that is flexible and will not contaminate the surrounding cerebral spinal fluid. In FIG. 37A, a single fibrous seal 3710 is disposed distal to the anchor 3717 against the interior wall of the dura 32. Examples of suitable seal materials for seals 3710, 3720 and 3725 include, for example, tissue glue, synthetic fibers, gel foam, hydrogels, hydrophilic polymers or other materials having fabric characteristics suited to sealing. Each of the seals described herein may be separate from or integrally formed with an anchor 3717. FIG. 37B illustrates an embodiment where a seal 3720 is provided on the exterior wall of the dura 32. FIG. 37C illustrates the use of two seals. A seal 3725 against the inner dura wall and a seal 3720 against the outer dura wall. Examples of suitable seal materials for seals 3720, 3725 include: vascular suture pads, polyurethane, fluorinated polymers, biodegradable polymers such as PLA/PGLA. Seals as described herein are adapted to prevent CSF leakage through the hole in the dura formed during electrode implantation. In alternative embodiments, the component passing through the dura after implantation (either a microelectrode shaft or microelectrode leads depending upon design) has a material or surface that engages with the seal 3717, 3720 and assists in sealing the dura. In one specific embodiment, the seal 3720 could be a fabric pad such as a vascular suture pad and the seal 3725 could be a polymer or a form of tissue glue.

FIG. 38 illustrates and summarizes numerous specific targets for stimulation and electrode placement within the nervous system. Nerves on only one side of the spinal cord are shown. FIG. 38 illustrates several alternative microelectrode placement locations depending upon desired stimulation, neural response or treatment of a condition. Embodiments of the present invention employ appropriately small sized microelectrodes thereby enabling the selective stimulation of numerous specific portions of the nervous system in addition to the specific embodiments described herein. Microelectrodes are illustrated in the DRG dura (1), within the DRG through the dura (2A), within the DRG by traversing the peripheral nerve sheath (2B). The spinal cord may be stimulated by implanting electrode(s) into ascending pathways 92, descending pathways 94 or fibers 96. Spinal cord stimulation may also be accomplished by placing microelectrodes into specific spinal cord regions such as the cuneate fascicle 3, gracile fascicle 4 or the corticospinal tract 5. Additionally, electrodes may be placed in the spinal cord near the root entry into the cord, such as dorsal root 42H and ventral root 41H. Embodiments of the present invention also enable microelectrode placement and direct stimulation can be advantageously positioned and applied so as to influence and/or control bodily function(s).

In some embodiments, direct stimulation refers to the application of stimulation or modulation energy to neural tissue by placing one or more electrodes into contact with the targeted neural tissue. In some specific embodiments, contact with the targeted neural tissue refers to electrode placement on or in a nerve ganglion. In other embodiments, one or more electrodes may be placed adjacent to one or more nerve ganglion without contacting the nerve ganglion. Electrode placement without contacting the nerve ganglion refers to positioning an electrode to stimulate preferentially only a nerve ganglion. Stimulation of preferentially only a nerve ganglion refers to electrode placement or electrode energy delivery to targeted neural tissue without passing the neurostimulation or modulation energy through an intervening physiological structure or tissue.

Several advantages of the inventive stimulation system and methods described herein are made clear through contrast to existing conventional stimulation systems such as those described in, for example, U.S. Pat. Nos. 6,259,952; 6,319,241 and 6,871,099 each of which are incorporated herein by reference.

Consider for example a conventional stimulation electrode placed within a vertebral body for stimulation of a dorsal root ganglion. A portion of the stimulation energy provided by an electrode so positioned will be attenuated or absorbed by the surrounding bone structure. As a result, the initial stimulation energy provided in this system must be large enough to compensate for propagation losses through the bone while still having sufficient remaining energy to accomplish the desired stimulation level at the dorsal root ganglion. The stimulation energy of this conventional system will also be non-specifically applied to the intervening physiological structures such as the spinal cord, peripheral nerves, dorsal root, ventral root and surrounding tissue, cartilage and muscle. Each of these intervening physiological structures will be subjected to the stimulation energy and may cause undesired consequences. In addition, each of these physiological structures will be subjected to and may attenuate or absorb the stimulation energy before the energy reaches the desired neural tissue.

Consider the additional examples of conventional stimulation electrodes placed (a) within the dorsal root between the spinal dura and the spinal cord and (b) within the peripheral nerve. Neurostimulation of a dorsal root ganglion from these positions is complicated by ways similar to the above example. The stimulation energy provided by the electrode must pass through or may be absorbed by numerous surrounding physiological structures. A portion of the stimulation energy provided by an electrode in position (a) will be attenuated or absorbed by, for example, the surrounding dorsal root sheath, cerebral spinal fluid and the spinal cord. The stimulation energy provided in this system must be large enough to compensate for propagation losses through the dorsal root sheath, cerebral spinal fluid and protective spinal cord layers (i.e., the spinal meninges: pia mater, arachnoid mater and dura mater) while still having sufficient remaining energy to accomplish the desired stimulation level in the dorsal root ganglion. The stimulation energy will also be non-specifically applied to the spinal cord. A portion of the stimulation energy provided by an electrode in position (b) will be attenuated or absorbed by, for example, the peripheral nerve bundles including motor nerve bundles. The stimulation energy provided in this system must be large enough to compensate for propagation losses through the peripheral nerve while still having sufficient remaining energy to accomplish the desired stimulation level in the dorsal root ganglion. Unlike the present invention, the stimulation energy provided by electrode placement (b) will also apply stimulation energy to the motor nerves within the peripheral nerve. Electrode placement in positions (a) and (b) above each have intervening physiological structures that are subjected to the stimulation energy and may cause undesired consequences. In addition, each of the intervening physiological structures will be subjected to and may attenuate or absorb the stimulation energy before the energy reaches the desired neural tissue.

Embodiments of the present invention provide stimulation energy via one or more electrodes placed on, in or in proximity to the targeted neural tissue. The intimate nature of the electrode placement allows substantially less stimulation energy to be used to achieve a comparable neurostimulation level. One reason it is believed that that lower power levels may be used in the inventive techniques is that the lack of attenuation losses caused by subjecting intervening physiological structures to stimulation energy. Conventional systems remain concerned about the generation of heat and the possibility of heat induced tissue damage because conventional stimulation systems subject intervening tissues and targeted tissues to stimulation energy. Many conventional stimulation systems are provided with or utilize tissue temperature for control or feedback. Tissue temperature is a useful parameter for these conventional systems because they provide sufficient energy to substantially or measurably raise the temperature of the surrounding tissue or intervening structures. These conventional stimulation systems raise the temperature of surrounding tissue by tens of degrees Celsius while maintaining temperatures below the average temperature range that is thermally lethal such as that used by heat lesioning procedures (i.e., below 45 C).

In contrast to systems that raise the temperature of both targeted and surrounding tissue, it is believed that the stimulation energy levels provided by embodiments of the present invention are low enough that the temperature of the targeted neural tissue does not increase a measurable amount or less than one degree Celsius. The stimulation levels provided by some embodiments of the present invention are within or below (a) the milliwatt range; (b) the millijoule range and/or (c) the microjoule range. It is also believed that the stimulation levels provided by some embodiments of the present invention are sufficiently low that the temperature of tissue surrounding an electrode is unaffected, increases by less than 5 degrees C., or less than 1 degree C. Moreover, it is believed that the stimulation energy levels provided by other embodiments of the present invention are low enough that the temperature of the surrounding tissue and other physiological structures is below a measurable amount using conventional temperature measurement techniques or below one degree Celsius. It is to be appreciated that the stimulation energy levels provided by embodiments of the present invention are substantially below those conventional stimulation systems that measurably elevate the temperature of surrounding tissue or operate at levels approaching the level of thermal ablation and lesioning.

It is to be appreciated that embodiments of the specific stimulation techniques of the present invention may be utilized alone to achieve the described stimulation techniques or in a combined upstream or downstream configurations with the described stimulation techniques and systems described in the following references (each of which is incorporated herein in its entirety): U.S. Pat. No. 5,948,007 to Starkebaum; U.S. Pat. No. 5,417,719 to Hull; U.S. Pat. No. 6,658,302 to Kuzma; U.S. Pat. No. 6,606,521 to Paspa; and U.S. Pat. No. 5,938,690 to Law.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of pharmacologically modulating a dorsal root ganglion comprising:
    implanting an elongate body into an epidural space, wherein the elongate body has a conduit for delivery of a pharmacological agent;
    advancing the elongate body along a nerve root and positioning an outlet of the conduit near the dorsal root ganglion associated with the nerve root; and
    delivering a pharmacological agent from an implanted delivery device through the conduit so that the pharmacological agent pharmacologically modulates the dorsal root ganglion without pharmacologically modulating an associated ventral root, wherein the implanted delivery device comprises a reservoir for storing the pharmacological agent and a pump for moving the pharmacological agent from the reservoir to the conduit.

2. The method as in claim 1, wherein the pharmacological agent modulates the dorsal root ganglion by acting upon at least one cell body within the dorsal root ganglion.

3. The method as in claim 1, wherein the pharmacological agent modifies electrophysiological excitability of the dorsal root ganglion.

4. The method as in claim 3, wherein the electrophysiological excitability of the dorsal root ganglion is decreased at least in part by reducing the extent of membrane depolarization.

5. The method as in claim 1, wherein the pharmacological agent comprises a pharmacological blocker.

6. The method as in claim 1, wherein the pharmacological blocker comprises an $Na^+$ channel blocker, a $Ca^{2+}$ channel blocker, an NMDA receptor blocker and/or an opioid analgesic.

7. The method as in claim 1, wherein the pharmacological agent reduces an activation potential of a nerve fiber.

8. The method as in claim 1, wherein the pharmacological agent affects at least one $Na^+$ channel and/or at least one $Ca^{2+}$ channel.

9. A method of pharmacologically modulating a dorsal root ganglion comprising:
    advancing a distal end of an elongate body along a portion of a peripheral nerve toward the dorsal root ganglion and a midline of a spinal column;
    implanting the distal end near the dorsal root ganglion; and
    delivering a pharmacological agent from an implanted delivery device through the distal end of the elongate body so that the pharmacological agent pharmacologically modulates the dorsal root ganglion, wherein the implanted delivery device comprises a reservoir for storing the pharmacological agent and a pump for moving the pharmacological agent from the reservoir to the elongate body.

10. The method as in claim 9, wherein the pharmacological agent modulates the dorsal root ganglion by acting upon at least one cell body within the dorsal root ganglion.

11. The method as in claim 9, wherein the pharmacological agent modifies electrophysiological excitability of the dorsal root ganglion.

12. The method of claim 11, wherein the electrophysiological excitability of the dorsal root ganglion is decreased at least in part by reducing the extent of membrane depolarization.

13. The method as in claim 9, wherein the pharmacological agent comprises a pharmacological blocker.

14. The method as in claim 13, wherein the pharmacological blocker comprises an $Na^+$ channel blocker, a $Ca^{++}$ channel blocker, an NMDA receptor blocker or an opioid analgesic.

15. The method as in claim 9, wherein the pharmacological agent reduces an activation potential of a nerve fiber.

16. The method as in claim 9, wherein the pharmacological agent affects at least one $Na^+$ channel and/or at least one $Ca^{2+}$ channel.

* * * * *